United States Patent
Chittibabu et al.

(10) Patent No.: US 11,286,244 B2
(45) Date of Patent: *Mar. 29, 2022

(54) SOLAR CELL DYES FOR COPPER REDOX BASED DYE SENSITIZED SOLAR CELLS AND COMBINATIONS THEREOF

(71) Applicant: AMBIENT PHOTONICS, INC., Mill Valley, CA (US)

(72) Inventors: Kethinni Chittibabu, Mill Valley, CA (US); John C. Warner, Mill Valley, CA (US); Debora Martino, Mill Valley, CA (US); Rich Allen, Mill Valley, CA (US); Sammaiah Thota, Mill Valley, CA (US)

(73) Assignee: AMBIENT PHOTONICS, INC., Mill Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/003,248

(22) Filed: Aug. 26, 2020

(65) Prior Publication Data

US 2020/0392097 A1 Dec. 17, 2020

Related U.S. Application Data

(63) Continuation of application No. PCT/US2019/040955, filed on Jul. 9, 2019.

(60) Provisional application No. 62/696,010, filed on Jul. 10, 2018.

(51) Int. Cl.
| | | |
|---|---|---|
| *C07D 307/80* | (2006.01) | |
| *C07D 417/14* | (2006.01) | |
| *H01G 9/20* | (2006.01) | |
| *H01L 51/00* | (2006.01) | |
| *H01L 51/44* | (2006.01) | |

(52) U.S. Cl.
CPC ......... *C07D 307/80* (2013.01); *C07D 417/14* (2013.01); *H01G 9/2031* (2013.01); *H01G 9/2059* (2013.01); *H01L 51/0059* (2013.01); *H01L 51/0065* (2013.01); *H01L 51/0069* (2013.01); *H01L 51/44* (2013.01)

(58) Field of Classification Search
CPC .............. H01G 9/20–2095; H01L 51/42–448
See application file for complete search history.

(56) References Cited

U.S. PATENT DOCUMENTS

| | | | |
|---|---|---|---|
| 2005/0038107 A1 | 2/2005 | Miller et al. | |
| 2009/0272934 A1 | 11/2009 | Chittibabu et al. | |
| 2011/0061723 A1* | 3/2011 | Kunimoto | H01L 51/0064 136/252 |
| 2011/0226306 A1 | 9/2011 | Warner | |
| 2015/0213966 A1* | 7/2015 | Holcombe | H01L 51/0065 252/500 |
| 2015/0246902 A1 | 9/2015 | McComas et al. | |
| 2018/0099953 A1 | 4/2018 | Wang et al. | |
| 2021/0082632 A1* | 3/2021 | Warner | C09B 23/105 |

FOREIGN PATENT DOCUMENTS

| | | | |
|---|---|---|---|
| WO | WO-2014051007 A1 * | 4/2014 | ...... C09B 57/008 |
| WO | WO2016/111636 A1 | 7/2016 | |
| WO | WO2017/083488 A1 | 5/2017 | |
| WO | WO2018/208712 A1 | 11/2018 | |

OTHER PUBLICATIONS

Justin Thomas, et al. "Fluorene based organic dyes for dye sensitised solar cells: structure-property relationships." Materials Technology 28.1-2 (2013): 71-87.*
Wu, et al. "Effect of different acceptors in di-anchoring triphenylamine dyes on the performance of dye-sensitized solar cells." Dyes and Pigments 105 (2014): 1-6.*
Li, et al. "Co-sensitization of benzoxadiazole based D-A-π-A featured sensitizers: compensating light-harvesting and retarding charge recombination." Journal of Materials Chemistry A 2.35 (2014): 14649-14657.*
Duan, et al. "End-capped "thiophene-free" organic dye for dye-sensitized solar cell: Optimized donor, broadened spectra and enhanced open-circuit voltage." Dyes and Pigments 124 (2016): 45-52.*
Zhang, et al. "Molecular engineering of potent sensitizers for very efficient light harvesting in thin-film solid-state dye-sensitized solar cells." Journal of the American Chemical Society 138.34 (2016): 10742-10745.*
Li, et al. "D-A-π-A system: light harvesting, charge transfer, and molecular designing." The Journal of Physical Chemistry C 121.23 (2017): 12546-12561.*
Panneerselvam, et al. "The role of π-linkers in tuning the optoelectronic properties of triphenylamine derivatives for solar cell applications—A DFT/TDDFT study." Physical Chemistry Chemical Physics 19.8 (2017): 6153-6163.*
Huang, et al. "Dithienopyrrolobenzotriazole-based organic dyes with high molar extinction coefficient for efficient dye-sensitized solar cells." Dyes and Pigments 125 (2016): 229-240.*

(Continued)

*Primary Examiner* — William E McClain
(74) *Attorney, Agent, or Firm* — Cermak Nakajima & McGowan LLP; Malcolm K. McGowan

(57) ABSTRACT

The present application discloses compounds and compositions, useful in the manufacture of dye-sensitized solar cells and other similar technology.

3 Claims, No Drawings

(56) References Cited

OTHER PUBLICATIONS

Raoui, et al. "Highly fluorescent extended 2-(2'-hydroxyphenyl) benzazole dyes: synthesis, optical properties and first-principle calculations." Chemical Communications 52.59 (2016): 9216-9219.*
Jung, et al. "Synthesis and photovoltaic properties of efficient organic dyes containing the benzo [b] furan moiety for solar cells." The Journal of organic chemistry 72.10 (2007): 3652-3658.*
International Search Report and Written Opinion for PCT Patent App. No. PCT/US2019/040955 (dated Oct. 24, 2019).
International Preliminary Report On Patentability for PCT Patent App. No. PCT/US2019/040955 (dated Jan. 12, 2021).

* cited by examiner

SOLAR CELL DYES FOR COPPER REDOX BASED DYE SENSITIZED SOLAR CELLS AND COMBINATIONS THEREOF

CROSS-REFERENCE TO RELATED APPLICATIONS

The present application is a Continuation of, and claims priority under 35 USC 111 to, International Application PCT/US2019/040955, filed Jul. 9, 2019, which claims priority to U.S. Provisional Application 62/696,010, filed Oct. 17, 2018. The contents of these priority applications are incorporated by reference herein in their entirety.

TECHNICAL FIELD

The present invention is in the field of material compositions used to assemble dye sensitized solar cells (DSSC) and other dye sensitized electronic devices such as information storage devices, sensing devices and imaging devices. In particular, it concerns the utility of novel organic chromophores and chromophore combinations as the sensitizing dyes in dye sensitized electronic devices.

BACKGROUND

Sensitization of semiconductor solids such as metal oxides in imaging devices, memories, sensors, and solar cells can serve as an effective means of energy transduction. These devices use metal oxides, such as titanium dioxide that are transparent to light but can be sensitized to the desired spectrum through the use of sensitizing agents that absorb light energy and transduce it into electrical power or an electrical signal. This sensitization occurs through charge injection into the metal oxide from the excited state of the dye sensitizer. Sensitizers such as transition metal complexes, inorganic colloids and organic dye molecules are used.

Prominent among such technologies is the dye-sensitized metal oxide solar cell (DSSC). DSSCs use a dye to absorb light and initiate a rapid electron transfer to a nanostructured oxide such as $TiO_2$. The mesoscopic structure of the $TiO_2$ allows building of thick, nanoporous films with active-layer thicknesses of several microns. The dye is then adsorbed on the large surface area of the mesoporous $TiO_2$. Charge balance and transport is achieved by a layer having a REDOX couple, such as iodide/triiodide, Co(II)/Co(III) complexes, and Cu(I)/Cu(II) complexes.

Dyes based on transition metal complexes are disclosed in Gratzel et al., U.S. Pat. Nos. 4,927,721 and 5,350,644. These dye materials are disposed on mesoporous metal oxides that have a high surface area on which the absorbing, sensitizing layer can be formed. This results in a high absorptivity of light in the cell. Dyes such as Ru(II) (2,2'-bipyridyl 4,4' dicarboxylate)$_2$ (NCS)$_2$ have been found to be efficient sensitizers and can be attached to the metal oxide solid through carboxyl or phosphonate groups on the periphery of the compounds. However, when transition metal ruthenium complexes are used as sensitizers they must be applied to the mesoporous metal oxide layers in a coat as thick as 10 micrometers or thicker in order to absorb enough solar radiation to attain sufficient power conversion efficiencies. Further, the ruthenium complexes are expensive. In addition, such dyes must be applied using volatile organic solvents, co-solvents, and diluents because they are not dispersible in water. Volatile organic compounds (VOCs) are significant pollutants that can affect the environment and human health. While VOCs are usually not acutely toxic, they may have chronic health and environmental effects. For this reason, governments around the world are seeking to reduce the levels of VOCs.

One type of dye-sensitized solar cell is known as the Gratzel cell. Hamann et al. (2008), "Advancing beyond current generation dye-sensitized solar cells," *Energy Environ. Sci.* 1:66-78 (the disclosure of which is incorporated in its entirety by reference), describes the Gratzel cell. The Gratzel cell includes crystalline titanium dioxide nanoparticles serving as a photoanode in the photovoltaic cell. The titanium dioxide is coated with light sensitive dyes. The titanium dioxide photoanode includes 10-20 nm diameter titanium dioxide particles forming a 12 μm transparent film. The 12 μm titanium dioxide film is made by sintering the 10-20 nm diameter titanium dioxide particles so that they have a high surface area. The titanium dioxide photoanode also includes a 4 μm film of titanium dioxide particles having a diameter of about 400 nm. The coated titanium dioxide films are located between two transparent conducting oxide (TCO) electrodes. Also disposed between the two TCO electrodes is an electrolyte with a redox shuttle.

The Gratzel cell may be made by first constructing a top portion. The top portion may be constructed by depositing fluorine-doped tin dioxide ($SnO_2F$) on a transparent plate, which is usually glass. A thin layer of titanium dioxide ($TiO_2$) is deposited on the transparent plate having a conductive coating. The $TiO_2$ coated plate is then dipped into a photosensitized dye such as ruthenium-polypyridine dye in solution. A thin layer of the dye covalently bonds to the surface of the titanium dioxide. A bottom portion of the Gratzel cell is made from a conductive plate coated with platinum metal. The top portion and the bottom portion are then joined and sealed. The electrolyte, such as iodide-triiodide, is then typically inserted between the top and bottom portions of the Gratzel cell.

Typically, thin films for Dye Sensitized Solar Cells (DSSC) are composed of a single metal oxide—usually titanium dioxide, which in addition to nanoparticles, may be utilized in the form of larger 200 to 400 nm scale particles or as dispersed nanoparticles formed in-situ from a titanium alkoxide solution. In one embodiment, the present application discloses the use of multiple morphologies of titanium oxide as well as other metal oxides, which provide a boost in efficiency over the single metal oxide system. The additional metal oxides that may be employed include, but are not limited to, alpha aluminum oxide, gamma aluminum oxide, fumed silica, silica, diatomaceous earth, aluminum titanate, hydroxyapatite, calcium phosphate and iron titanate; and mixtures thereof. These materials may be utilized in conjunction with traditional titanium oxide thin films or with a thin film dye sensitized solar cell system In operation, the dye absorbs sunlight, which results in the dye molecules becoming excited and transmitting electrons into the titanium dioxide. The titanium dioxide accepts the energized electrons, which travel to a first TCO electrode. Concurrently, the second TCO electrode serves as a counter electrode, which uses a redox couple such as iodide-triiodide ($I_3^-/I^-$) to regenerate the dye. If the dye molecule is not reduced back to its original state, the oxidized dye molecule decomposes. As the dye-sensitized solar cell undergoes a large number of the oxidation-reduction cycles in the lifetime of operation, more and more dye molecules undergo decomposition over time, and the cell energy conversion efficiency decreases.

Hattori and his coworkers (Hattori, S., et al. (2005) "Blue copper model complexes with distorted tetragonal geometry acting as effective electron-transfer mediators in dye-sensitized solar cells. *J. Am. Chem. Soc.*, 127: 9648-9654) have used copper (I/II) redox couples in DSSCs using ruthenium-based dyes, with very low resulting efficiencies. Peng Wang and his coworkers improved the performance of copper redox-based dye DSSCs using an organic dye (Bai, Y., et a. (2011) *Chem. Commun.*, 47: 4376-4378). The voltage generated from such cells far exceeded voltage generated by any iodide/triiodide based redox couple.

SUMMARY OF THE INVENTION

A dye sensitized solar cell (DSSC) is a low-cost solar cell, often a thin film solar cell. The present application discloses high efficient dye sensitized solar cells, and solar cell dyes for use in such DSSCs. In a particular embodiment, the solar cell is based on a semiconductor that is formed between a photo-sensitized anode and an electrode.

Described herein is a solar cell dye for use in a DSSC, wherein the dye is a compound of formula I and its structural isomers:

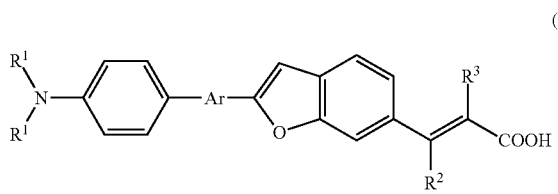

(I)

wherein each $R^1$ is independently selected from the group consisting of substituted or unsubstituted linear or branched $C_1$-$C_{10}$ alkyl, substituted or unsubstituted phenyl, substituted or unsubstituted $C_6$-$C_{12}$ aryl (including fused, bicyclic and tricyclic aryl), substituted or unsubstituted $C_4$-$C_{12}$ heteroaryl (including fused, bicyclic and tricyclic heteroaryl), substituted or unsubstituted $C_5$-$C_{10}$ cycloalkyl, and substituted or unsubstituted $C_5$-$C_{10}$ heterocycloalkyl; —Ar— is a pi-bridge; $R^2$ and $R^3$ are independently selected from the group consisting of H, —CN, —COOH, —X, substituted or unsubstituted linear or branched $C_1$-$C_{10}$ alkyl, —COOR, —CONHR, —CON(H)OR, —SO$_3$R, —SO$_2$R—OSO$_3$R, —PO$_3$HR, and —OPO$_3$HR; X is halogen; and R is substituted or unsubstituted linear or branched $C_1$-$C_{10}$ alkyl.

Also described herein is a solar cell dye for use in a DSSC, wherein the dye is a compound of formula II and its structural isomers

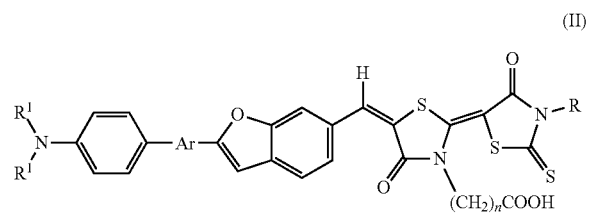

(II)

wherein each $R^1$ is independently selected from the group consisting of substituted or unsubstituted linear or branched $C_1$-$C_{10}$ alkyl, substituted or unsubstituted phenyl, substituted or unsubstituted $C_6$-$C_{12}$ aryl (including fused, bicyclic and tricyclic aryl), substituted or unsubstituted $C_4$-$C_{12}$ heteroaryl (including fused, bicyclic and tricyclic heteroaryl), substituted or unsubstituted $C_5$-$C_{10}$ cycloalkyl, and substituted or unsubstituted $C_5$-$C_{10}$ heterocycloalkyl; —Ar— is a pi-bridge; n is an integer from 1 to 10; and R is substituted or unsubstituted linear or branched $C_1$-$C_{10}$ alkyl.

Further described herein is a solar cell dye for use in a DSSC, wherein the dye is a compound of formula III and its structural isomers:

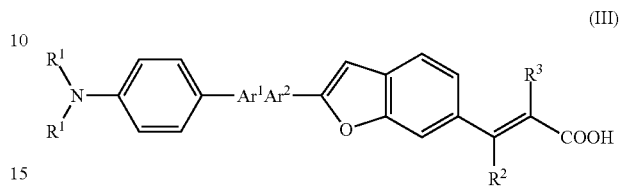

(III)

wherein each $R^1$ is independently selected from the group consisting of substituted or unsubstituted linear or branched $C_1$-$C_{10}$ alkyl, substituted or unsubstituted phenyl, substituted or unsubstituted $C_6$-$C_{12}$ aryl (including fused, bicyclic and tricyclic aryl), substituted or unsubstituted $C_4$-$C_{12}$ heteroaryl (including fused, bicyclic and tricyclic heteroaryl), substituted or unsubstituted $C_5$-$C_{10}$ cycloalkyl, and substituted or unsubstituted $C_5$-$C_{10}$ heterocycloalkyl; —Ar— is an electron-withdrawing pi-bridge; —Ar$^2$— is an electron-donating pi-bridge; $R^2$ and $R^3$ are independently selected from the group consisting of H, —CN, —COOH, —X, substituted or unsubstituted linear or branched $C_1$-$C_{10}$ alkyl, —COOR, —CONHR, —CON(H)OR, —SO$_3$R, —SO$_2$R—OSO$_3$R, —PO$_3$HR, and —OPO$_3$HR; X is halogen; and R is substituted or unsubstituted linear or branched $C_1$-$C_{10}$ alkyl.

Also described herein is a solar cell dye for use in a DSSC, wherein the dye is a compound of formula IV and its structural isomers:

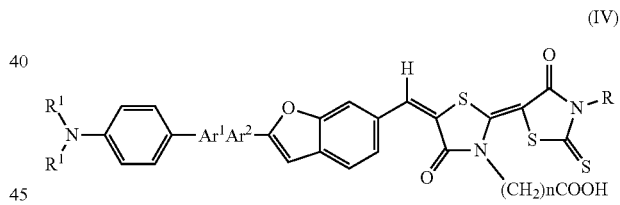

(IV)

wherein each $R^1$ is independently selected from the group consisting of substituted or unsubstituted linear or branched $C_1$-$C_{10}$ alkyl, substituted or unsubstituted phenyl, substituted or unsubstituted $C_6$-$C_{12}$ aryl (including fused, bicyclic and tricyclic aryl), substituted or unsubstituted $C_4$-$C_{12}$ heteroaryl (including fused, bicyclic and tricyclic heteroaryl), substituted or unsubstituted $C_5$-$C_{10}$ cycloalkyl, and substituted or unsubstituted $C_5$-$C_{10}$ heterocycloalkyl; —Ar$^1$— is an electron-withdrawing pi-bridge; —Ar$^2$— is an electron-donating pi-bridge; n is an integer from 1 to 10; and R is substituted or unsubstituted linear or branched $C_1$-$C_{10}$ alkyl.

Further described herein are solar cell dye combinations that exhibit synergistic effect when the combination is used with TiO$_2$ in dye sensitized solar cells (DSSCs) in general and copper redox based DSSCs in particular. The voltage generated from the dye combination is higher than that from individual dye-based solar cells; overall current generated is often higher than sum of both dyes using additive effect; and overall power generated is higher than that from individual dye based solar cells. The synergistic effect is seen with both acetonitrile-based volatile electrolytes and sulfolane based stable electrolyte formulations.

The present inventors have surprisingly discovered unexpected improvements in voltage, current density and overall power density when a benzofuran-containing dye such as WD3 is sensitized with commercial dyes such as XY1b. The generated voltage is higher than that from either WD3 dye-based or XY1b dye-based DSSCs. This synergistic improvement is not seen when two benzofuran containing dyes or two non-benzofuran containing dyes are combined.

The dye combinations can be used as efficient sensitizers in dye sensitized solar cells. These molecules will also help in using energy mismatched dye molecules (e.g., a blue dye which will not work by itself can be used to harvest light of 600-800 nm wavelength) for making high efficiency solar cells.

The present application contains the first description of synergistic dye combinations that exhibit performance higher than additive combination of two dyes. Because of this surprising and unexpected synergy, the dye combinations described herein are particularly useful for fabricating high performance solar cells for harvesting sun and indoor light.

Described herein is a solar cell dye composition comprising a benzofuran-containing dye and a non-benzofuran-containing dye.

Also described herein are DSSCs incorporating a solar cell dye as described above. Still further described herein are methods of making DSSCs comprising the step of incorporating a solar cell dye as described above.

DETAILED DESCRIPTION

Definitions

Unless specifically noted otherwise herein, the definitions of the terms used are standard definitions used in the art of organic chemistry. Exemplary embodiments, aspects and variations are illustrated in the figures and drawings, and it is intended that the embodiments, aspects and variations, and the figures and drawings disclosed herein are to be considered illustrative and not limiting.

While particular embodiments are shown and described herein, it will be obvious to those skilled in the art that such embodiments are provided by way of example only. Numerous variations, changes, and substitutions will now occur to those skilled in the art. It should be understood that various alternatives to the embodiments described herein may be employed in practicing the methods described herein. It is intended that the appended claims define the scope of the invention and that methods and structures within the scope of these claims and their equivalents be covered thereby.

Unless defined otherwise, all technical and scientific terms used herein have the same meaning as is commonly understood by one of skill in the art. All patents and publications referred to herein are incorporated by reference.

As used in the specification and claims, the singular form "a," "an," and "the" include plural references unless the context clearly dictates otherwise.

Unless otherwise stated, structures depicted herein are also meant to include dyes which differ only in the presence of one or more isotopically enriched atoms. For example, dyes as described herein wherein one or more hydrogens are replaced by deuterium or tritium, or the replacement of one or more carbon atoms by the $^{13}$C- or $^{14}$C-enriched carbon isotope. Further, substitution with heavier isotopes, particularly deuterium ($^{2}$H or D) may afford certain advantages resulting from greater stability, increased half-life, etc. It is understood that deuterium in this context is regarded as a substituent of a dye of the formula (I). The dyes described herein may also contain unnatural proportions of atomic isotopes at one or more of atoms that constitute such dyes. For example, the dyes may be radiolabeled with radioactive isotopes, such as for example tritium ($^{3}$H), iodine-25 ($^{125}$I) or carbon-14 ($^{14}$C). All isotopic variations of the dyes described herein, whether radioactive or not, are encompassed.

"Benzofuran-containing" dyes, as used herein, refers to solar cell dyes whose chemical structure comprises a unit having chemical structure

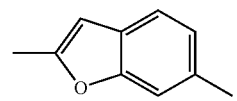

where the open links in this structure indicate where this unit is linked to the rest of the dye structure. One or more of the four ring hydrogens on this unit may be substituted.

"Non-benzofuran-containing" dyes, as used herein, are solar cell dyes that are not benzofuran-containing dyes.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "( . . . +− . . . )" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the dyes described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

When the dyes described herein contain olefinic double bonds or other centers of geometric asymmetry, and unless specified otherwise, it is intended that the dyes include both E and Z geometric isomers.

A "substituted" or "optionally substituted" group, as used herein, means that a group (such as alkyl, aryl, heterocyclyl, cycloalkyl, hetrocyclylalkyl, arylalkyl, heteroaryl, or heteroarylalkyl) unless specifically noted otherwise, may have 1, 2 or 3 —H groups substituted by 1, 2 or 3 substituents selected from halo, trifluoromethyl, trifluoromethoxy, methoxy, —COOH, —CHO, —NH$_2$, —NO$_2$, —OH, —SH, —SMe, —NHCH$_3$, —N(CH$_3$)$_2$, —CN and the like.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

As used herein, the term "pi-bridge" refers to a chemical moiety, comprising two ends available for covalent linkage (hence "bridge") and comprising one or more carbon-carbon, heteroatom-carbon, or heteroatom-heteroatom double or triple pi-pi bonds (hence "pi"). The double or triple bonds are conjugated, and one end of a double or triple bond must lie adjacent to each covalent end. Double bonds in each pi-bridge may be part of a linear, cyclic, bicyclic or polycyclic structure.

Pi-bridges contemplated herein include, but are not limited to, those shown in Table 1:

TABLE 1

| Electron-accepting pi-bridges | Electron-donating pi-bridges |
|---|---|
| 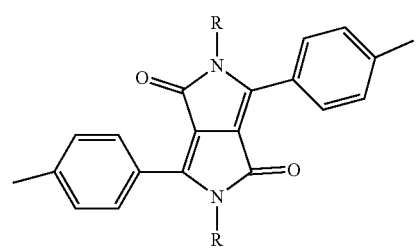 | 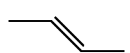 |
| 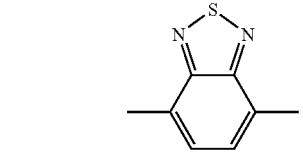 | 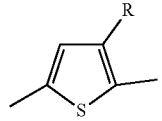 |
| 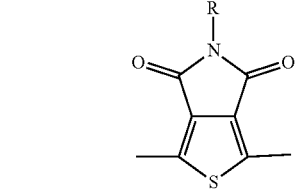 | 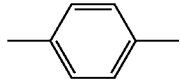 |
| 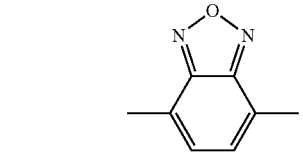 |  |
| | 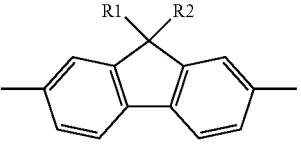 |
| | 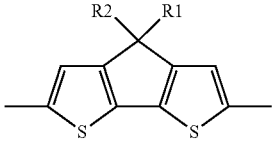 |

TABLE 1-continued

| Electron-accepting pi-bridges | Electron-donating pi-bridges |
|---|---|
| | 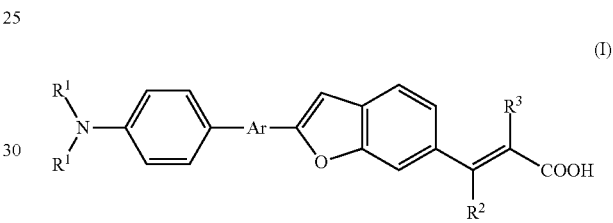 |

In the above Table 1, each R, $R^1$ and $R^2$ are independently selected from the group consisting of H, —CN, —COOH, —X, substituted or unsubstituted linear or branched $C_1$-$C_{10}$ alkyl, —COOR, CONHR, CON(H)OR, —SO$_3$R, —SO$_2$R—OSO$_3$R, —PO$_3$HR, and —OPO$_3$HR; X is halogen; and R is substituted or unsubstituted linear or branched $C_1$-$C_{10}$ alkyl.

Dyes described herein also include crystalline and amorphous forms of those dyes, including, for example, polymorphs, pseudopolymorphs, solvates, hydrates, unsolvated polymorphs (including anhydrates), conformational polymorphs, and amorphous forms of the dyes, as well as mixtures thereof. "Crystalline form," "polymorph," and "novel form" may be used interchangeably herein, and are meant to include all crystalline and amorphous forms of the dye listed above, as well as mixtures thereof, unless a particular crystalline or amorphous form is referred to.

"Solvent," "organic solvent," and "inert solvent" each means a solvent inert under the conditions of the reaction being described in conjunction therewith including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of the limiting reagent, one cc (or mL) of solvent constitutes a volume equivalent.

Compositions
Dye-Sensitized Solar Cells

Dye-sensitized solar cells (DSSCs) described herein comprise a photoanode, a photocathode, and a redox electrolyte disposed between the photoanode and the photocathode.

The photoanode comprises a metal oxide such as titanium dioxide. The oxide can be in the form of nanoparticles such as mesoporous titanium oxide nanoparticles. The photoanode is sensitized with a solar cell dye deposited on a flexible metal, a transparent conducting substrate, or a fluorine-doped tin oxide coated glass. The photocathode comprises a catalytic layer comprising one or more thin layers of platinum, polythiophenes including PEDOT, polyanilines, polypyrroles, or carbon (including carbon nanotubes and graphenes). The redox electrolyte is commonly selected from a pair consisting of iodide/triiodide, Co(II)/Co(III) organic ligand complexes, and Cu(I)/Cu(II) organic ligand complexes.

The DSSCs described herein also comprise one or more solar cell dyes as described herein.

Benzofuran-Containing Dyes

Also described herein are solar cell dyes for use in a DSSC, wherein the dye is a compound of formula I:

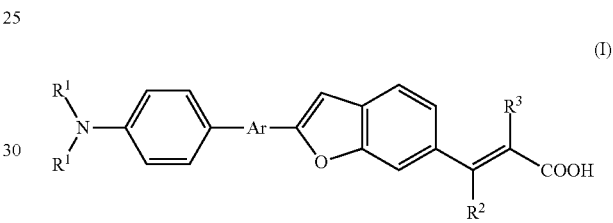

(I)

wherein each $R^1$ is independently selected from the group consisting of substituted or unsubstituted linear or branched $C_1$-$C_{10}$ alkyl, substituted or unsubstituted phenyl, substituted or unsubstituted $C_6$-$C_{12}$ aryl (including fused, bicyclic and tricyclic aryl), substituted or unsubstituted $C_4$-$C_{12}$ heteroaryl (including fused, bicyclic and tricyclic heteroaryl), substituted or unsubstituted $C_5$-$C_{10}$ cycloalkyl, and substituted or unsubstituted $C_5$-$C_{10}$ heterocycloalkyl; —Ar— is a pi-bridge; $R^2$ and $R^3$ are independently selected from the group consisting of H, —CN, —COOH, —X, substituted or unsubstituted linear or branched $C_1$-$C_{10}$ alkyl, —COOR, —CONHR, —CON(H)OR, —SO$_3$R, —SO$_2$R—OSO$_3$R, —PO$_3$HR, and —OPO$_3$HR; X is halogen; and R is substituted or unsubstituted linear or branched $C_1$-$C_{10}$ alkyl.

Also described herein is a solar cell dye for use in a DSSC, wherein the dye is a compound of formula II and its structural isomers

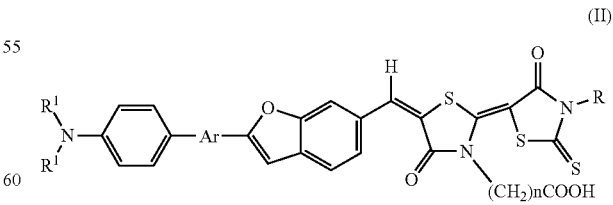

(II)

wherein each $R^1$ is independently selected from the group consisting of substituted or unsubstituted linear or branched $C_1$-$C_{10}$ alkyl, substituted or unsubstituted phenyl, substituted or unsubstituted $C_6$-$C_{12}$ aryl (including fused, bicyclic and tricyclic aryl), substituted or unsubstituted $C_4$-$C_{12}$ heteroaryl (including fused, bicyclic and tricyclic heteroaryl), substituted or unsubstituted C$_5$-C$_{10}$ cycloalkyl, and substituted or unsubstituted C$_5$-C$_{10}$ heterocycloalkyl; —Ar— is a pi-bridge; n is an integer from 1 to 10; and R is substituted or unsubstituted linear or branched C$_1$-C$_{10}$ alkyl.

Further described herein is a solar cell dye for use in a DSSC, wherein the dye is a compound of formula III and its structural isomers:

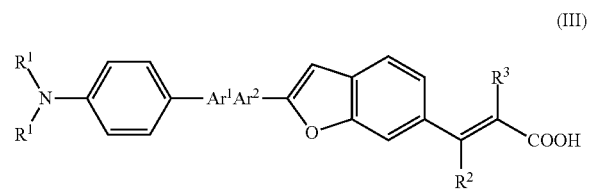
(III)

wherein each R$^1$ is independently selected from the group consisting of substituted or unsubstituted linear or branched C$_1$-C$_{10}$ alkyl, substituted or unsubstituted phenyl, substituted or unsubstituted C$_6$-C$_{12}$ aryl (including fused, bicyclic and tricyclic aryl), substituted or unsubstituted C$_4$-C$_{12}$ heteroaryl (including fused, bicyclic and tricyclic heteroaryl), substituted or unsubstituted C$_5$-C$_{10}$ cycloalkyl, and substituted or unsubstituted C$_5$-C$_{10}$ heterocycloalkyl; —Ar$^1$— is an electron-withdrawing pi-bridge; —Ar$^2$— is an electron-donating pi-bridge; R$^2$ and R$^3$ are independently selected from the group consisting of H, —CN, —COOH, —X, substituted or unsubstituted linear or branched C$_1$-C$_{10}$ alkyl, —COOR, —CONHR, —CON(H)OR, —SO$_3$R, —SO$_2$R—OSO$_3$R, —PO$_3$HR, and —OPO$_3$HR; X is halogen; and R is substituted or unsubstituted linear or branched C$_1$-C$_{10}$ alkyl.

Further described here is a solar cell dye for use in a DSSC, wherein the dye is a compound of formula IV and its structural isomers:

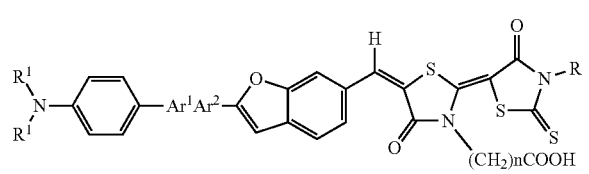
(IV)

wherein each R$^1$ is independently selected from the group consisting of substituted or unsubstituted linear or branched C$_1$-C$_{10}$ alkyl, substituted or unsubstituted phenyl, substituted or unsubstituted C$_6$-C$_{12}$ aryl (including fused, bicyclic and tricyclic aryl), substituted or unsubstituted C$_4$-C$_{12}$ heteroaryl (including fused, bicyclic and tricyclic heteroaryl), substituted or unsubstituted C$_5$-C$_{10}$ cycloalkyl, and substituted or unsubstituted C$_5$-C$_{10}$ heterocycloalkyl; —Ar$^1$— is an electron-withdrawing pi-bridge; —Ar$^2$— is an electron-donating pi-bridge; n is an integer from 1 to 10; and R is substituted or unsubstituted linear or branched C$_1$-C$_{10}$ alkyl.

In each of the above formulae (I)-(IV), in some embodiments each R$^1$ is independently selected from the group consisting of substituted or unsubstituted phenyl, naphthyl, fluorenyl, carbazolyl, biphenyl, thienyl, and pyrrolyl. In other embodiments each R$^1$ is independently selected from the group consisting of substituted or unsubstituted linear or branched C$_1$-C$_{10}$ alkyl. In still other embodiments each R$^1$ is independently selected from the group consisting of substituted or unsubstituted C$_5$-C$_{10}$ cycloalkyl.

The following exemplary solar cell dyes have been synthesized. In each case the molecule identified in the left-hand column (e.g., D0) is represented in three parts, wherein the central portion represents the pi-bridge, with two open covalent bonds. The structure of the entire molecule is visualized by joining the open covalent pi-bridge bonds to the open single bonds from the left and right portions:

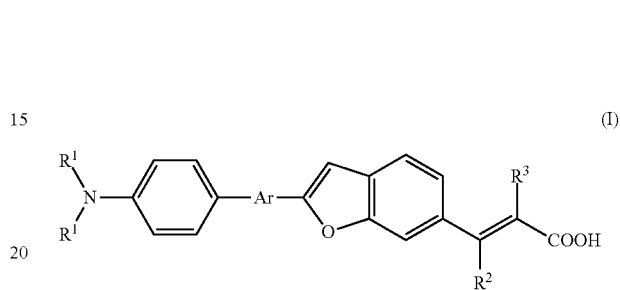
(I)

wherein each R$^1$ is independently selected from the group consisting of substituted or unsubstituted linear or branched C$_1$-C$_{10}$ alkyl, substituted or unsubstituted phenyl, substituted or unsubstituted C$_6$-C$_{12}$ aryl (including fused, bicyclic and tricyclic aryl), substituted or unsubstituted C$_4$-C$_{12}$ heteroaryl (including fused, bicyclic and tricyclic heteroaryl), substituted or unsubstituted C$_5$-C$_{10}$ cycloalkyl, and substituted or unsubstituted C$_5$-C$_{10}$ heterocycloalkyl; —Ar— is a pi-bridge; R$^2$ and R$^3$ are independently selected from the group consisting of H, —CN, —COOH, —X, substituted or unsubstituted linear or branched C$_1$-C$_{10}$ alkyl, —COOR, —CONHR, —CON(H)OR, —SO$_3$R, —SO$_2$R—OSO$_3$R, —PO$_3$HR, and —OPO$_3$HR; X is halogen; and R is substituted or unsubstituted linear or branched C$_1$-C$_{10}$ alkyl.

Also described herein is a solar cell dye for use in a DSSC, wherein the dye is a compound of formula II and its structural isomers

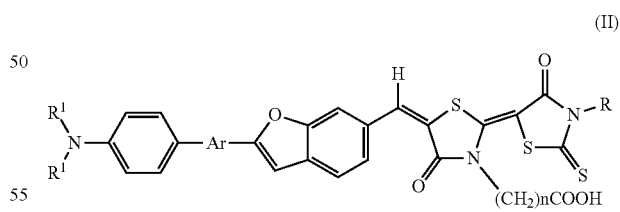
(II)

wherein each R$^1$ is independently selected from the group consisting of substituted or unsubstituted linear or branched C$_1$-C$_{10}$ alkyl, substituted or unsubstituted phenyl, substituted or unsubstituted C$_6$-C$_{12}$ aryl (including fused, bicyclic and tricyclic aryl), substituted or unsubstituted C$_4$-C$_{12}$ heteroaryl (including fused, bicyclic and tricyclic heteroaryl), substituted or unsubstituted C$_5$-C$_{10}$ cycloalkyl, and substituted or unsubstituted C$_5$-C$_{10}$ heterocycloalkyl; —Ar— is a pi-bridge; n is an integer from 1 to 10; and R is substituted or unsubstituted linear or branched C$_1$-C$_{10}$ alkyl.

Further described herein is a solar cell dye for use in a DSSC, wherein the dye is a compound of formula III and its structural isomers:

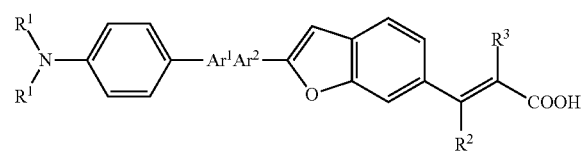

(III)

wherein each $R^1$ is independently selected from the group consisting of substituted or unsubstituted linear or branched $C_1$-$C_{10}$ alkyl, substituted or unsubstituted phenyl, substituted or unsubstituted $C_6$-$C_{12}$ aryl (including fused, bicyclic and tricyclic aryl), substituted or unsubstituted $C_4$-$C_{12}$ heteroaryl (including fused, bicyclic and tricyclic heteroaryl), substituted or unsubstituted $C_5$-$C_{10}$ cycloalkyl, and substituted or unsubstituted $C_5$-$C_{10}$ heterocycloalkyl; —$Ar^1$— is an electron-withdrawing pi-bridge; —$Ar^2$— is an electron-donating pi-bridge; $R^2$ and $R^3$ are independently selected from the group consisting of H, —CN, —OOH, —X, substituted or unsubstituted linear or branched $C_1$-$C_{10}$ alkyl, —COOR, —CONHR, —CON(H)OR, —$SO_3R$, —$SO_2R$—$OSO_3R$, —$PO_3HR$, and —$OPO_3HR$; X is halogen; and R is substituted or unsubstituted linear or branched $C_1$-$C_{10}$ alkyl.

Further described here is a solar cell dye for use in a DSSC, wherein the dye is a compound of formula IV and its structural isomers:

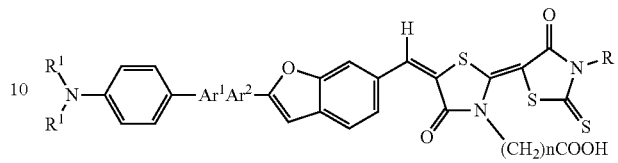

(IV)

wherein each $R^1$ is independently selected from the group consisting of substituted or unsubstituted linear or branched $C_1$-$C_{10}$ alkyl, substituted or unsubstituted phenyl, substituted or unsubstituted $C_6$-$C_{12}$ aryl (including fused, bicyclic and tricyclic aryl), substituted or unsubstituted $C_4$-$C_{12}$ heteroaryl (including fused, bicyclic and tricyclic heteroaryl), substituted or unsubstituted $C_5$-$C_{10}$ cycloalkyl, and substituted or unsubstituted $C_5$-$C_{10}$ heterocycloalkyl; —$Ar^1$— is an electron-withdrawing pi-bridge; —$Ar^2$— is an electron-donating pi-bridge; n is an integer from 1 to 10; and R is substituted or unsubstituted linear or branched $C_1$-$C_{10}$ alkyl.

In each of the above formulae (I)-(IV), in some embodiments each $R^1$ is independently selected from the group consisting of substituted or unsubstituted phenyl, naphthyl, fluorenyl, carbazolyl, biphenyl, thienyl, and pyrrolyl. In other embodiments each $R^1$ is independently selected from the group consisting of substituted or unsubstituted linear or branched $C_1$-$C_{10}$ alkyl. In still other embodiments each $R^1$ is independently selected from the group consisting of substituted or unsubstituted $C_5$-$C_{10}$ cycloalkyl.

The following exemplary solar cell dyes have been synthesized. In each case the molecule identified in the left-hand column (e.g., D0) is represented in three parts, wherein the central portion represents the pi-bridge, with two open covalent bonds. The structure of the entire molecule is visualized by joining the open covalent pi-bridge bonds to the open single bonds from the left and right portions:

| Dye | Donor | Pi-bridge |
|---|---|---|
| D0 | 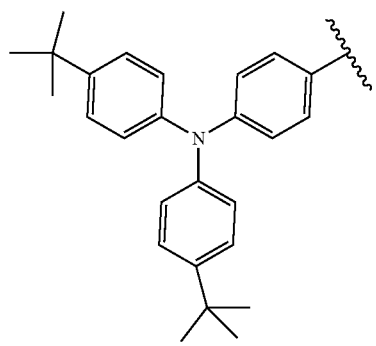 [SMILES: *c1ccc(N(c2ccc(C(C)(C)C)cc2)c2ccc(C(C)(C)C)cc2)cc1] | 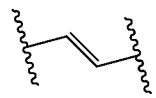 [SMILES: */C=C/*] |

-continued
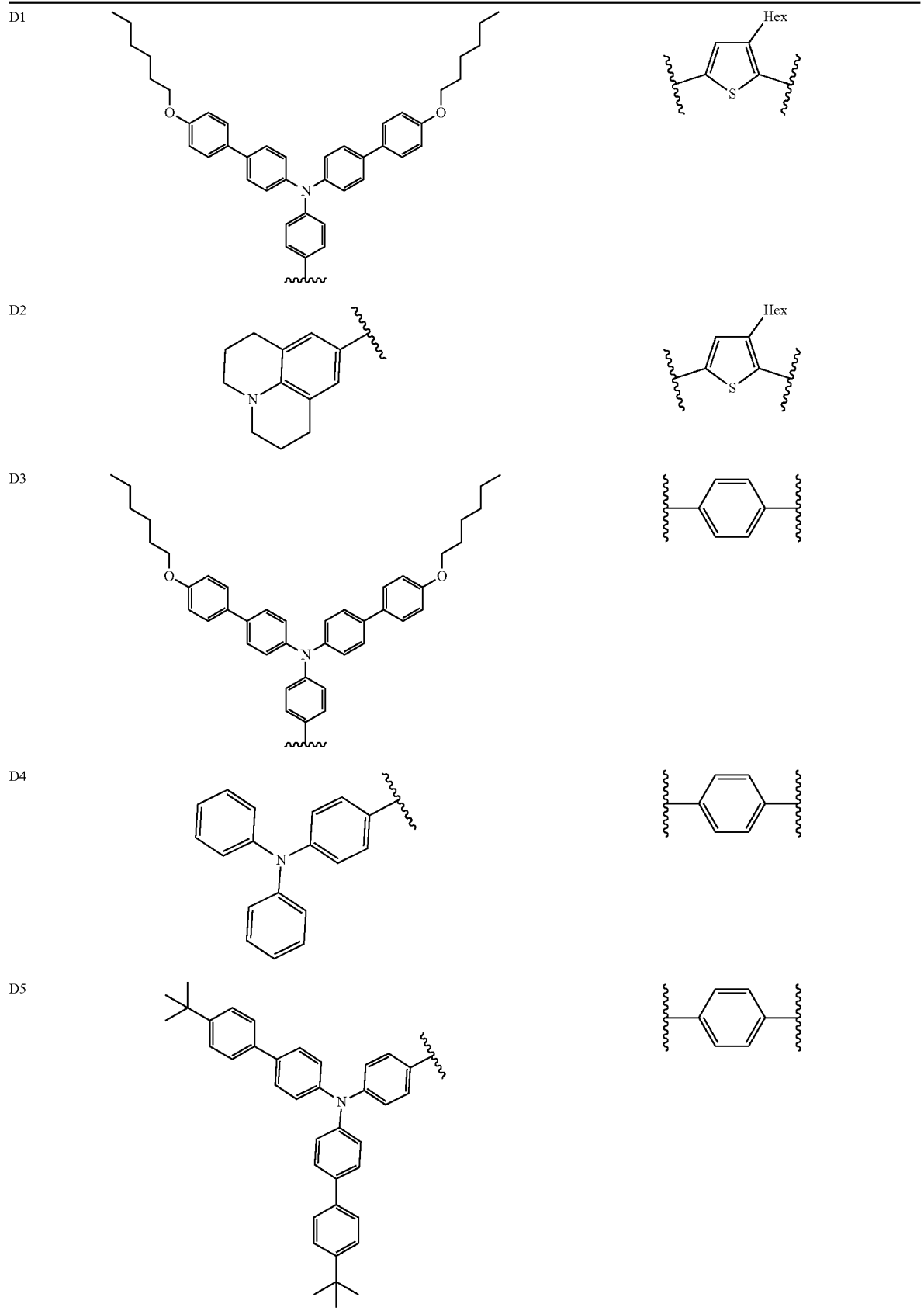

-continued
| | 17 | 18 |
|---|---|---|
| D6 | 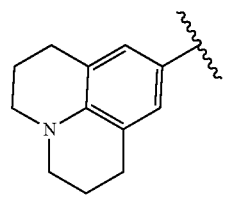 [SMILES: *c1cc2c3c(c1)CCCN3CCC2] | 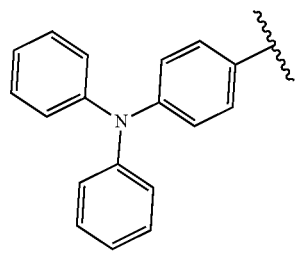 [SMILES: *c1ccc(N(c2ccccc2)c2ccccc2)cc1] |
| D7 | 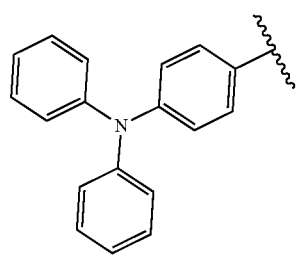 [SMILES: *c1ccc(N(c2ccccc2)c2ccccc2)cc1] | |
| D8 | | |
| D9 | 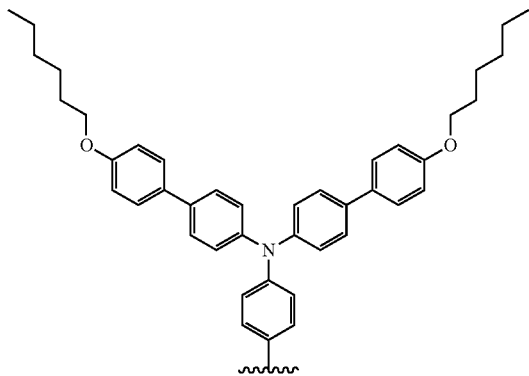 [SMILES: *c1ccc(N(c2ccc(-c3ccc(OCCCCCC)cc3)cc2)c2ccc(-c3ccc(OCCCCCC)cc3)cc2)cc1] | 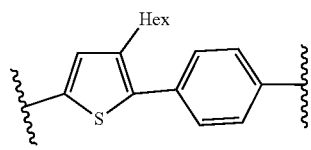 |
| D10 | 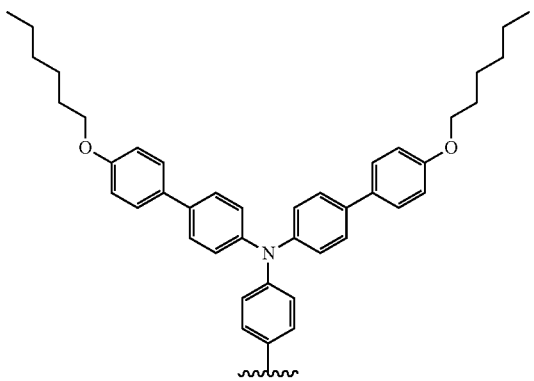 [SMILES: *c1ccc(N(c2ccc(-c3ccc(OCCCCCC)cc3)cc2)c2ccc(-c3ccc(OCCCCCC)cc3)cc2)cc1] | 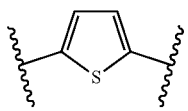 [SMILES: *c1ccc(*)s1] |

-continued
| | 19 | 20 |
|---|---|---|
| D11 | 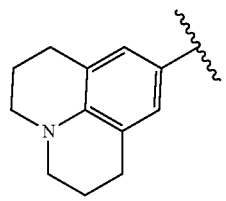 [SMILES: *c1cc2c3c(c1)CCCN3CCC2] | 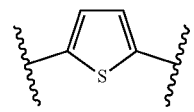 |
| D12 | 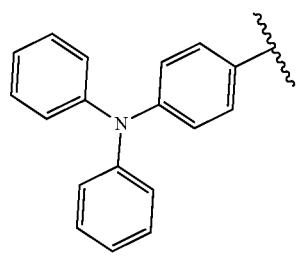 | 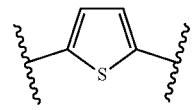 [SMILES: *c1ccc(*)s1] |
| D13 | 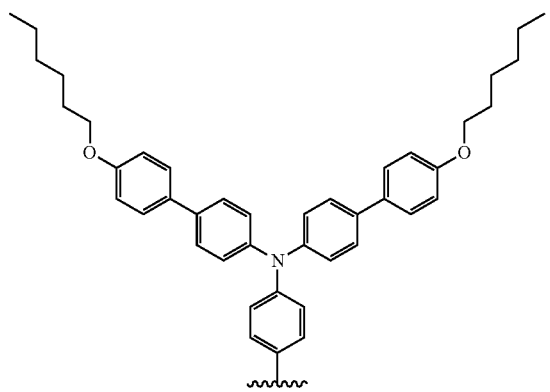 [SMILES: *c1ccc(N(c2ccc(-c3ccc(OCCCCCC)cc3)cc2)c2ccc(-c3ccc(OCCCCCC)cc3)cc2)cc1] | 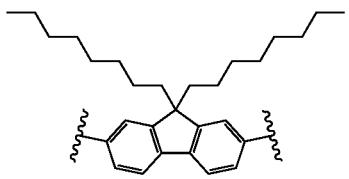 [SMILES: *c1ccc2c(c1)C(CCCCCCCC)(CCCCCCCC)c1cc(*)ccc1-2] |
| D14 | 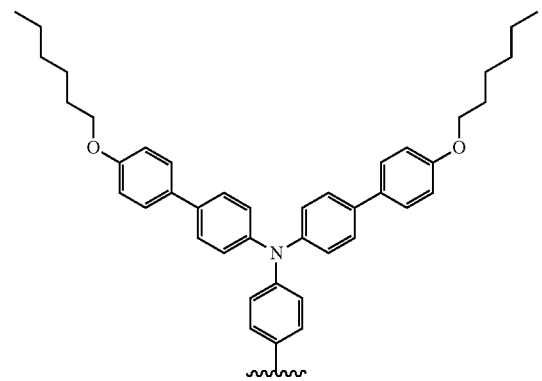 [SMILES: *c1ccc(N(c2ccc(-c3ccc(OCCCCCC)cc3)cc2)c2ccc(-c3ccc(OCCCCCC)cc3)cc2)cc1] | 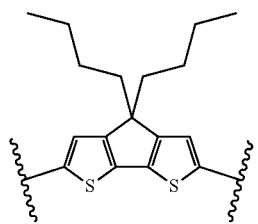 [SMILES: *c1cc2c(s1)-c1sc(*)cc1C2(CCCC)CCCC] |
| D15 | 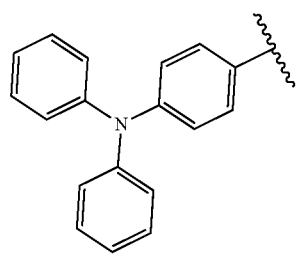 [SMILES: *c1ccc(N(c2ccccc2)c2ccccc2)cc1] | 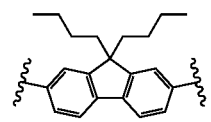 [SMILES: *c1ccc2c(c1)C(CCCC)(CCCC)c1cc(*)ccc1-2] |

-continued
D16 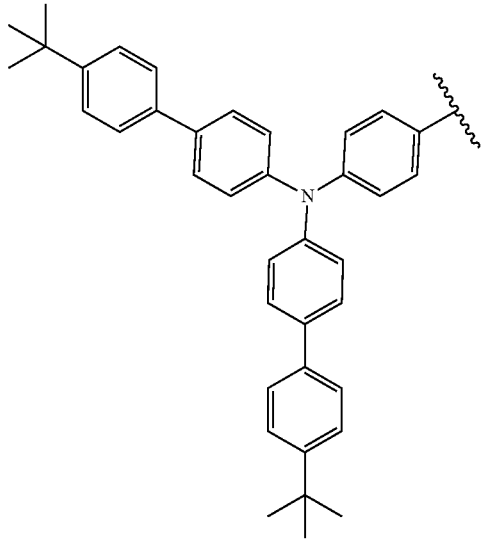 [SMILES: *c1ccc(N(c2ccc(-c3ccc(C(C)(C)C)cc3)cc2)c2ccc(-c3ccc(C(C)(C)C)cc3)cc2)cc1] 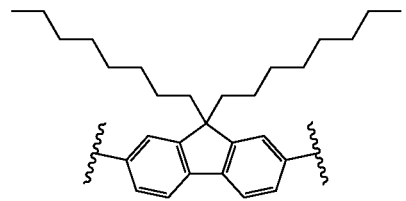 [SMILES: *c1ccc2c(c1)C(CCCCCCCC)(CCCCCCCC)c1cc(*)ccc1-2]
D17 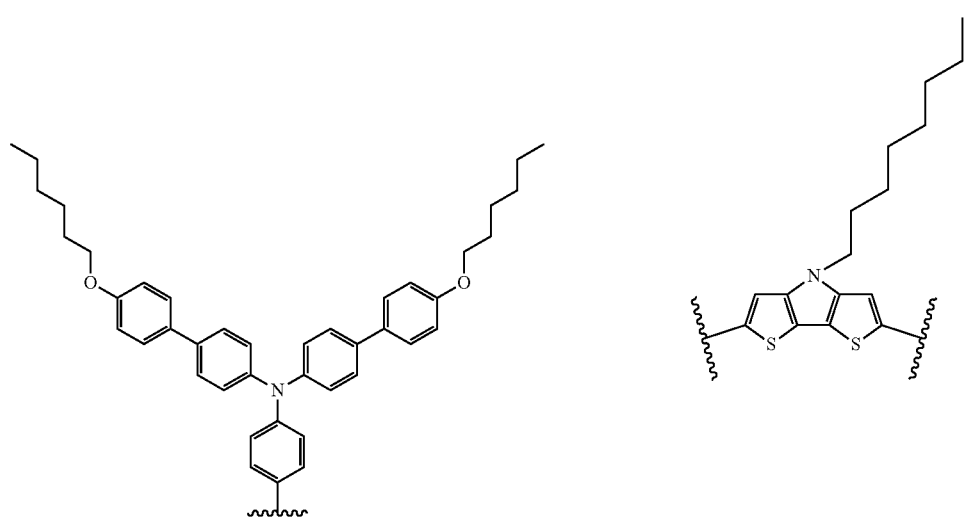
D18 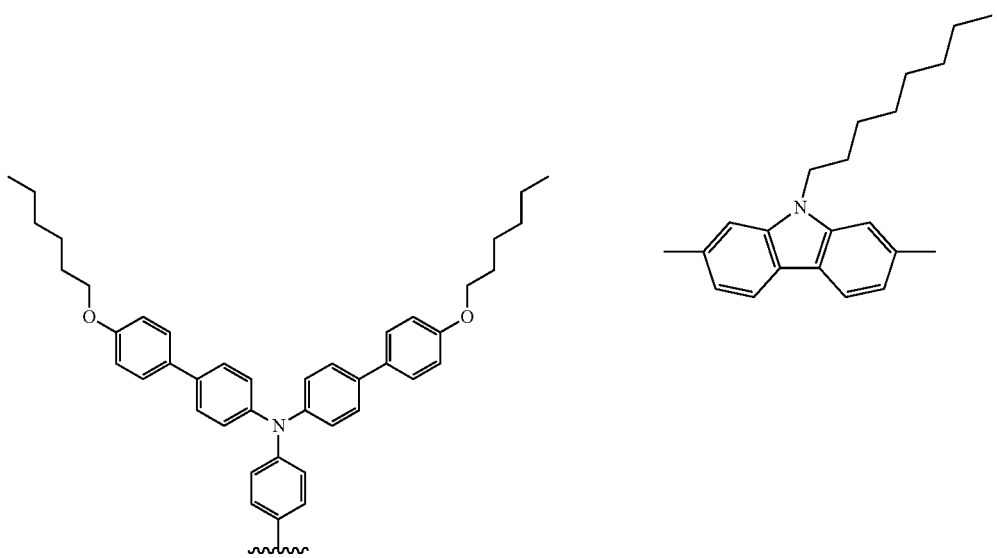

-continued
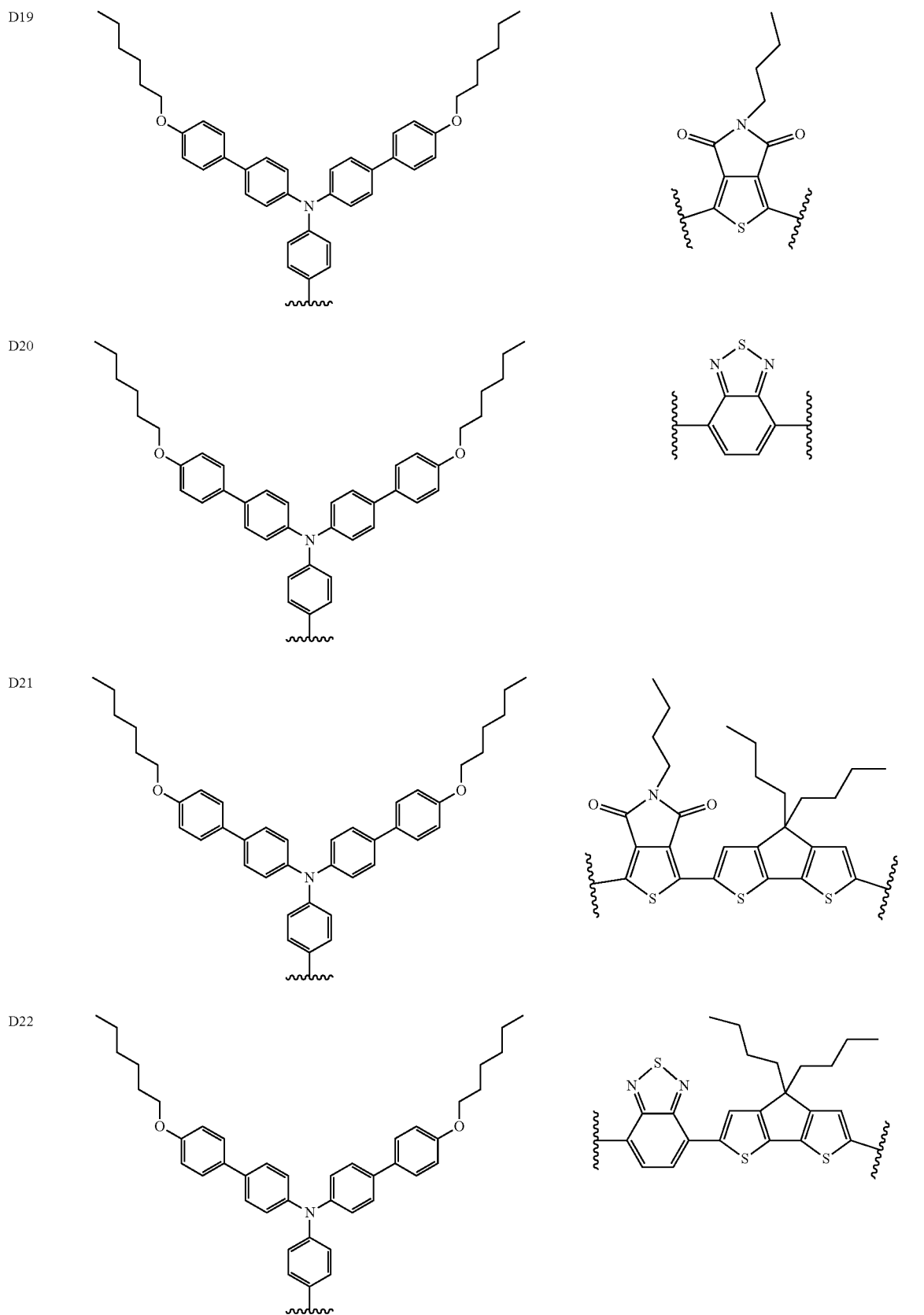

-continued
D23 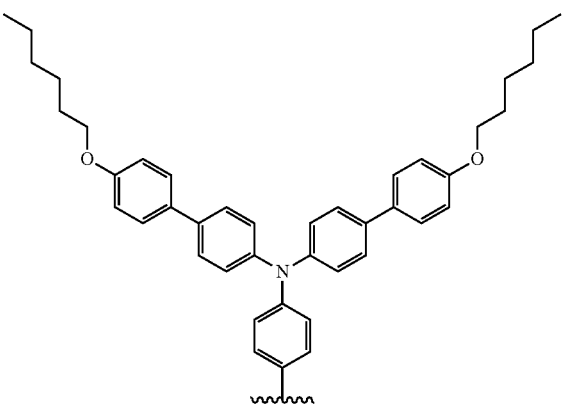 [SMILES: *c1ccc(N(c2ccc(-c3ccc(OCCCCCC)cc3)cc2)c2ccc(-c3ccc(OCCCCCC)cc3)cc2)cc1]
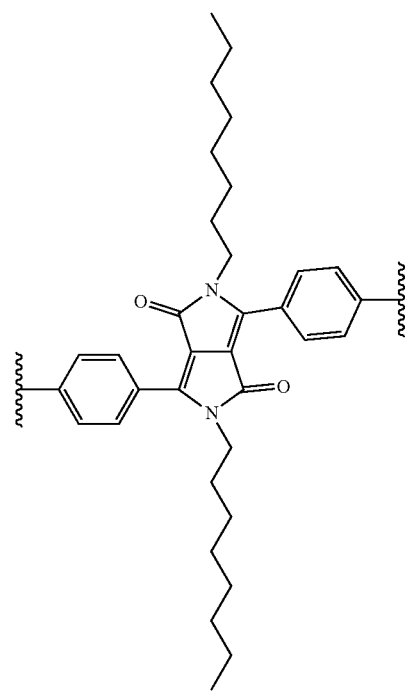 [SMILES: *c1ccc(C2=C3C(=O)N(CCCCCCCC)C(c4ccc(*)cc4)=C3C(=O)N2CCCCCCCC)cc1]
D24 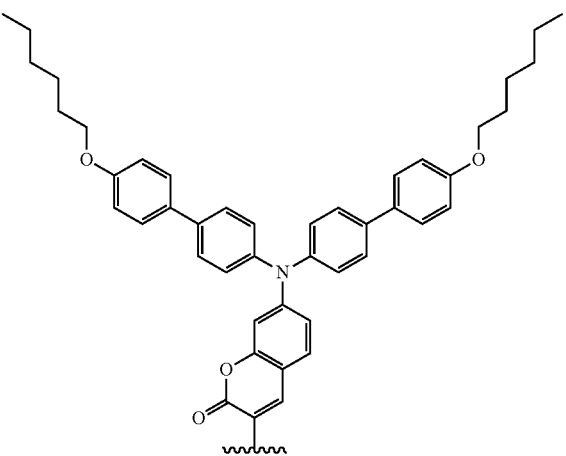 [SMILES: *c1cc2ccc(N(c3ccc(-c4ccc(OCCCCCC)cc4)cc3)c3ccc(-c4ccc(OCCCCCC)cc4)cc3)cc2oc1=O]
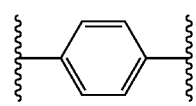
D25G
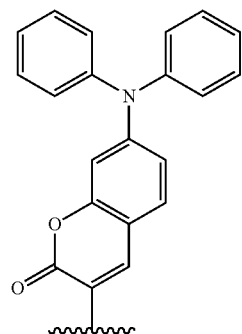 [SMILES: *c1cc2ccc(N(c3ccccc3)c3ccccc3)cc2oc1=O]
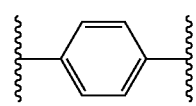

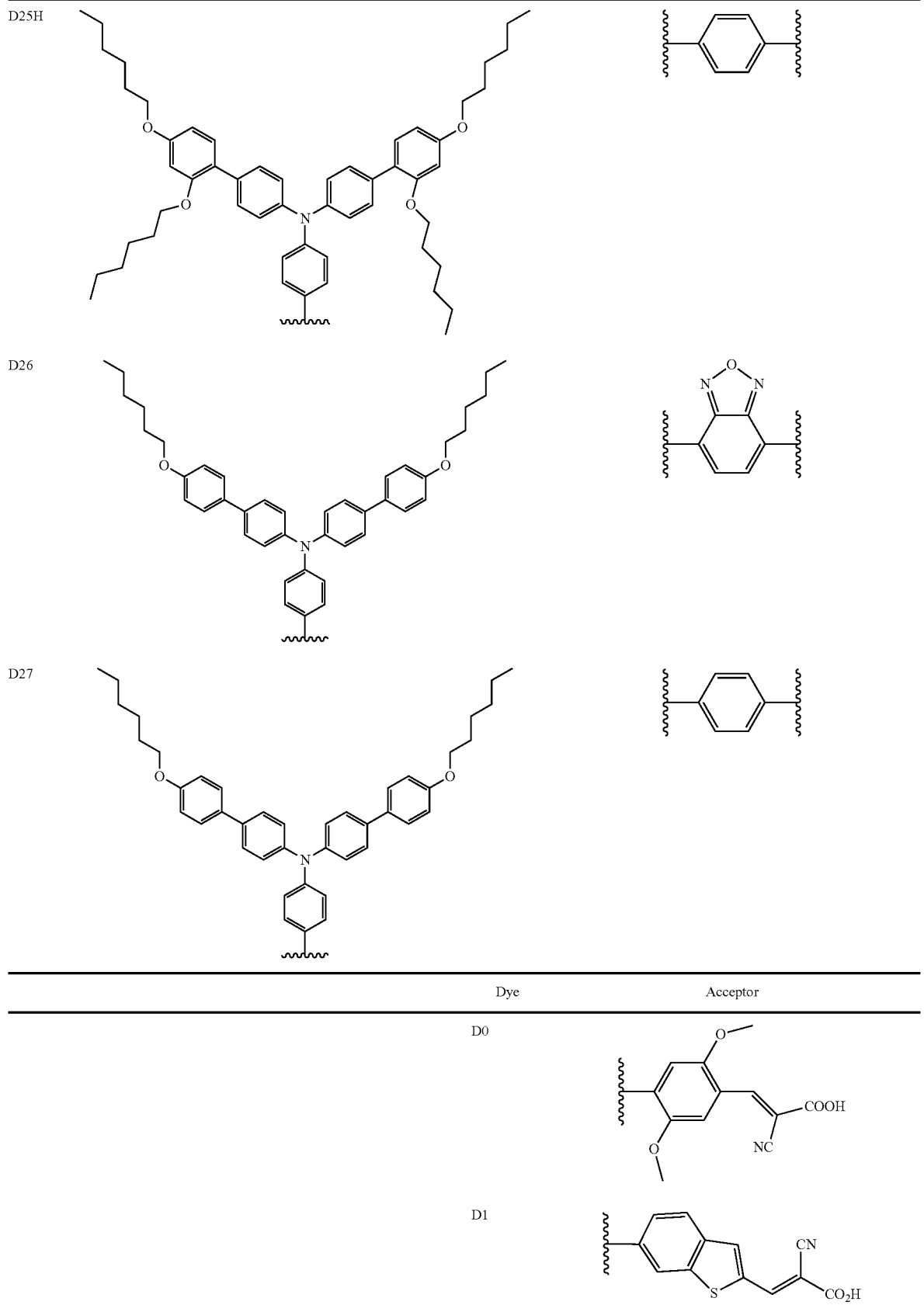

-continued
D2 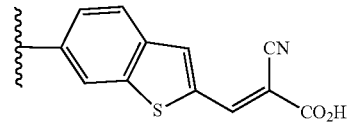 [SMILES: *c1ccc2cc(/C=C(\C#N)C(=O)O)sc2c1]
D3 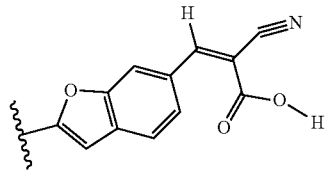 [SMILES: *c1cc2ccc(/C=C(/C#N)C(=O)O)cc2o1]
D4 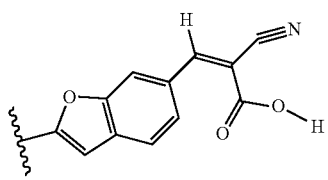 [SMILES: *c1cc2ccc(/C=C(/C#N)C(=O)O)cc2o1]
D5 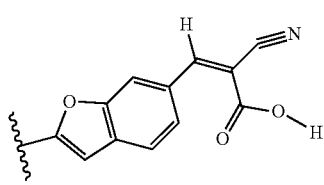 [SMILES: *c1cc2ccc(/C=C(/C#N)C(=O)O)cc2o1]
D6 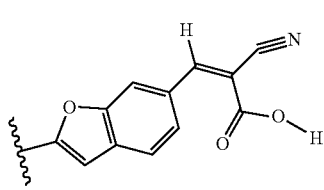 [SMILES: *c1cc2ccc(/C=C(/C#N)C(=O)O)cc2o1]
D7 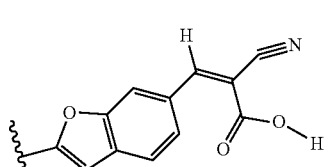
D8 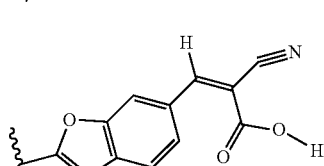
D9 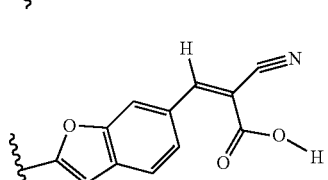
D10 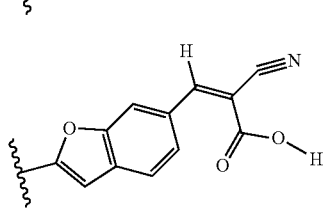

-continued
D11 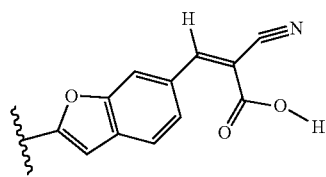 [SMILES: *c1cc2ccc(/C=C(/C#N)C(=O)O)cc2o1]
D12 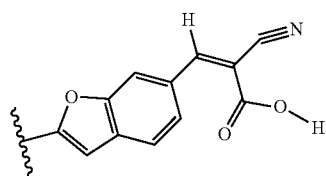 [SMILES: *c1cc2ccc(/C=C(/C#N)C(=O)O)cc2o1]
D13 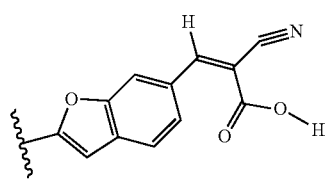 [SMILES: *c1cc2ccc(/C=C(/C#N)C(=O)O)cc2o1]
D14 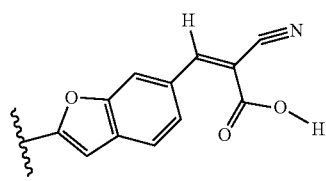 [SMILES: *c1cc2ccc(/C=C(/C#N)C(=O)O)cc2o1]
D15 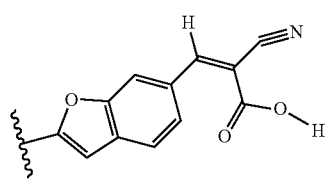 [SMILES: *c1cc2ccc(/C=C(/C#N)C(=O)O)cc2o1]
D16 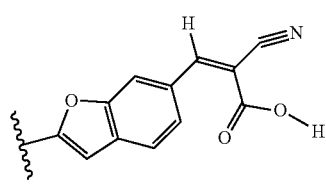 [SMILES: *c1cc2ccc(/C=C(/C#N)C(=O)O)cc2o1]
D17 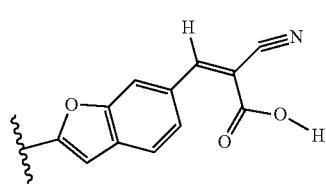 [SMILES: *c1cc2ccc(/C=C(/C#N)C(=O)O)cc2o1]
D18 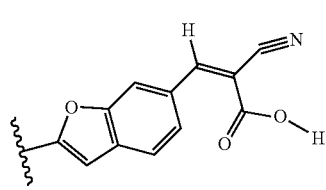 [SMILES: *c1cc2ccc(/C=C(/C#N)C(=O)O)cc2o1]

-continued
D19 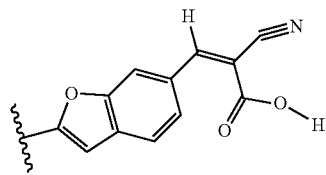 [SMILES: *c1cc2ccc(/C=C(/C#N)C(=O)O)cc2o1]
D20 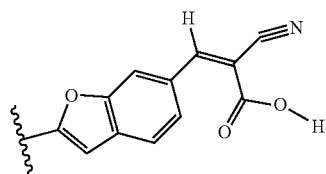 [SMILES: *c1cc2ccc(/C=C(/C#N)C(=O)O)cc2o1]
D21 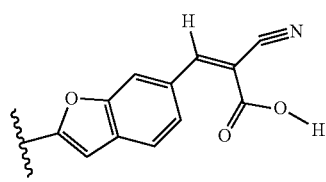 [SMILES: *c1cc2ccc(/C=C(/C#N)C(=O)O)cc2o1]
D22 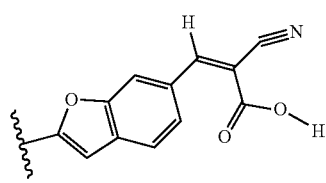 [SMILES: *c1cc2ccc(/C=C(/C#N)C(=O)O)cc2o1]
D23 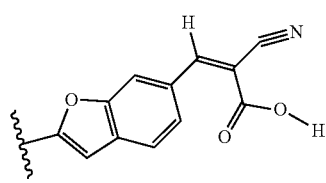 [SMILES: *c1cc2ccc(/C=C(/C#N)C(=O)O)cc2o1]
D24 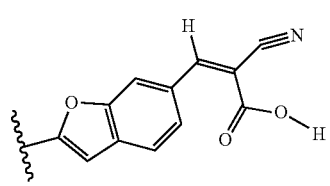 [SMILES: *c1cc2ccc(/C=C(/C#N)C(=O)O)cc2o1]
D25G 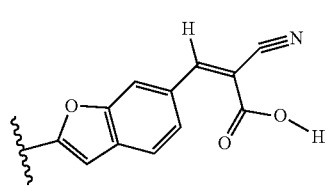 [SMILES: *c1cc2ccc(/C=C(/C#N)C(=O)O)cc2o1]
D25H 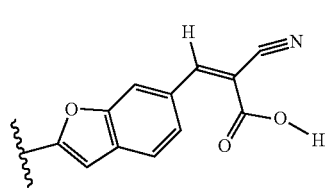 [SMILES: *c1cc2ccc(/C=C(/C#N)C(=O)O)cc2o1]

-continued

D26

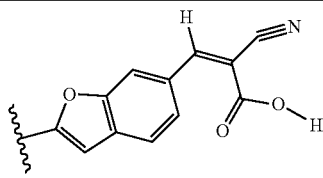

D27

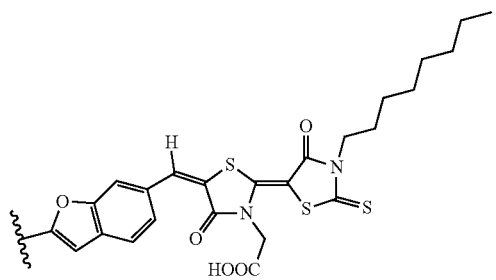 [SMILES: *c1cc2ccc(/C=c3/s/c(=C4/SC(=S)N(CCCCCCCC)C4=O)n(CC(=O)O)c3=O)cc2o1]

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein. However, other equivalent separation or isolation procedures can also be used.

When desired, the (R)- and (S)-isomers of the solar cell dyes described herein, if present, may be resolved by methods known to those skilled in the art, for example by formation of diastereomeric salts or complexes which may be separated, for example, by crystallization; via formation of diastereomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The solar cell dyes described herein can be optionally contacted with an acceptable acid to form the corresponding acid addition salts. Acceptable forms of the solar cell dyes recited herein include salts, chelates, non-covalent complexes or derivatives, precursors, and mixtures thereof. In certain embodiments, the dyes described herein are in the form of salts. In addition, if the dye described herein is obtained as an acid addition salt, the free base can be obtained by basifying a solution of the acid salt. Conversely, if the product is a free base, an addition salt may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic addition salts.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") include those embodiments, for example, an embodiment of any composition of matter, composition, method, or process, or the like, that "consist of" or "consist essentially of" the described features.

Non-Benzofuran-Containing Dyes

Non-benzofuran-containing dyes as described herein are any dyes that (a) are useful in DSSCs and (b) do not contain a benzofuran ring in their structure. There are currently many commercially available non-benzofuran containing dyes.

In some embodiments, the non-benzofuran containing dye is selected from the group consisting of MK2, BOD4, XY1b, WE10 and WE11. The first three of these dyes are commercially available and have the following structures:

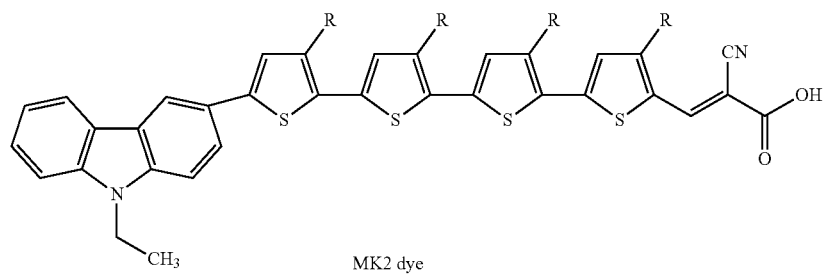
MK2 dye
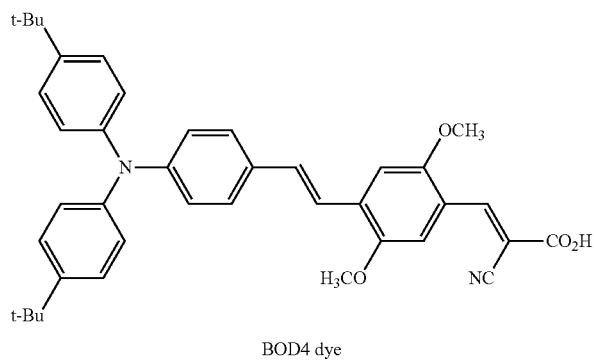
BOD4 dye
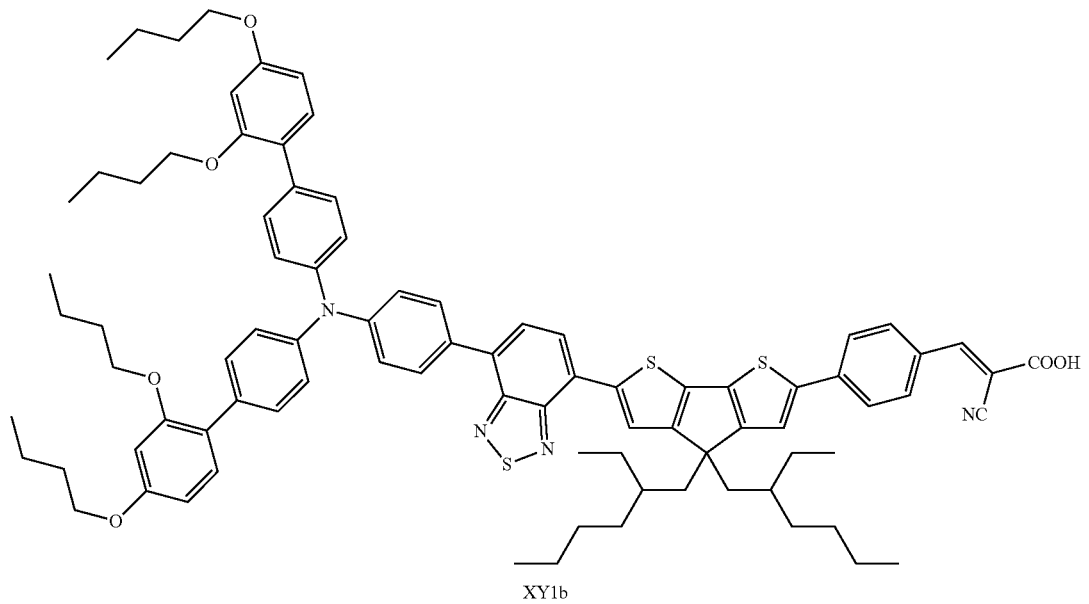
XY1b
Rs* = CH$_2$(CH$_2$)$_4$CH$_3$ The latter two dyes have the following structures:
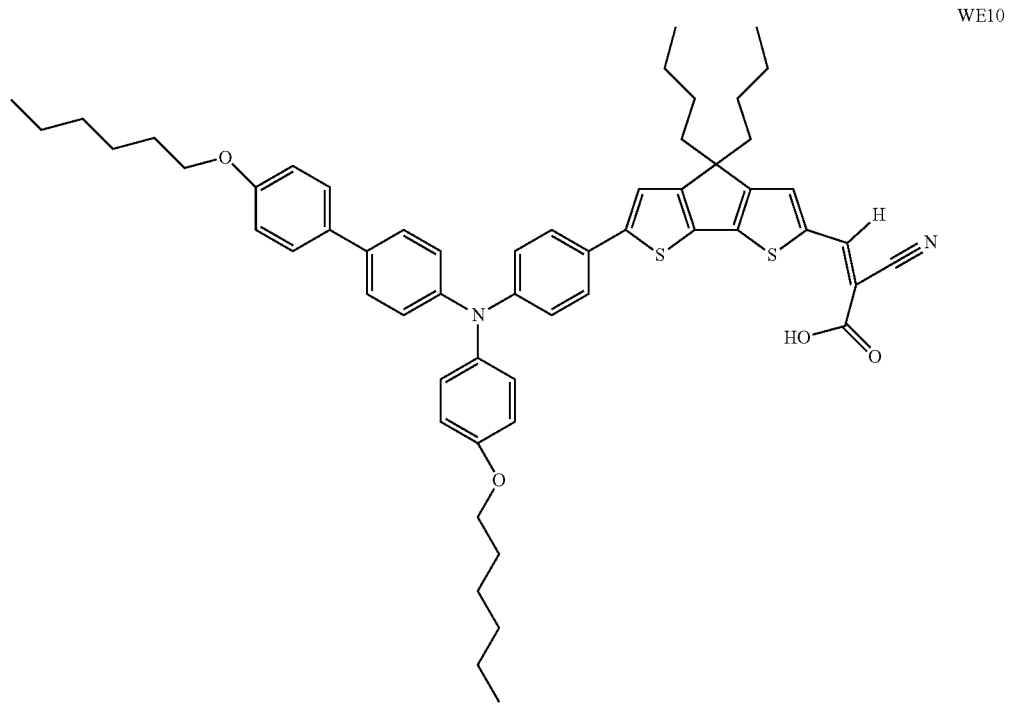
WE10
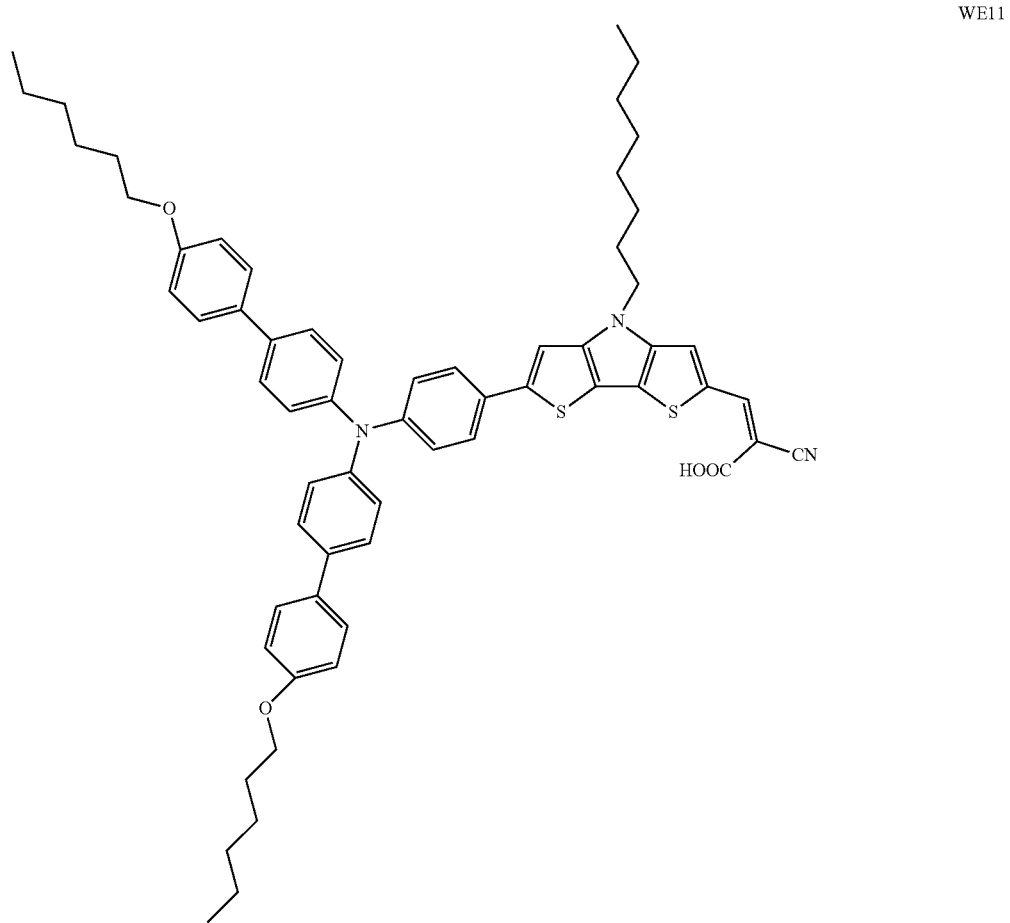
WE11

Combinations of Solar Cell Dyes

Solar cell dye combinations described herein comprise a benzofuran-containing dye and a non-benzofuran-containing dye. In some embodiments, the benzofuran-containing dye is a compound having the structure shown in formulae I, II, III or IV as shown herein. In some embodiments, the non-benzofuran-containing dye is MK2, BOD4, XY1b, WE10 or WE11.

EXPERIMENTAL

All reagents were purchased from commercial suppliers and used as supplied unless stated otherwise. Reactions were carried out in air unless stated otherwise. 400 MHz 1H NMR spectra were obtained on a JEOL AS 400 spectrometer. Low-resolution mass spectra (LRMS) were obtained on a JEOL JMS-T100LC DART/AccuTOF mass spectrometer. Measurement of reversal of protein aggregation may be carried out using such assays as Bis-ANS Fluorescence as described in, for example, W. T. Chen et al. (2011), *J. Biol. Chem*, 286 (11): 9646.

Synthesis of Solar Cell Dyes

Example 1. Synthesis of (Z)-2-cyano-3-[6-[5-[4-[4-(4-hexoxyphenyl)-N-[4-(4-hexoxyphenyl)-phenyl]anilino]phenyl]-3-hexyl-2-thienyl]benzothiophen-2-yl]prop-2-enoic acid (D1)

A. 4,4'-Bis(4-n-hexyloxyphenyl)triphenylamine

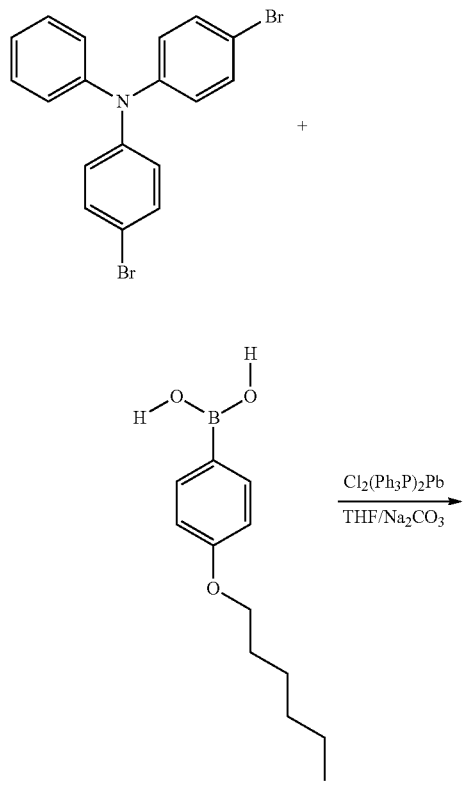

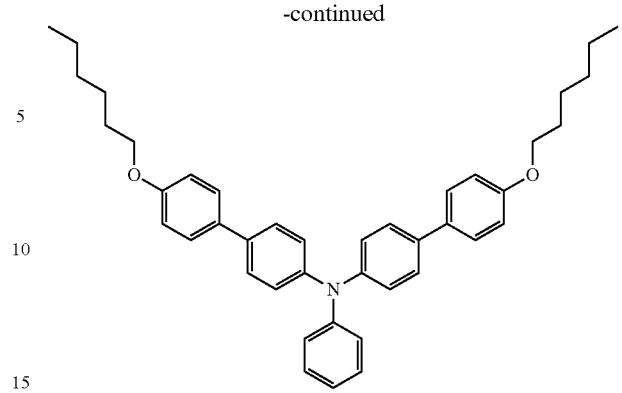

In a round bottom flask, 6.0 g (14.9 mmol) dibromotriphenylamine, 8.9 g (38.2 mmol) 4-n-hexyloxybenzeneboronic acid and 0.2 g (0.25 mmol) dichloro-bis(diphenylphosphino) ferrocene palladium (II) was combined in 50 mL THF and 30 mL 10% $Na_2CO_3$. The batch was held at reflux for 24 h and HPLC showed complete reaction. Mixture was poured into a beaker with 300 mL water and the product was filtered off, washed with water, and dried. Crude product was dissolved in methylene chloride then passed through a plug of silica gel and washed through with dichloromethane. The solvent was removed and replaced with acetonitrile. The resulting solid was filtered off, washed with acetonitrile and dried, yielding 8 g tan solid (90% yield). UV/Vis max 325 nm, LCMS m/z=598.4.

B. N-(4-bromophenyl)-4-(4-hexoxyphenyl)-N-[4-(4-hexoxyphenyl)-phenyl]aniline

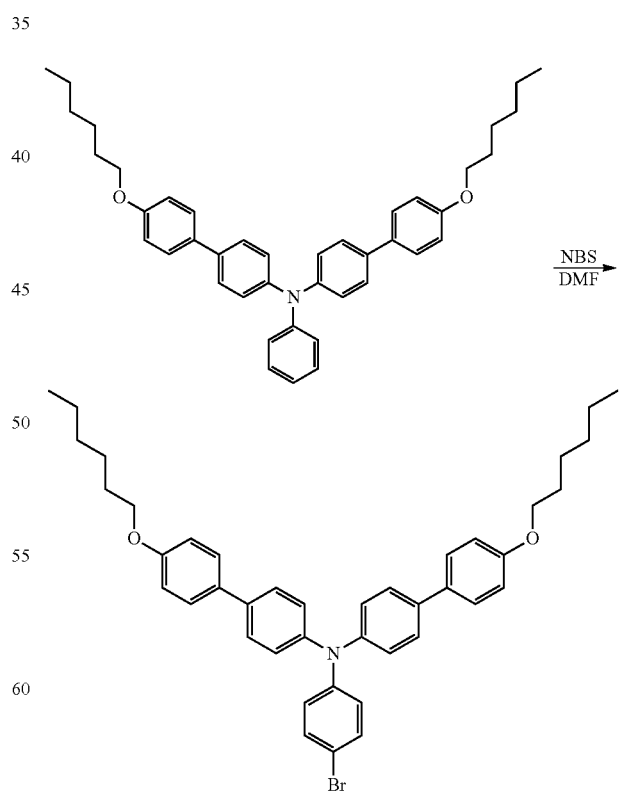

In a round bottom flask, 4.25 g (7.1 mmol) 4,4'-Bis(4-n-hexyloxyphenyl)triphenylamine and 1.5 g (8.4 mmol)

N-bromosuccinimide was combined in 45 mL DMF at 25° C. for 2 h. Mixture was poured into a beaker with 300 mL water and the product was extracted into dichloromethane. The organic layer was dried over Na$_2$SO$_4$, evaporated to dryness and the residue was crystallized from ethanol, yielding 3.55 g white solid (5.25 mmol, 73.9% yield). UV/Vis max 330 nm, LCMS m/z=678.2.

C. N,N-bis[4-(4-hexoxyphenyl)phenyl]-4-(4,4,5,5-tetramethyl-1,3,2-dioxaborolan-2-yl)aniline

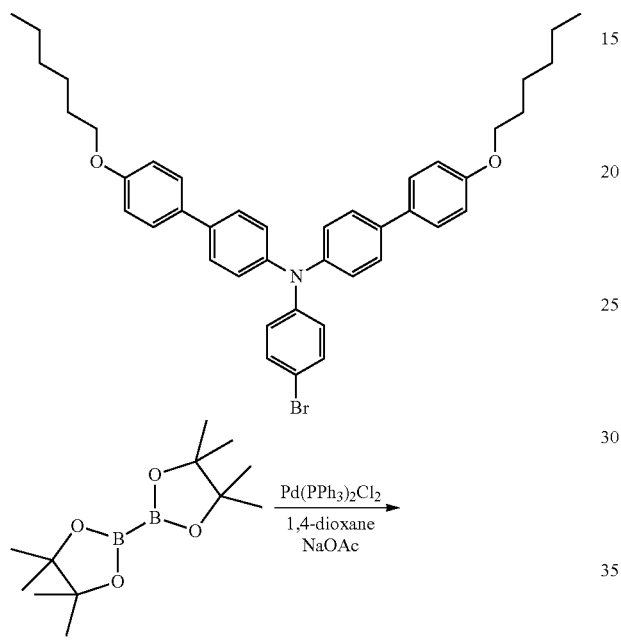

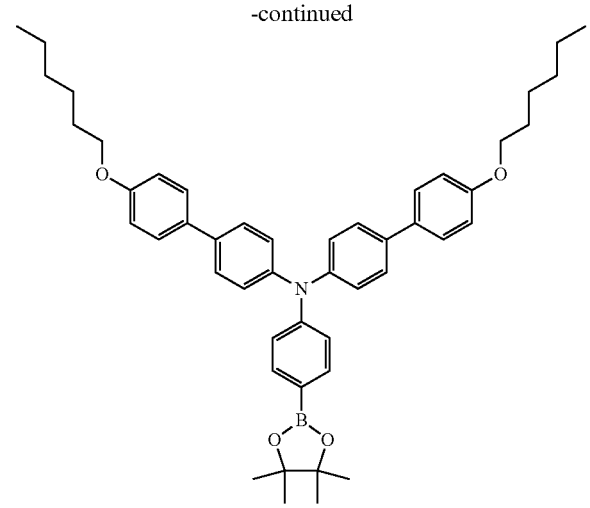

In a round bottom flask, 7.7 g (11.38 mmol) N-(4-bromophenyl)-4-(4-hexoxyphenyl)-N-[4-(4-hexoxyphenyl)phenyl]aniline, 3.6 g (17.07 mmol) bis(pinacolato)diborane and 4 g KOAc was combined in 80 mL 1,4-dioxane. 0.3 g (0.4 mmol) dichloro 1,1'-bis(diphenylphosphino)ferrocene palladium(II) was added and the batch was held at reflux for 2 h. Reaction completed. Batch was cooled to rt then poured into 400 mL of water. Solid was filtered off, washed with water and dried. Solid was dissolved in methylene chloride and passed through a silica gel plug and washed through with methylene chloride to remove original material. Solvent was displaced with ethyl acetate causing the product to crystalize, yielding 5.46 g white solid (7.54 mmol, 66% yield). UV/Vis max 335 nm, LCMS m/z=724.4

D. Methyl 6-[5-[4-[4-(4-hexoxyphenyl)-N-[4-(4-hexoxyphenyl)-phenyl]anilino]phenyl]-3-methyl-2-thienyl]benzothiophene-2-carboxylate

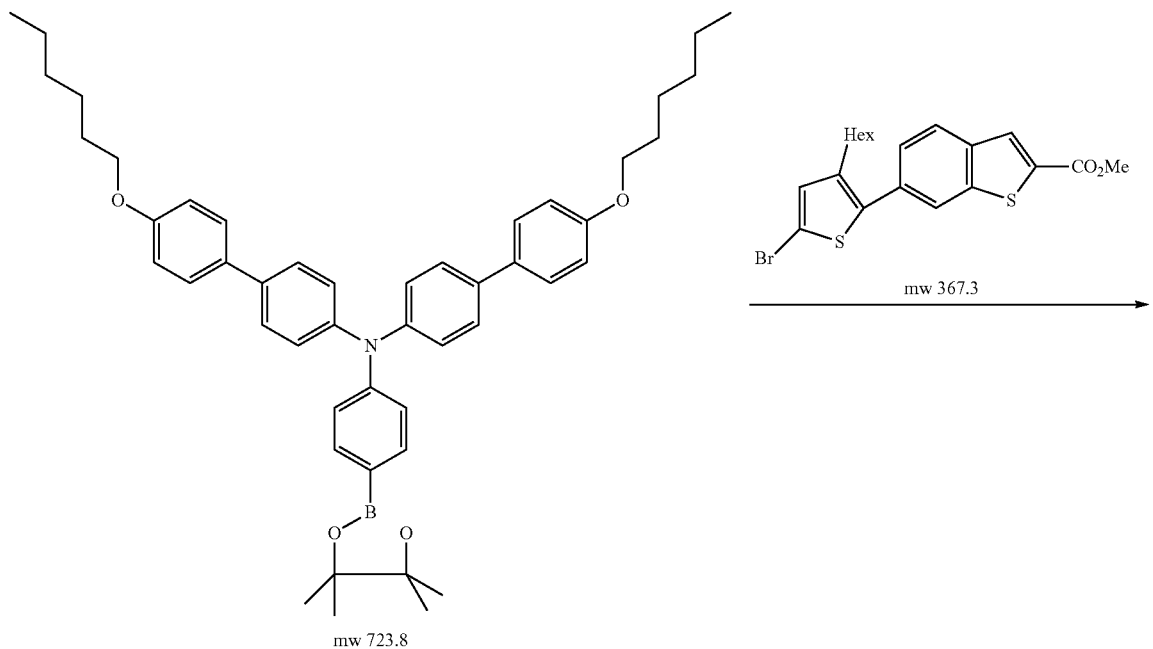

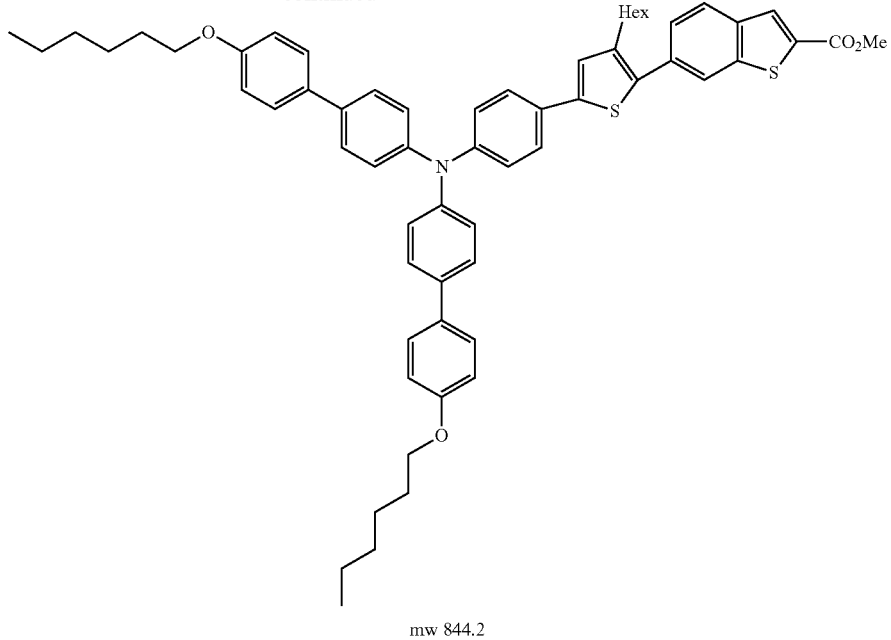

mw 844.2

In a round bottom flask, 1 g (1.38 mmol) N,N-bis[4-(4-hexoxyphenyl)phenyl]-4-(4,4,5,5-tetramethyl-1,3,2-dioxaborolan-2-yl)aniline, 0.56 g (1.5 mmol) methyl 6-(5-bromo-3-methyl-2-thienyl)benzothiophene-2-carboxylate was combined in 20 mL THF and 3 mL 10% $Na_2CO_3$ (0.44 g dry, 4.2 mmol). 0.1 g (0.13 mmol) dichloro-bis(diphenylphosphino) ferrocene palladium (II) was added and the batch was refluxed for 2 h. HPLC (C18, 10% up to 80% THF/water) indicated complete reaction. Batch was poured into 100 mL water and product was extracted into dichloromethane. Product was purified using chromatography (EtOAc/Hexane) yielding 250 mg yellow solid (21% yield).

E. [6-[5-[4-[4-(4-hexoxyphenyl)-N-[4-(4-hexoxyphenyl)-phenyl]anilino]phenyl]-3-methyl-2-thienyl]benzothiophen-2-yl]methanol

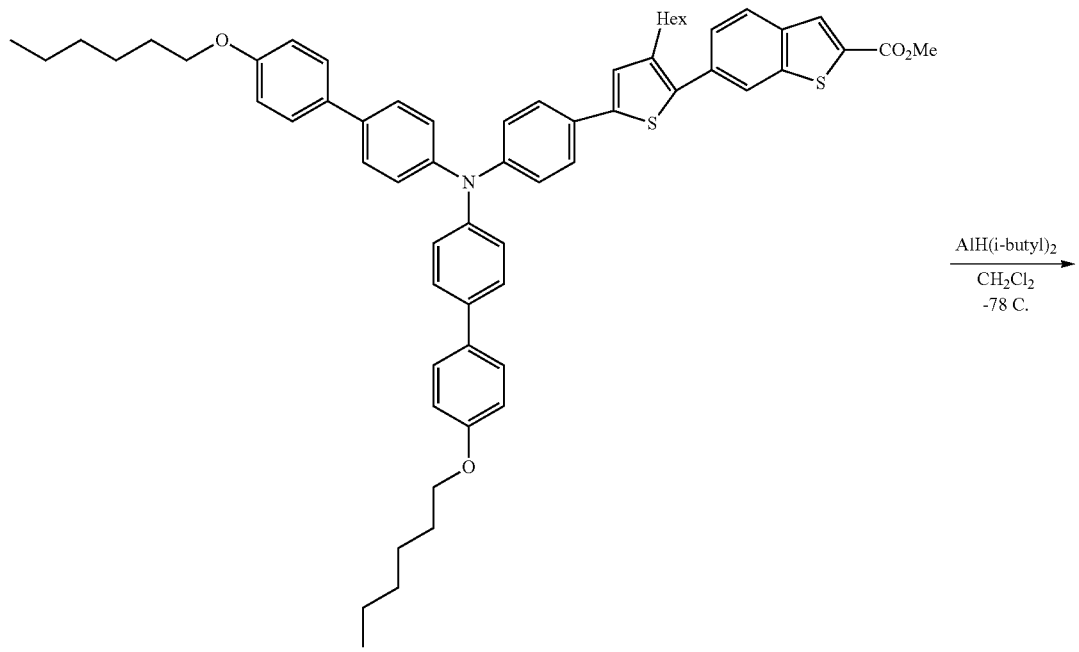

-continued

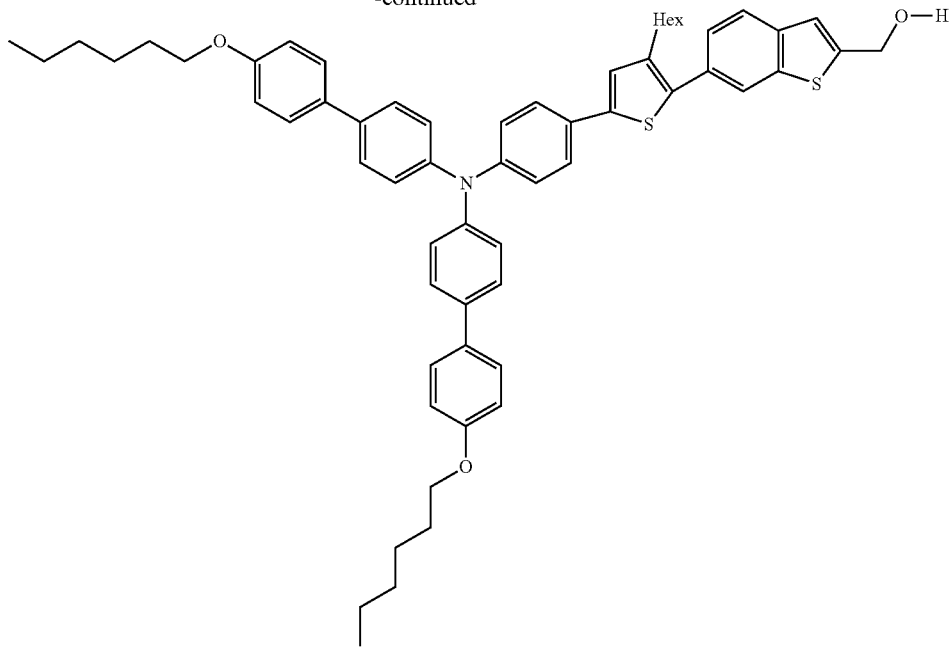

In a round bottom flask, 0.3 g (0.31 mmol) methyl 6-[5-[4-[4-(4-hexoxyphenyl)-N-[4-(4-hexoxyphenyl)phenyl]anilino]phenyl]-3-methyl-2-thienyl]benzothiophene-2-carboxylate in 10 mL methylene chloride was cooled to −78 C. 0.35 mL (0.35 mmol) DIBAL (1M in hexane) was added dropwise. After 3 h, reaction stalled at ~60% completion. 0.2 mL additional DIBAL was added. Reaction was completed in ~15 min. 5 mL ethyl acetate was slowly added, along with 200 mg of water. Batch was allowed to warm to rt overnight. Product was purified on silica gel (hexane/methylene chloride) yielding 0.257 g (0.28 mmol, 90% yield).

F. 6-[5-[4-[4-(4-hexoxyphenyl)-N-[4-(4-hexoxyphenyl)-phenyl]anilino]phenyl]-3-hexyl-2-thienyl]benzothiophene-2-carbaldehyde

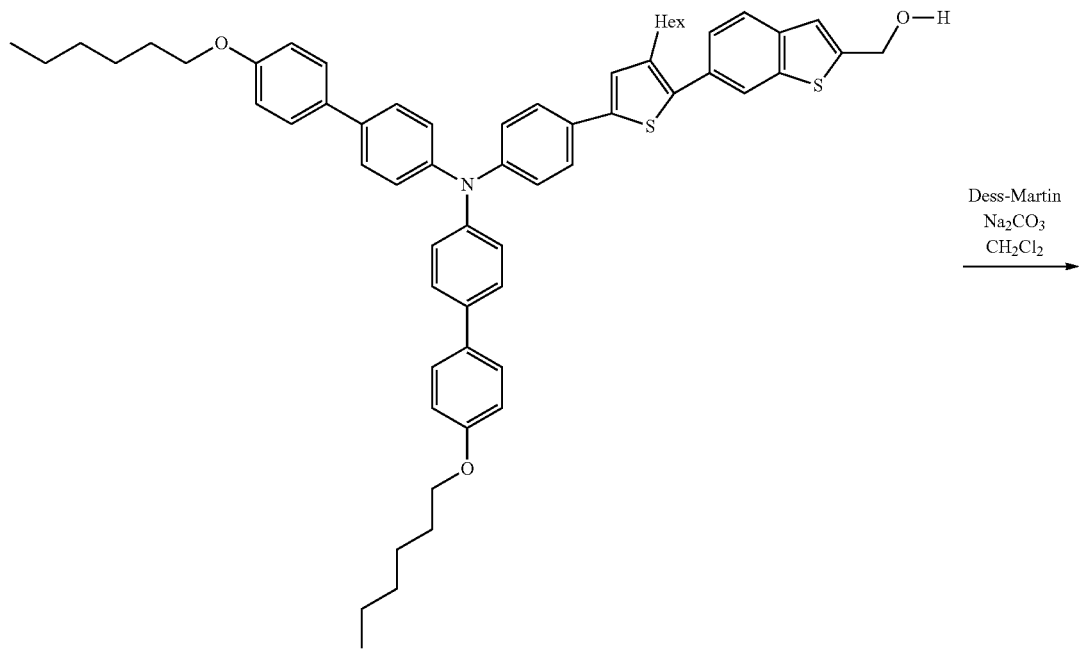

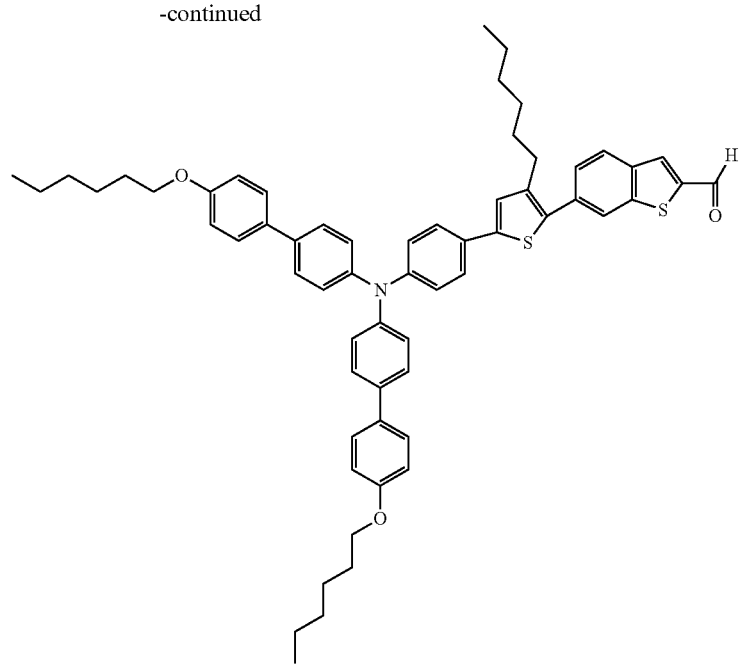

In a round bottom flask, 0.257 g (0.28 mmol) [6-[5-[4-[4-(4-hexoxyphenyl)-N-[4-(4-hexoxyphenyl)phenyl]anilino]phenyl]-3-methyl-2-thienyl]benzothiophen-2-yl] methanol was dissolved in 10 mL methylene chloride. 0.3 g (2.8 mmol) $Na_2CO_3$ and 0.14 g (0.33 mmol) Dess-Martin reagent was added. HPLC showed ~60% conversion to a new material. An additional 0.1 g was added, causing the reaction to go to completion. Product was purified on silica gel (hexane/methylene chloride), yielding 0.257 g (0.28 mmol, 100% yield).

G. (Z)-2-cyano-3-[6-[5-[4-[4-(4-hexoxyphenyl)-N-[4-(4-hexoxyphenyl)-phenyl]anilino]phenyl]-3-hexyl-2-thienyl]benzothiophen-2-yl]prop-2-enoic acid (D1)

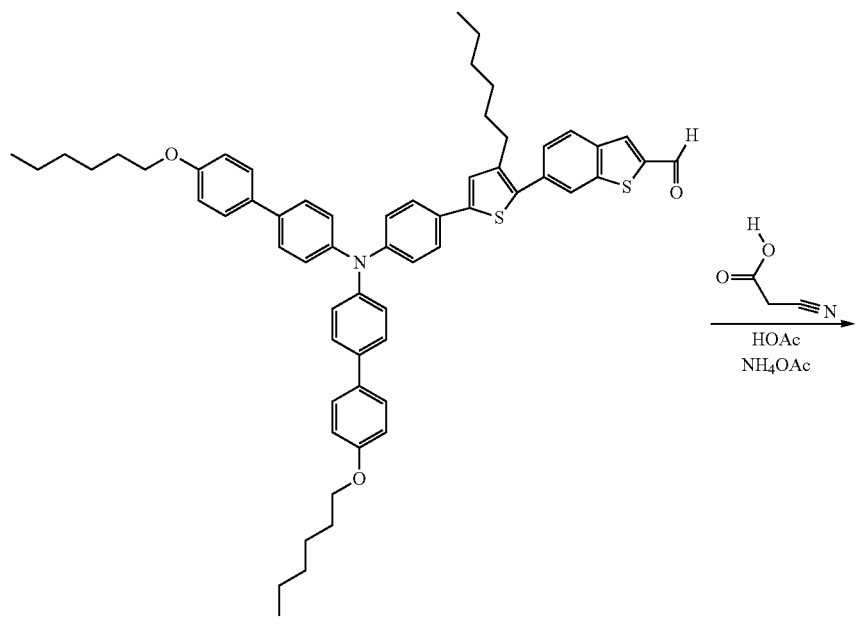

-continued

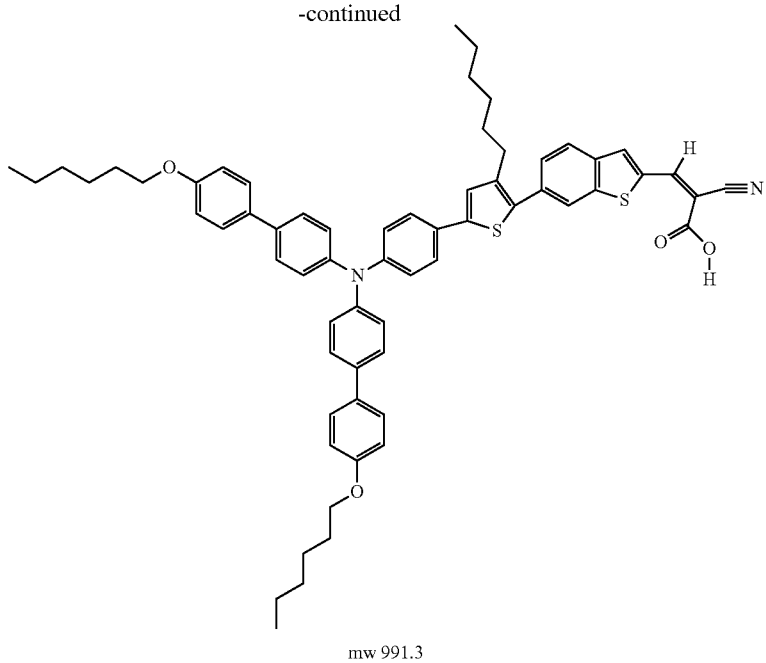

mw 991.3

In a round bottom flask, 0.242 g (0.26 mmol) 6-[5-[4-[4-(4-hexoxyphenyl)-N-[4-(4-hexoxyphenyl)phenyl]anilino]phenyl]-3-hexyl-2-thienyl]benzothiophene-2-carbaldehyde, 0.067 g (0.79 mmol) cyanoacetic acid and 0.13 g (1.68 mmol) ammonium acetate was combined in 10 mL HOAc at reflux for 8 h. HPLC indicated complete reaction. Product was oiled out upon cooling. HOAc layer was removed and the product (still in rb-flask) was vacuum dried to remove residual HOAc. Crude product was dissolved in ~6 mL methylene chloride and passed through a plug of silica gel and eluted with ~50 mL methylene chloride (product remains on the plug). The product was washed off the silica using 30% MeOH in $CH_2Cl_2$. Solvent was stripped off and product was vacuum dried yielding 0.142 g (55% yield).

Example 2. Synthesis of (Z)-3-[2-[4-[4-[4-(4-tert-butylphenyl)-N-[4-(4-tert-butylphenyl)-phenyl]anilino]phenyl]phenyl]benzofuran-6-yl]-2-cyano-prop-2-enoic acid (D5)

A. 4,4'-Bis(4-t-butylphenyl)triphenylamine

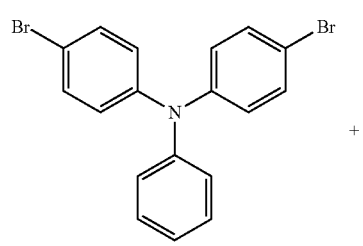

+

-continued

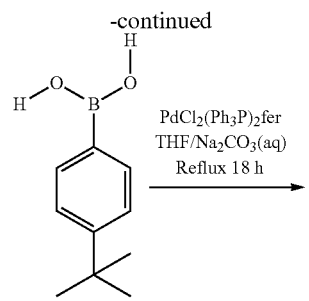

PdCl$_2$(Ph$_3$P)$_2$fer
THF/Na$_2$CO$_3$(aq)
Reflux 18 h

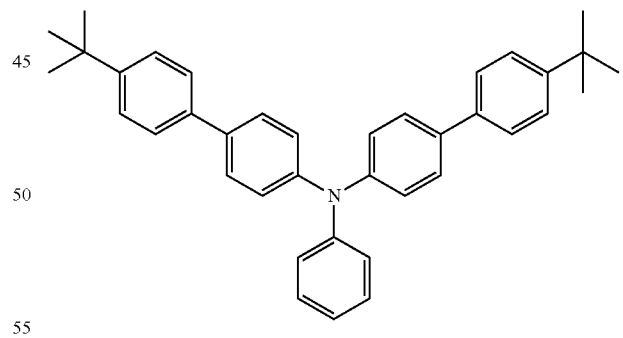

In a round bottom flask, 5.25 g (13 mmol) 4,4'-Dibromotriphenylamine, 5.8 g (32.5 mmol) 4-t-butyl-phenylboronic acid, 0.2 g (0.26 mmol) dichloro-bis(diphenylphosphino) ferrocene palladium (II) was combined in 80 mL THF and 20 mL 10% Na$_2$CO$_3$. Batch was held at reflux for 18 h (LC showed complete reaction). Reaction mixture was poured into 300 mL water and extracted product into methylene chloride. The organic layer was dried, then passed through a bed of silica gel. The solvent was stripped off and replaced with methanol resulting in a white solid (5.4 g, 81% yield).

B. N-(4-bromophenyl)-4-(4-tert-butylphenyl)-N-[4-(4-tert-butylphenyl)-phenyl]aniline

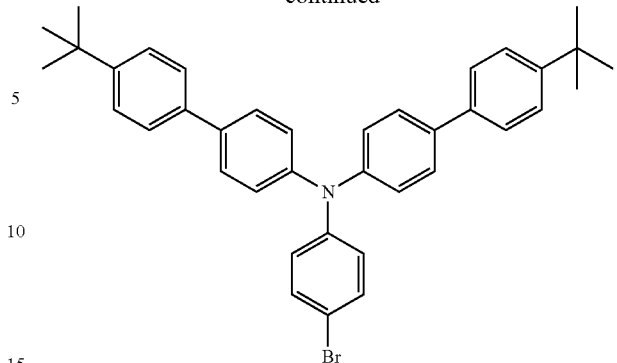

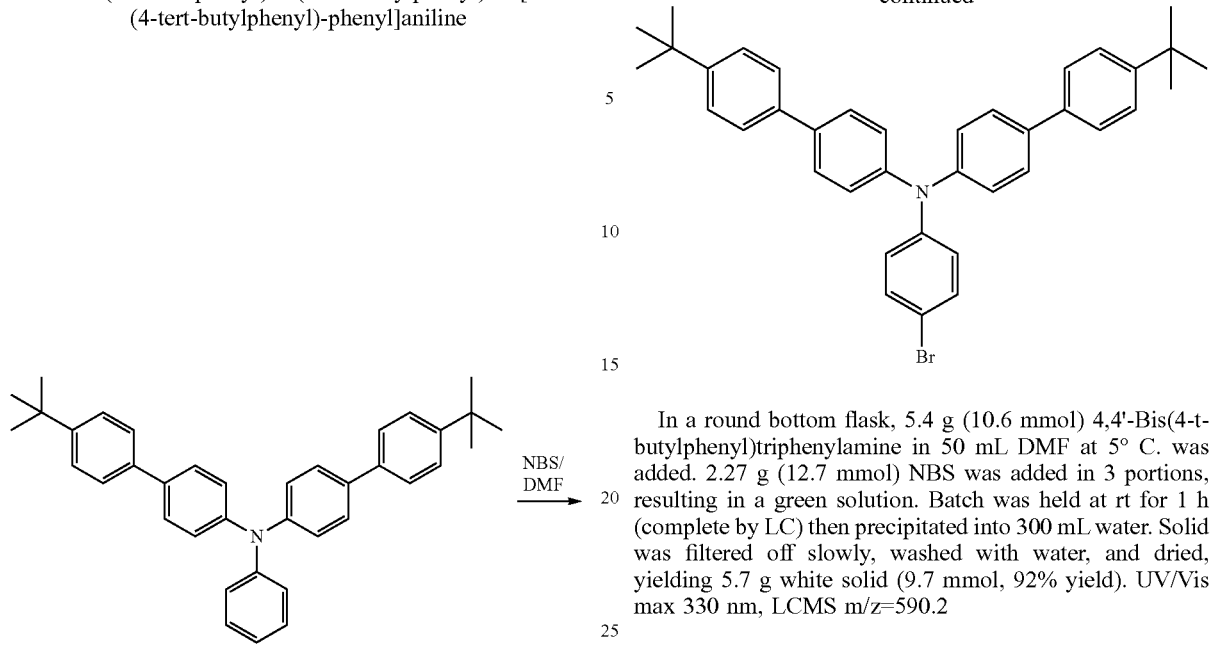

In a round bottom flask, 5.4 g (10.6 mmol) 4,4'-Bis(4-t-butylphenyl)triphenylamine in 50 mL DMF at 5° C. was added. 2.27 g (12.7 mmol) NBS was added in 3 portions, resulting in a green solution. Batch was held at rt for 1 h (complete by LC) then precipitated into 300 mL water. Solid was filtered off slowly, washed with water, and dried, yielding 5.7 g white solid (9.7 mmol, 92% yield). UV/Vis max 330 nm, LCMS m/z=590.2

C. N,N-bis[4-(4-tert-butylphenyl)phenyl]-4-(4,4,5,5-tetramethyl-1,3,2-dioxaborolan-2-yl)aniline

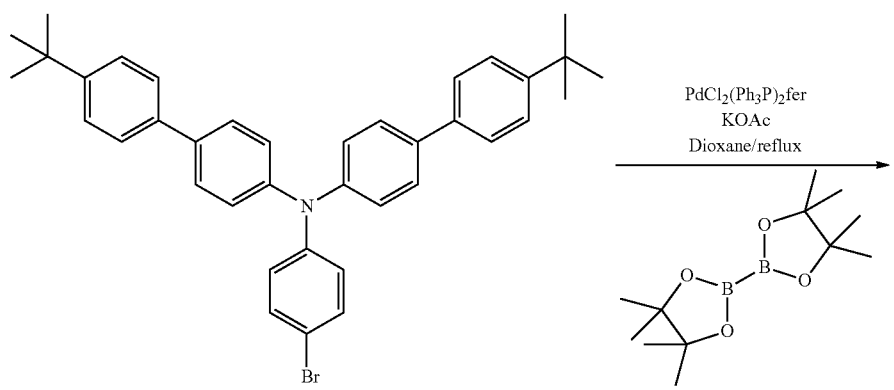

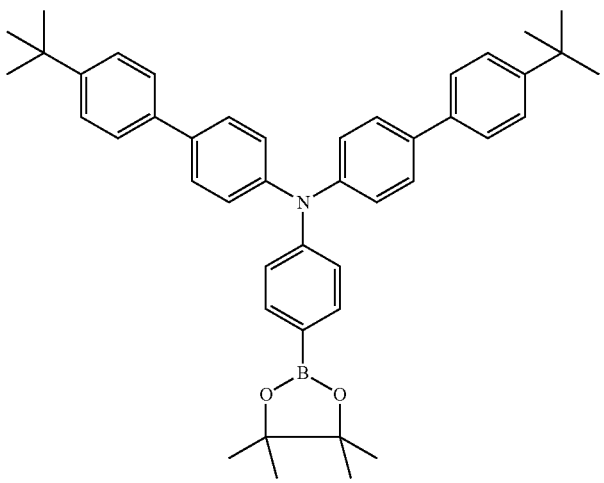

In a round bottom flask, 3 g (5.1 mmol) N-(4-bromophenyl)-4-(4-tert-butylphenyl)-N-[4-(4-tert-butylphenyl)phenyl]aniline, 0.2 g (0.26 mmol) dichloro-bis(diphenylphosphino) ferrocene palladium (II), 1.5 g (5.5 mmol) bis(pinacolato)diborane and 1.6 g KOAc was combined in 30 mL 1,4-dioxane. Batch was held at reflux for 2 h. HPLC indicated a complete reaction. Batch was cooled to rt then poured into 200 mL water. Solid was filtered off, washed with water, then washed with acetonitrile and vacuum dried at 60° C. (3.5 g). Solid dissolved in methylene chloride and passed through a silica gel plug and washed through with methylene chloride to remove origin material. Solvent stripped off and replaced with ethanol. Solid filtered off and washed with ethanol yielding 2.3 g (3.6 mmol, 71% yield). UV/Vis max 335 nm, LCMS m/z=636.4.

D. 2-[4-[4-[4-(4-tert-butylphenyl)-N-[4-(4-tert-butylphenyl)-phenyl]anilino]phenyl]phenyl]benzofuran-6-carbaldehyde

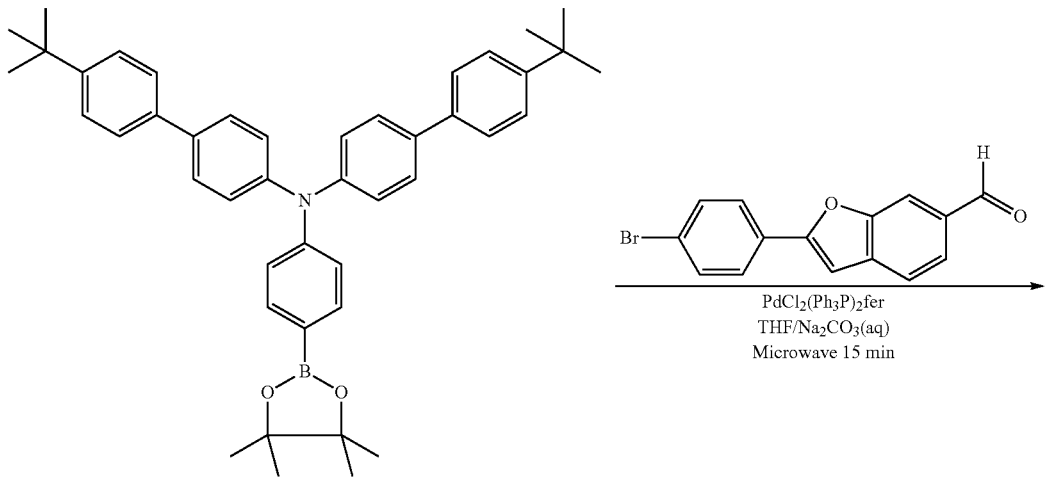

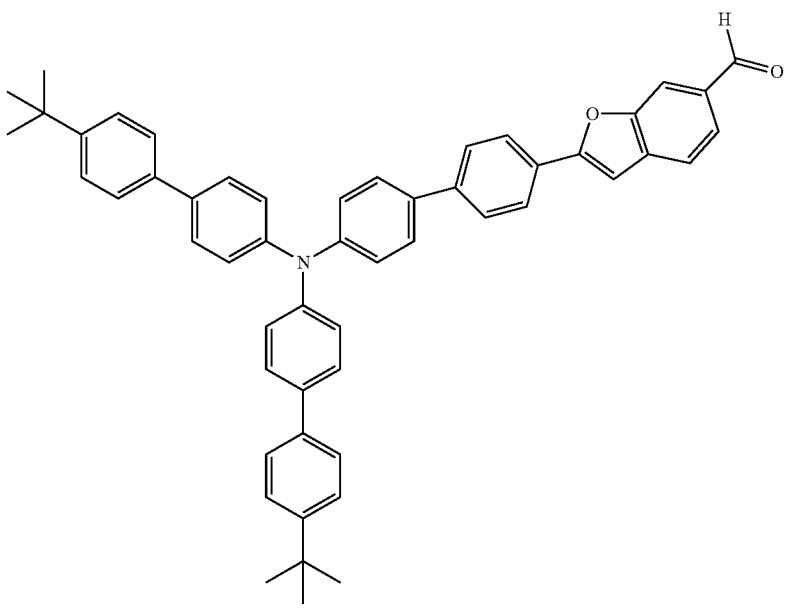

In a round bottom flask, 634 mg (1.0 mmol) N,N-bis[4-(4-tert-butylphenyl)phenyl]-4-(4,4,5,5-tetramethyl-1,3,2-dioxaborolan-2-yl)aniline, 320 mg (1.06 mmol) 2-(4-bromophenyl)benzofuran-6-carbaldehyde and 60 mg (0.08 mmol) dichloro-bis(diphenylphosphino) ferrocene palladium (II) was combined in 8 mL THF and 3 mL 10% $Na_2CO_3$. Batch was microwaved at 100° C. for 15 min. Batch was poured into 100 mL water and product was extracted into methylene chloride. The organic layer was dried, then passed through a silica gel plug. Product was washed through with methylene chloride. Solvent was stripped off and product crystallized from ethanol. 338 mg (0.46 mmol, 46% yield). UV/Vis max 340 nm & 390 nm, LCMS m/z=730.4.

E. (Z)-3-[2-[4-[4-[4-(4-tert-butylphenyl)-N-[4-(4-tert-butylphenyl)-phenyl]anilino]phenyl]phenyl]benzofuran-6-yl]-2-cyano-prop-2-enoic acid

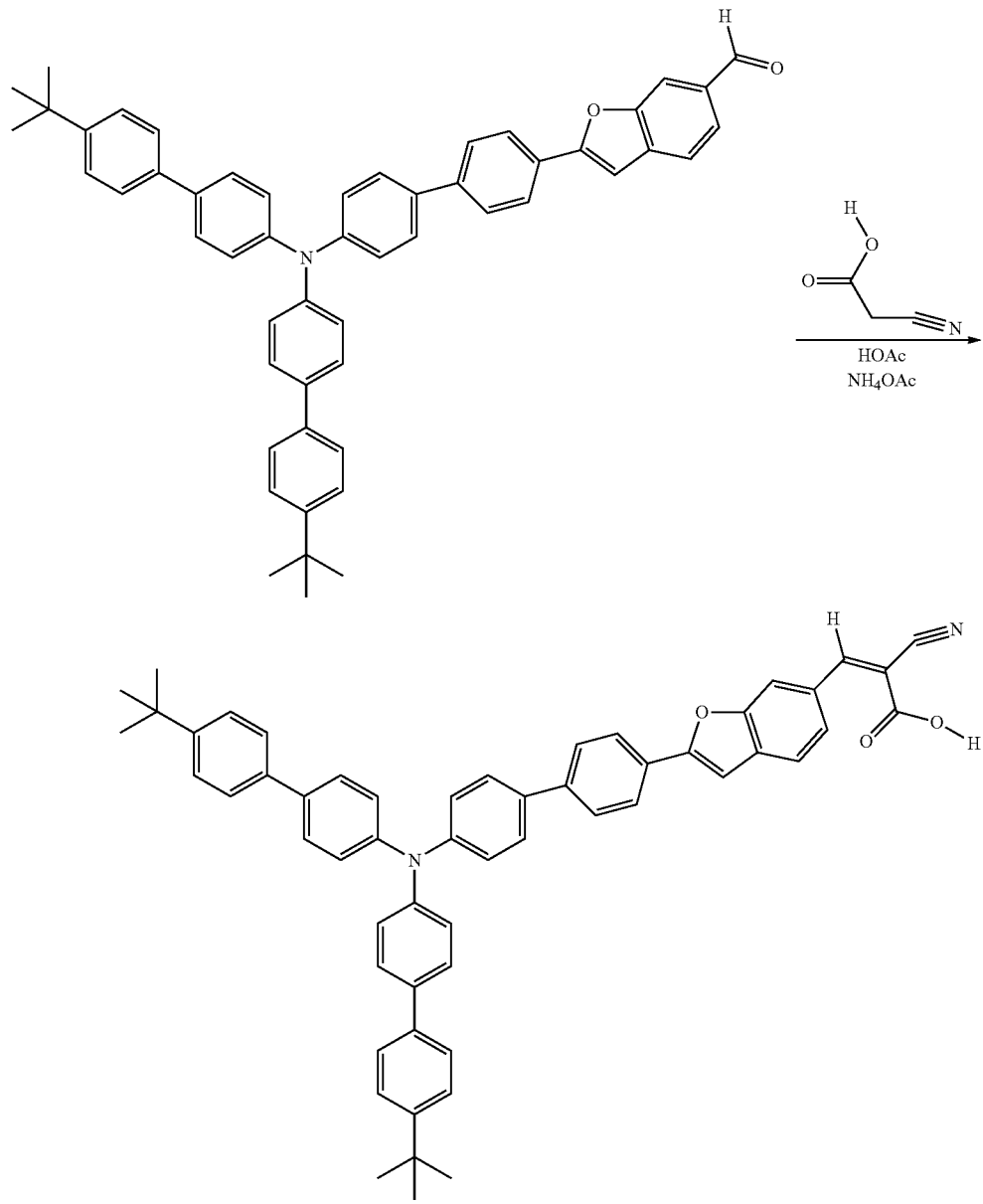

In a round bottom flask, 330 mg (0.45 mmol) 2-[4-[4-[4-(4-tert-butylphenyl)-N-[4-(4-tert-butylphenyl)phenyl]anilino]phenyl]phenyl]benzofuran-6-carbaldehyde, 200 mg (1.85 mmol) cyanoacetic acid and 450 mg (3.6 mmol) ammonium acetate was combined in 12 mL acetic acid and held at reflux for 3 h. Batch was cooled and combined with 50 mL water. Product was filtered off and washed with water (3×5 mL) yielding 300 mg orange solid (83% yield, 92 Area % @ 350 nm, 3% unreacted aldehyde and 5% unknown). UV/Vis max 340 nm & 420 nm, LCMS m/z=797.2.

Example 3. Synthesis of (Z)-2-cyano-3-[2-[4-[4-[4-(4-hexoxyphenyl)-N-[4-(4-hexoxyphenyl)phenyl]anilino]phenyl]phenyl]benzofuran-6-yl]prop-2-enoic acid (D3)

A. 2-[4-[4-[4-(4-hexoxyphenyl)-N-[4-(4-hexoxyphenyl)-phenyl]anilino]phenyl]phenyl]benzofuran-6-carbaldehyde

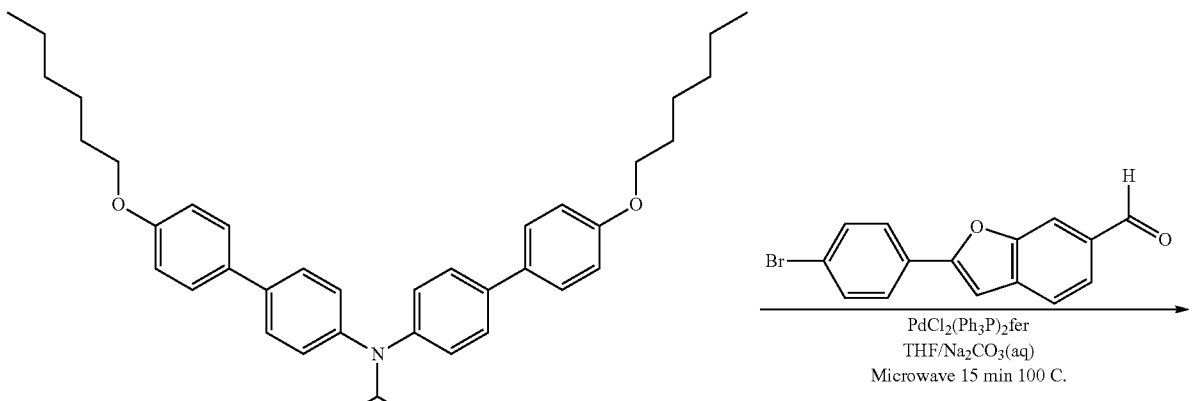

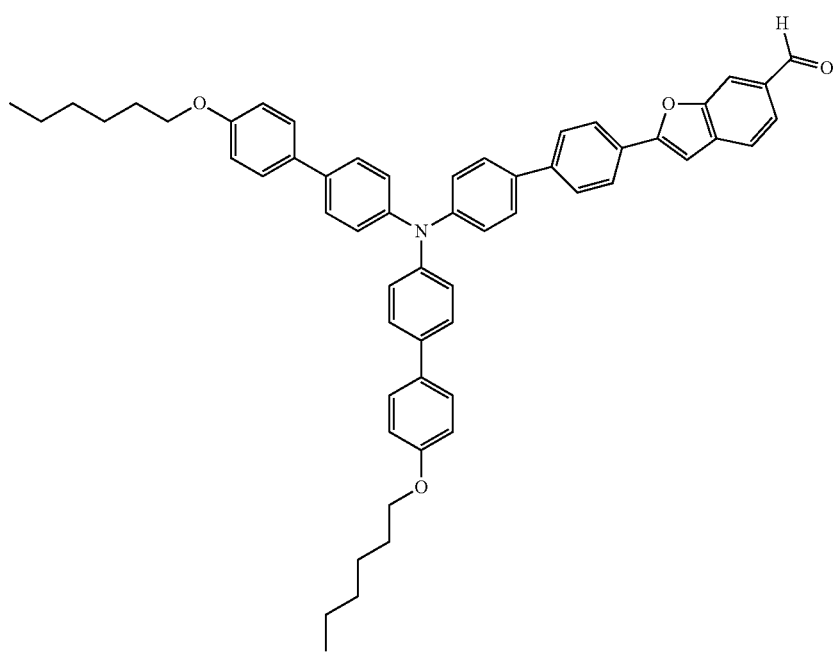

In a round bottom flask, 900 mg (1.24 mmol) N,N-bis[4-(4-hexoxyphenyl)phenyl]-4-(4,4,5,5-tetramethyl-1,3,2-dioxaborolan-2-yl)aniline (see Example 1.C), 411 mg (1.38 mmol) 2-(4-bromophenyl)benzofuran-6-carbaldehyde, 100 mg dichloro 1,1'-bis(diphenylphosphino)-ferrocene palladium(II) was combined in 12 mL THF and 3 mL 10% Na₂CO₃. Batch was microwaved at 100° C. for 20 min. Mixture was poured into water and product extracted into methylene chloride. Product was purified on silica gel (hexane/methylene chloride 0% to 70%), yielding 468 mg (0.572 mmol, 46% yield). LCMS m/z=818.4.

B. (Z)-2-cyano-3-[2-[4-[4-[4-(4-hexoxyphenyl)-N-[4-(4-hexoxyphenyl)phenyl]anilino]phenyl]phenyl]benzofuran-6-yl]prop-2-enoic acid

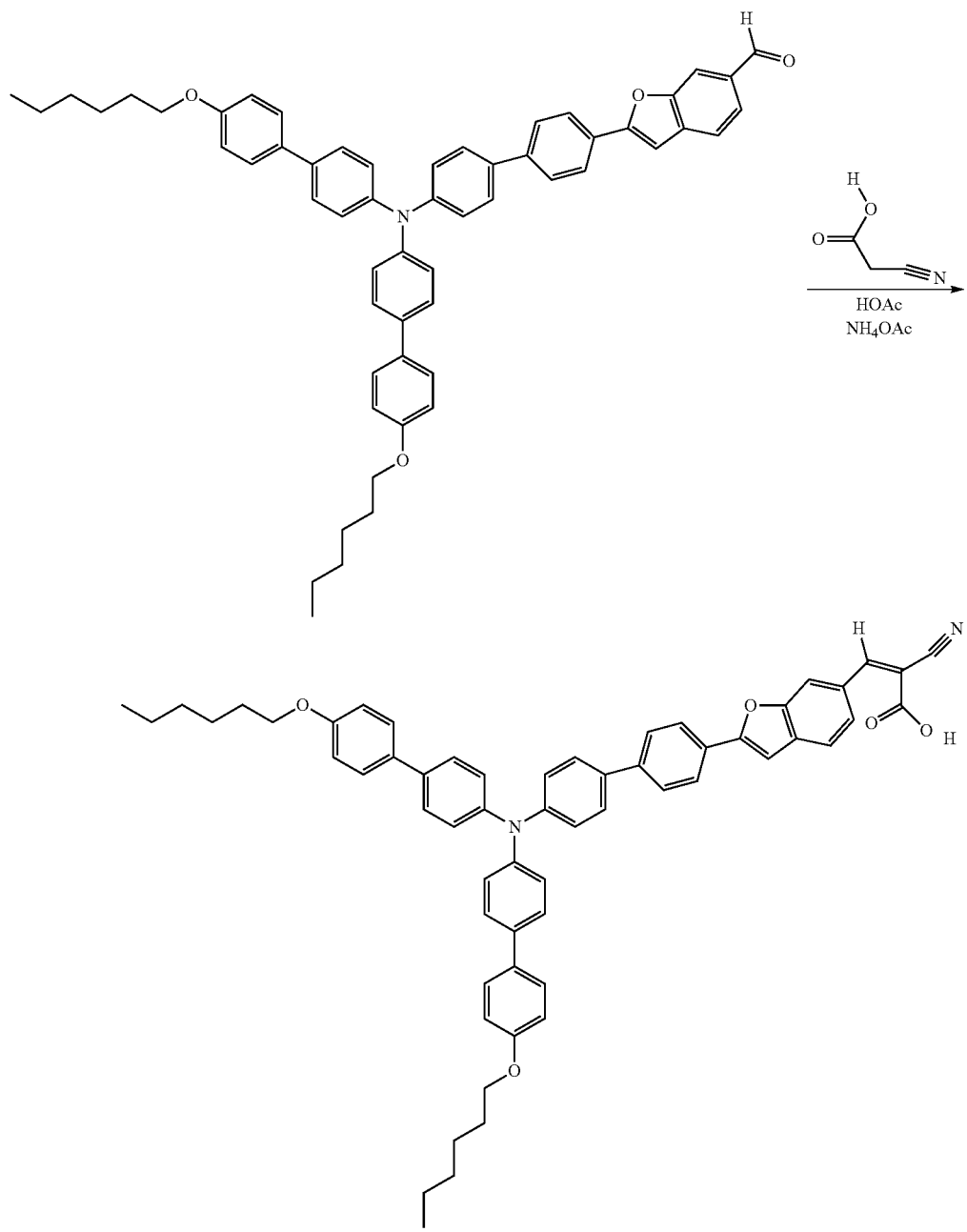

In a round bottom flask, 460 mg (0.56 mmol) 2-[4-[4-[4-(4-hexoxyphenyl)-N-[4-(4-hexoxyphenyl)phenyl]anilino]phenyl]phenyl]benzofuran-6-carbaldehyde, 239 mg (2.8 mmol) cyanoacetic acid and 433 mg ammonium acetate (5.6 mmol) was combined in 12 mL acetic acid and held at reflux for 3 h. Batch was cooled and the product was filtered off, washed with 1 mL HOAc, then washed with water (3×5 mL) and dried, yielding 495 mg orange solid (100% yield). UV/Vis max 340 nm & 420 nm, LCMS m/z=885.8.

Example 4. Synthesis of (Z)-2-cyano-3-[2-[4-[4N-phenylanilino)phenyl]phenyl]benzofuran-6-yl]prop-2-enoic acid (D4)

A. 2-[4-[4-(N-phenylanilino)phenyl]phenyl]benzofuran-6-carbaldehyde

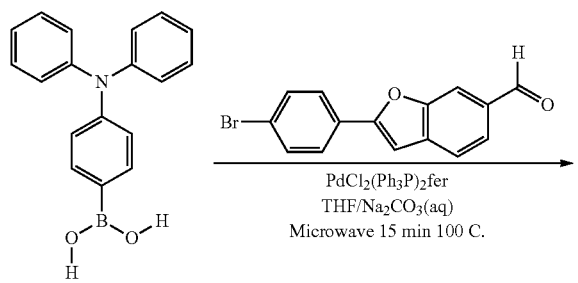

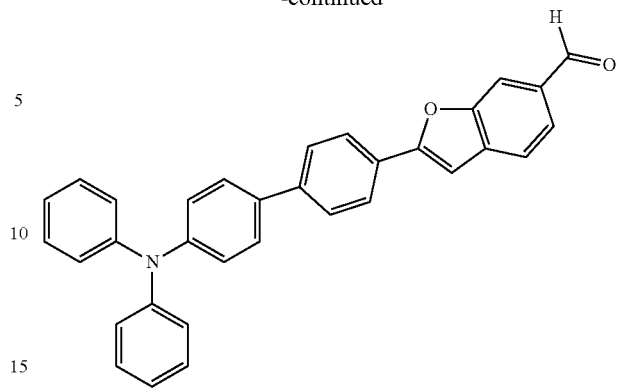

In a round bottom flask, 0.125 g (0.43 mmol) 4-triphenylamine boronic acid, 0.135 g (0.45 mmol) 2-(4-bromophenyl)benzofuran-6-carbaldehyde, and 0.2 g (0.26 mmol) dichloro-bis(diphenylphosphino) ferrocene palladium (II) was combined in 4 mL THF and 1.5 mL 10% $Na_2CO_3$. Batch was microwaved at 100° C. for 15 min. Product was purified on silica gel (hexane/$CH_2Cl_2$). Three fractions were collected. 1(77 mg), 2(50 mg) and 3(26 mg). Fraction 1 was 100 area %, Fractions 2 & 3 were approximately 95 area %. UV/Vis max 380 nm, LCMS m/z=466.2.

B. (Z)-2-cyano-3-[2-[4-[4-(N-phenylanilino)phenyl]-phenyl]benzofuran-6-yl]prop-2-enoic acid

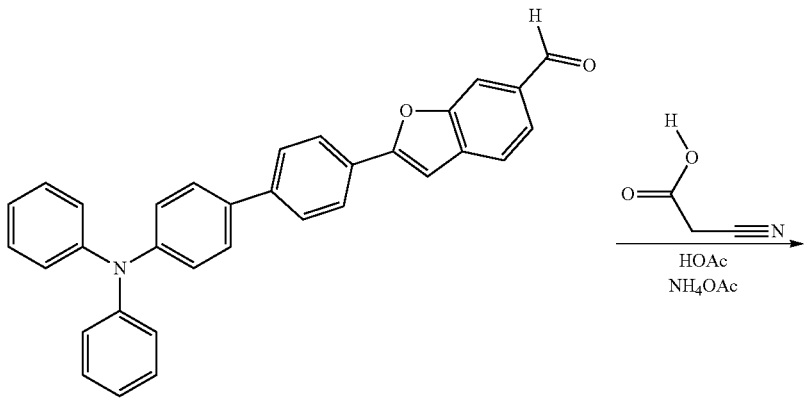

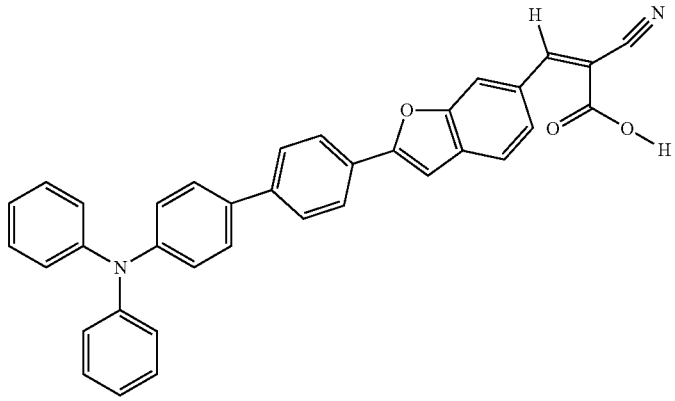

In a round bottom flask, 77 mg (0.163 mmol) 2-[4-[4-(N-phenylanilino)phenyl]phenyl]benzofuran-6-carbaldehyde, 54 mg (0.6 mmol) cyanoacetic acid, and 130 mg ammonium acetate was combined in 5 mL acetic acid and refluxed for 4 h. LCSM showed complete conversion to desired product. Product was filtered off, washed with water and dried yielding 85 mg (0.159 mmol, 97% yield). UV/Vis max 415 nm, LCMS m/z=533.2.

Example 5. Synthesis of (Z)-3-[2-[4-(1-azatricyclo[7.3.1.05,13]trideca-5(13),6,8-trien-7-yl)phenyl]benzofuran-6-yl]-2-cyano-prop-2-enoic acid (D6)

A. 2-[4-(1-azatricyclo[7.3.1.05,13]trideca-5,7,9(13)-trien-7-yl)phenyl]benzofuran-6-carbaldehyde B. (Z)-3-[2-[4-(1-azatricyclo[7.3.1.05,13]trideca-5(13),6,8-trien-7-yl)phenyl]benzofuran-6-yl]-2-cyano-prop-2-enoic acid

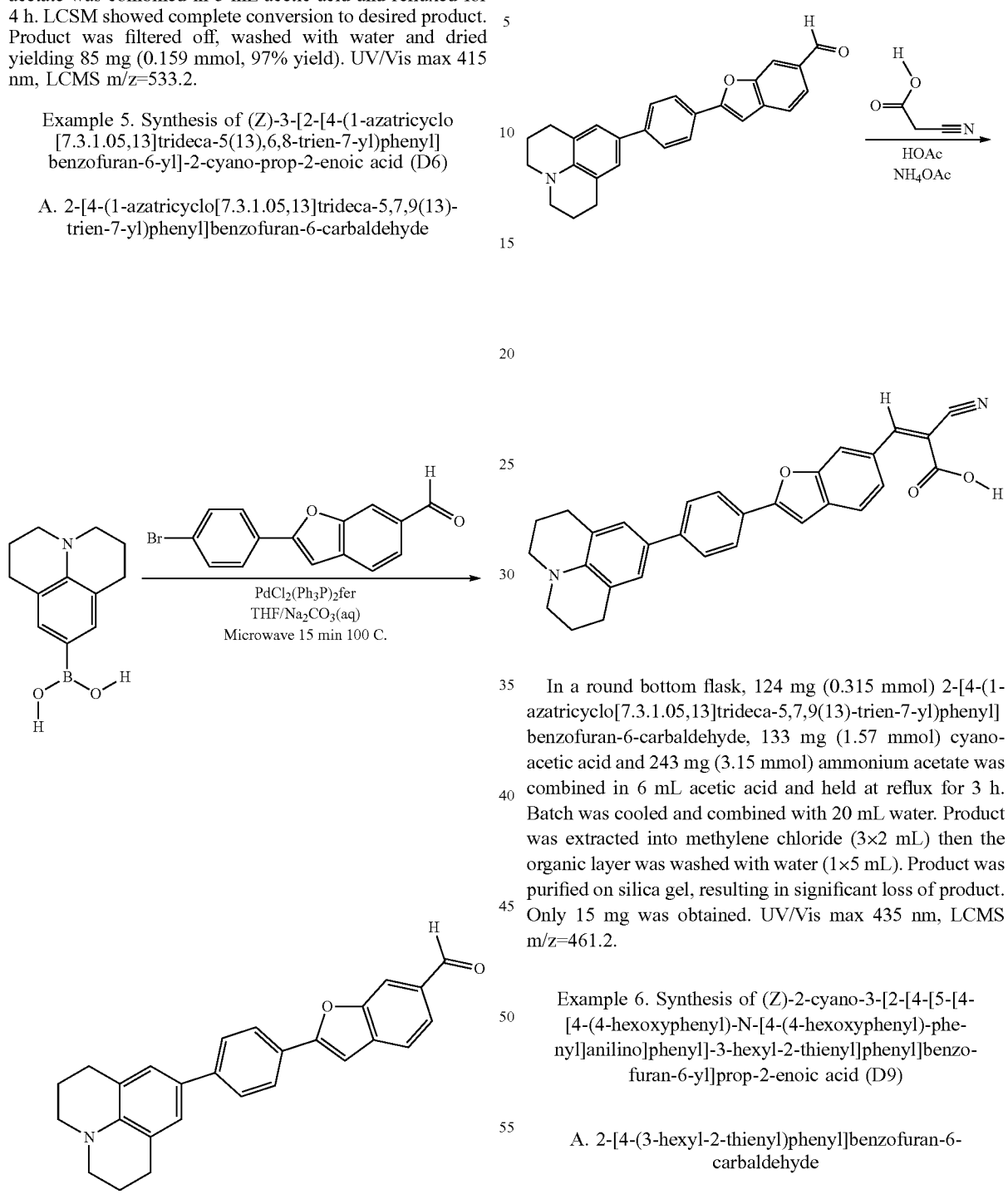

In a round bottom flask, 124 mg (0.315 mmol) 2-[4-(1-azatricyclo[7.3.1.05,13]trideca-5,7,9(13)-trien-7-yl)phenyl]benzofuran-6-carbaldehyde, 133 mg (1.57 mmol) cyanoacetic acid and 243 mg (3.15 mmol) ammonium acetate was combined in 6 mL acetic acid and held at reflux for 3 h. Batch was cooled and combined with 20 mL water. Product was extracted into methylene chloride (3×2 mL) then the organic layer was washed with water (1×5 mL). Product was purified on silica gel, resulting in significant loss of product. Only 15 mg was obtained. UV/Vis max 435 nm, LCMS m/z=461.2.

Example 6. Synthesis of (Z)-2-cyano-3-[2-[4-[5-[4-[4-(4-hexoxyphenyl)-N-[4-(4-hexoxyphenyl)-phenyl]anilino]phenyl]-3-hexyl-2-thienyl]phenyl]benzofuran-6-yl]prop-2-enoic acid (D9)

A. 2-[4-(3-hexyl-2-thienyl)phenyl]benzofuran-6-carbaldehyde

In a round bottom flask, 0.217 g (1 mmol) julolidine boronic acid, 0.33 g (1.1 mmol) 2-(4-bromophenyl)benzofuran-6-carbaldehyde and 30 mg (0.04 mmol) dichloro-bis(diphenylphosphino) ferrocene palladium (II) was combined in 4 mL THF and 1.5 mL 10% Na₂CO₃. Batch was microwaved at 100° C. for 15 min, then purified on silica gel (CH₂Cl₂/hexane), yielding 124 mg (31% yield). UV/Vis max 400 nm, LCMS m/z=394.0.

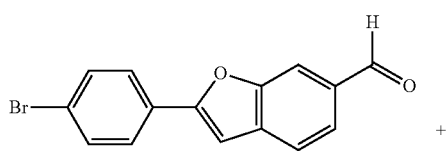

B. 2-[4-(5-bromo-3-hexyl-2-thienyl)phenyl]benzofuran-6-carbaldehyde

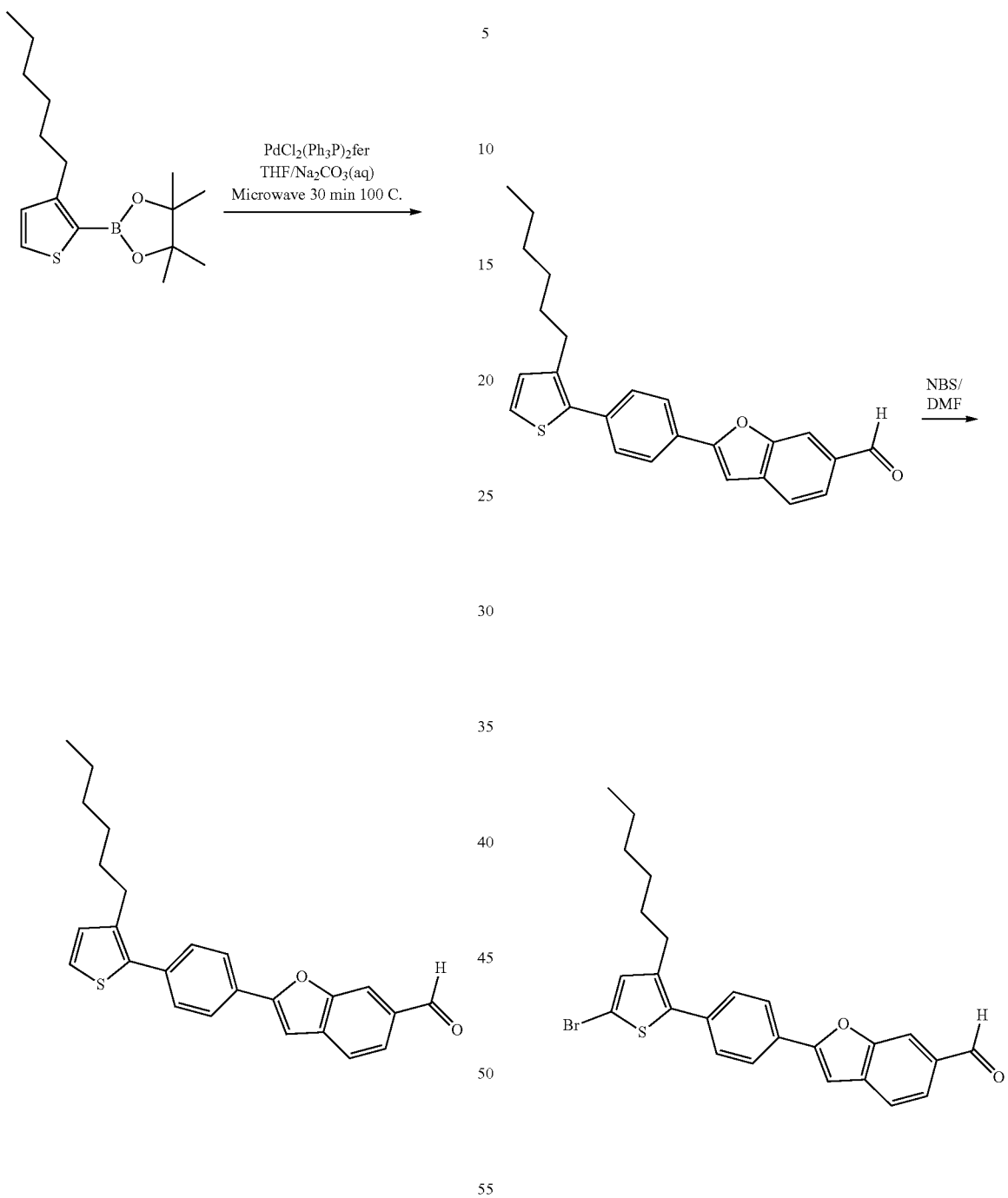

In a round bottom flask, 225 mg (0.75 mmol) 2-(4-bromophenyl)benzofuran-6-carbaldehyde, 242 mg (0.82 mmol), 3-hexylthiophene-2-boronic acid pinacol ester and 30 mg (0.04 mmol) dichloro-bis(diphenylphosphino) ferrocene palladium (II) was combined in 4 mL THF and 1.5 mL 10% $Na_2CO_3$. Batch was microwaved at 100° C. for 30 min and purified on silica gel ($CH_2Cl_2$/hexane), yielding 205 mg (0.527 mmol, 70% yield). UV/Vis max 350 nm, LCMS m/z=389.1.

In a round bottom flask, 205 mg (0.53 mmol) 2-[4-(3-hexyl-2-thienyl)phenyl]benzofuran-6-carbaldehyde in 5 mL DMF was cooled to 5° C. A solution of 93 mg NBS (0.53 mmol) in 3 mL DMF was added dropwise and the batch was allowed to warm to rt. Batch was poured into 20 mL water and the product was extracted into methylene chloride and purified on silica gel, yielding 60 mg (0.13 mmol, 24% yield). UV/Vis max 350 nm, LCMS m/z=467.0, 469.0.

C. 2-[4-[5-[4-[4-(4-hexoxyphenyl)-N-[4-(4-hexoxy-phenyl)-phenyl]anilino]phenyl]-3-hexyl-2-thienyl]phenyl]benzofuran-6-carbaldehyde
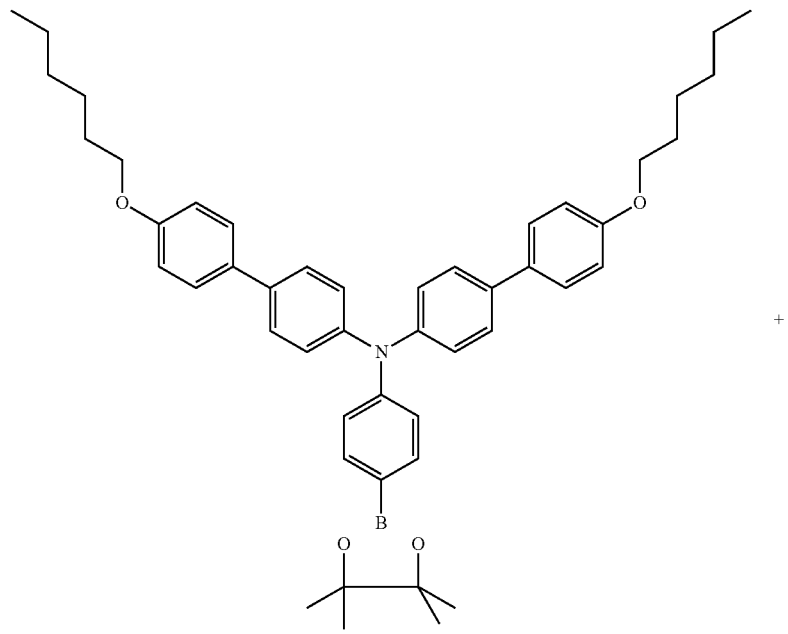
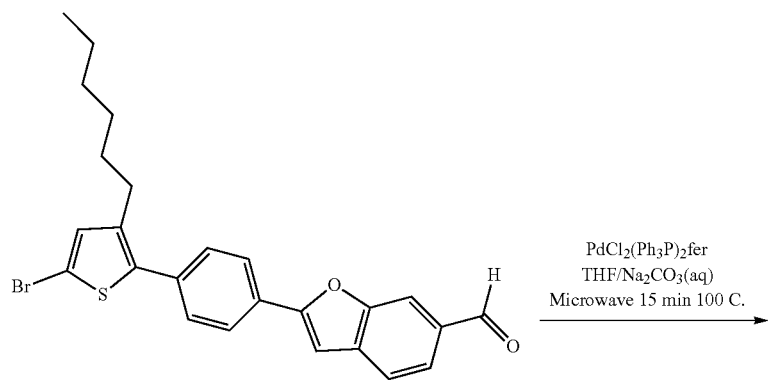

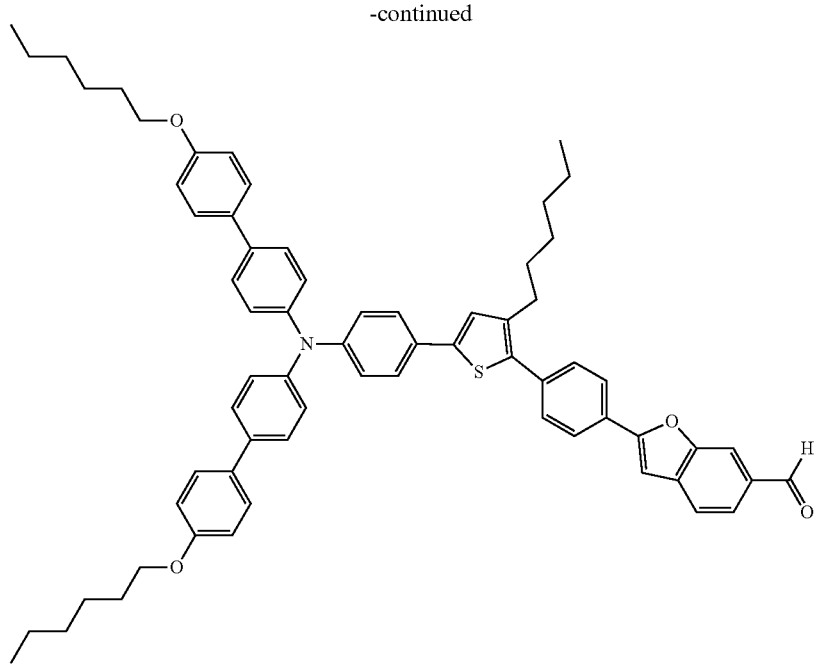

In a round bottom flask, 92 mg (0.13 mmol) N,N-bis[4-(4-hexoxyphenyl)phenyl]-4-(4,4,5,5-tetramethyl-1,3,2-dioxaborolan-2-yl)aniline (see Example 1.C), 60 mg (0.13 mmol) aldehyde intermediate (Lot DJ1374), and 20 mg (0.026 mmol) dichloro-bis(diphenylphosphino)ferrocene palladium (II) was combined in 4 mL THF and 1.5 mL 10% $Na_2CO_3$. Batch was microwaved at 100° C. for 15 min. Product was purified on silica gel (hexane/$CH_2Cl_2$), yielding 52 mg (0.052 mmol, 40% yield). UV/Vis max 345 nm & 495 nm, LCMS m/z=984.6.

D. (Z)-2-cyano-3-[2-[4-[5-[4-[4-(4-hexoxyphenyl)-N-[4-(4-hexoxyphenyl)-phenyl]anilino]phenyl]-3-hexyl-2-thienyl]phenyl]benzofuran-6-yl]prop-2-enoic acid

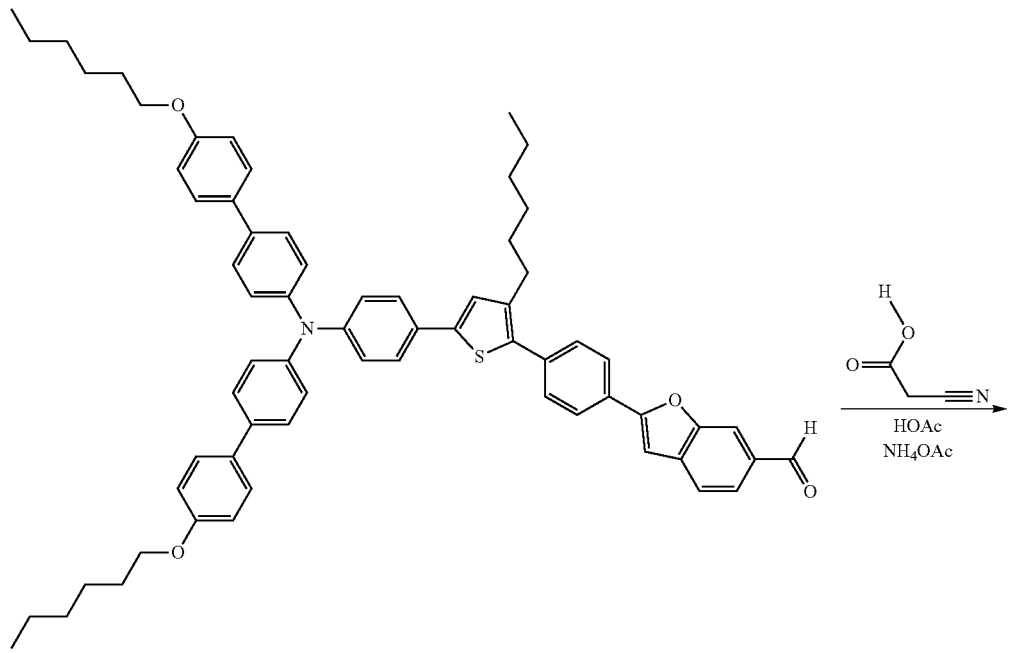

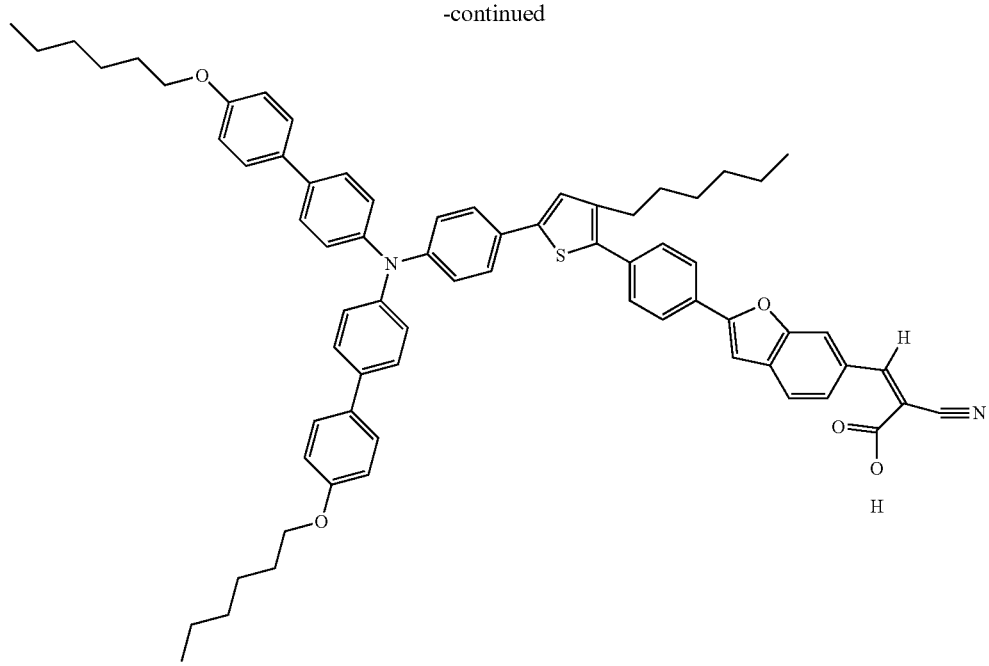

In a round bottom flask, 52 mg (0.052 mmoles) 2-[4-[5-[4-[4-(4-hexoxyphenyl)-N-[4-(4-hexoxyphenyl)phenyl]anilino]phenyl]-3-hexyl-2-thienyl]phenyl]benzofuran-6-carbaldehyde, 21 mg (0.25 mmol) cyanoacetic acid and 38 mg (0.5 mmol) ammonium acetate was combined in 6 mL HOAc and refluxed for 2 h. Batch was cooled and combined with 20 mL water. Product was filtered off, washed with water and dried, yielding 58 mg (0.05 mmol, 100% yield). UV/Vis max 350 nm & 410 nm, LCMS m/z=1051.4.

Example 7. Synthesis of (Z)-2-cyano-3-[2-[5-[4-[4-(4-hexoxyphenyl)-N-[4-(4-hexoxyphenyl)phenyl]anilino]phenyl]-2-thienyl]benzofuran-6-yl]prop-2-enoic acid (D10)

A. 2-[5-[4-[4-(4-hexoxyphenyl)-N-[4-(4-hexoxyphenyl)-phenyl]anilino]phenyl]-2-thienyl]benzofuran-6-carbaldehyde

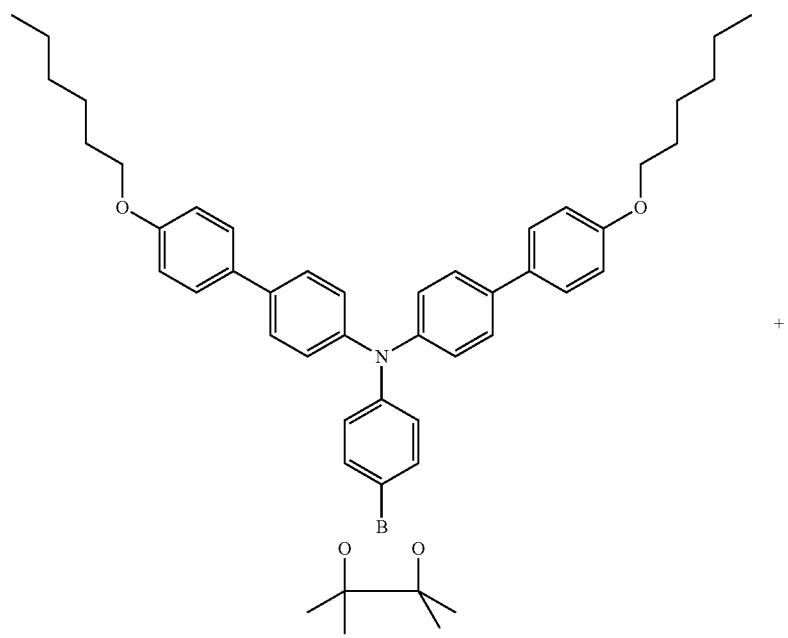

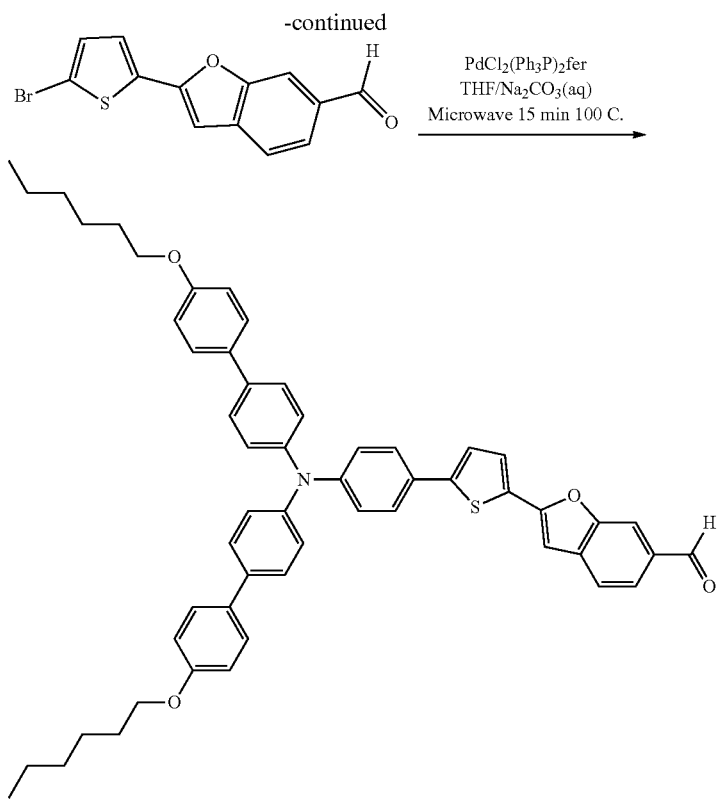

In a round bottom flask, 276 mg (0.38 mmol) N,N-bis[4-(4-hexoxyphenyl)phenyl]-4-(4,4,5,5-tetramethyl-1,3,2-dioxaborolan-2-yl)aniline (see Example 1.C), 130 mg (0.42 mmol) 2-(5-bromo-2-thienyl)benzofuran-6-carbaldehyde, and 50 mg (0.06 mmol) dichloro-bis(diphenylphosphino) ferrocene palladium (II) was combined in 4 mL THF and 1.5 mL 10% $Na_2CO_3$. Batch was microwaved at 100° C. for 15 min. Product was purified on silica gel (hexane/$CH_2Cl_2$) yielding 160 mg (0.19 mmol, 50% yield). UV/Vis max 340 nm & 425 nm, LCMS m/z=824.4

B. (Z)-2-cyano-3-[2-[5-[4-[4-(4-hexoxyphenyl)-N-[4-(4-hexoxyphenyl)phenyl]anilino]phenyl]-2-thienyl]benzofuran-6-yl]prop-2-enoic acid

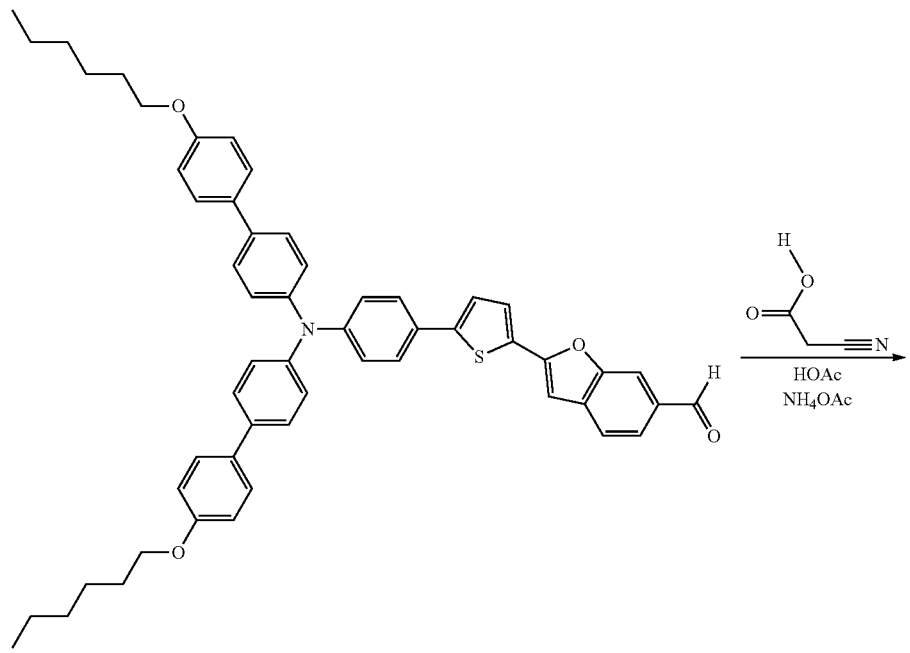

-continued

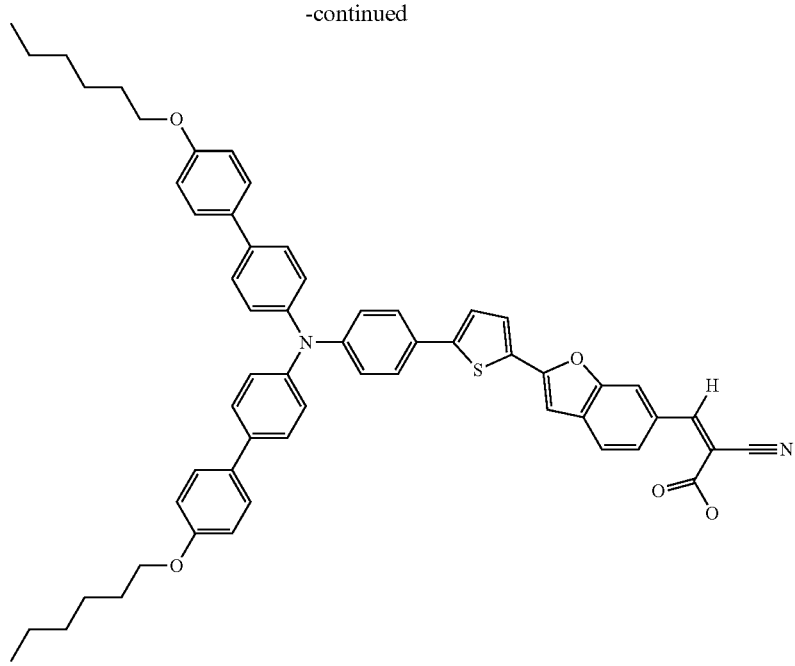

In a round bottom flask, 250 mg (0.3 mmoles) 2-[5-[4-[4-(4-hexoxyphenyl)-N-[4-(4-hexoxyphenyl)phenyl]anilino]phenyl]-2-thienyl]benzofuran-6-carbaldehyde, 129 mg (1.5 mmol) cyanoacetic acid and 231 mg (3 mmol) ammonium acetate was combined in 6 mL HOAc and refluxed for 2 h. Batch was cooled. Product was filtered off, washed with 2 mL acetic acid then water and dried, yielding 247 mg (0.28 mmol, 93% yield). UV/Vis max 345 nm & 455 nm, LCMS m/z=891.6.

Example 8. Synthesis of (Z)-2-cyano-3-[2-[5-[4-(N-phenylanilino)phenyl]-2-thienyl]benzofuran-6-yl]prop-2-enoic acid (D12)

A. 2-[5-[4-(N-phenylanilino)phenyl]-2-thienyl]benzofuran-6-carbaldehyde

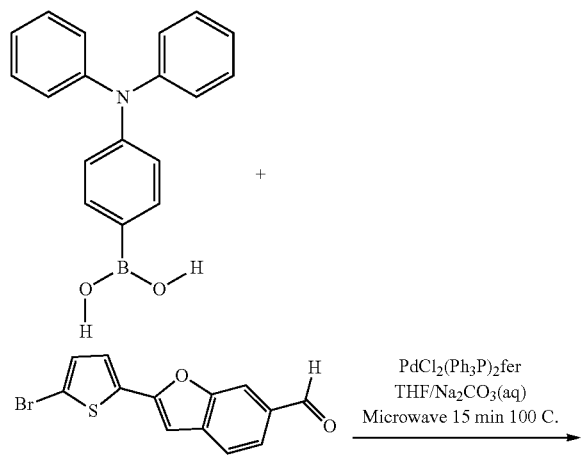

-continued

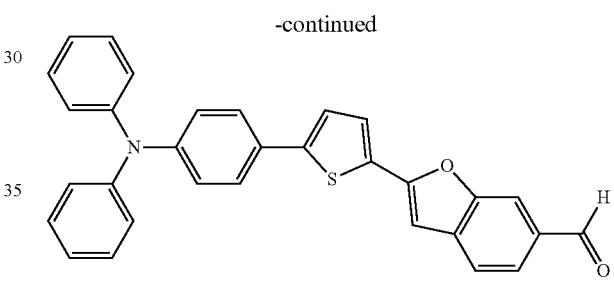

In a round bottom flask, 144 mg (0.5 mmol) 4-diphenylamino phenylboronic acid, 168 mg (~0.5 mmol assuming ~90% pure) 2-(5-bromo-2-thienyl)benzofuran-6-carbaldehyde, and 20 mg (0.026 mmol) dichloro-bis(diphenylphosphino) ferrocene palladium (II) was combined in 4 mL THF and 1.5 mL 10% $Na_2CO_3$. Batch was microwaved at 100° C. for 15 min. Product was purified on silica gel (hexane/$CH_2Cl_2$) yielding 80 mg (0.17 mmol, 34% yield). UV/Vis max 415 nm, LCMS m/z=472.2.

B. (Z)-2-cyano-3-[2-[5-[4-(N-phenylanilino)phenyl]-2-thienyl]benzofuran-6-yl]prop-2-enoic acid

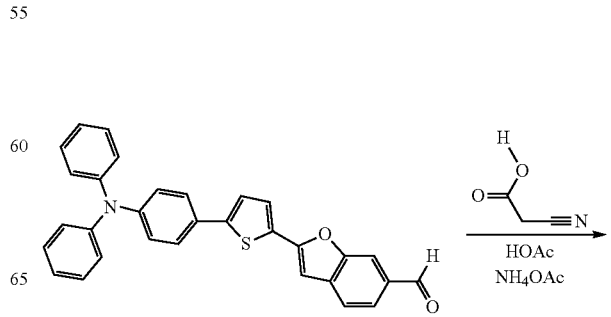

-continued

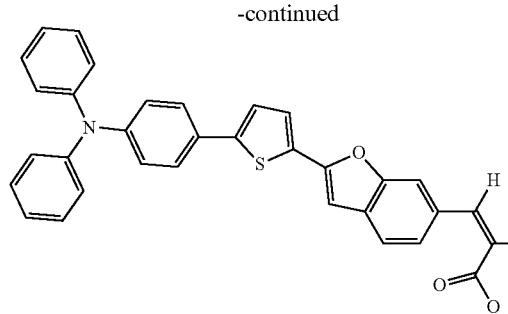

In a round bottom flask, 80 mg (0.17 mmoles) 2-[5-[4-(N-phenylanilino)phenyl]-2-thienyl]benzofuran-6-carbaldehyde, 72 mg (0.85 mmol) cyanoacetic acid and 130 mg (1.7 mmol) ammonium acetate was combined in 6 mL HOAc and refluxed for 2 h. Batch was cooled and combined with 20 mL water. Product was filtered off, washed with water and dried yielding 90 mg (0.16 mmol, 94% yield). UV/Vis max 445 nm, LCMS m/z=539.2.

Example 9. Synthesis of (Z)-3-[2-[5-(1-azatricyclo[7.3.1.05,13]trideca-5(13),6,8-trien-7-yl)-2-thienyl]benzofuran-6-yl]-2-cyano-prop-2-enoic acid (D11)

A. 2-[5-(1-azatricyclo[7.3.1.05,13]trideca-5,7,9(13)-trien-7-yl)-2-thienyl]benzofuran-6-carbaldehyde

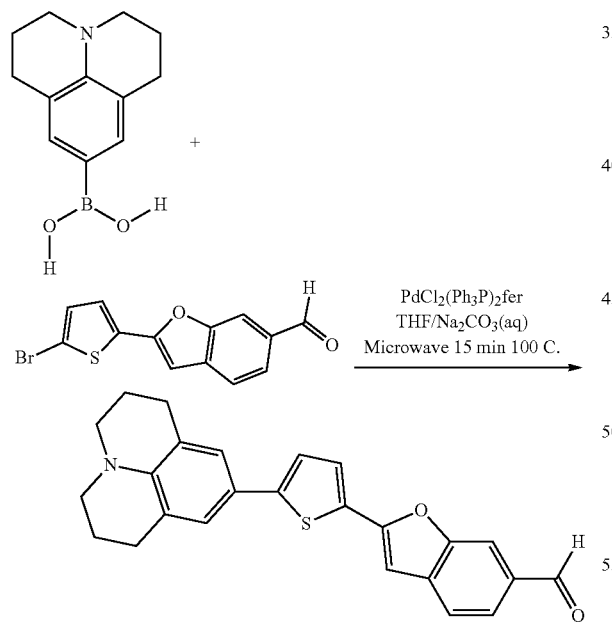

In a round bottom flask, 141 mg (0.65 mmol) julolidine boronic acid, 200 mg (~0.65 mmol) 2-(5-bromo-2-thienyl)benzofuran-6-carbaldehyde, and 20 mg (0.026 mmol) dichloro-bis(diphenylphosphino) ferrocene palladium (II) was combined in 4 mL THF and 1.5 mL 10% Na$_2$CO$_3$. Batch was microwaved at 100° C. for 15 min. Product was purified on silica gel (hexane/CH$_2$Cl$_2$), yielding 50 mg (0.125 mmol, 19% yield). UV/Vis max 420 nm, LCMS m/z=400.2.

B. (Z)-3-[2-[5-(1-azatricyclo[7.3.1.05,13]trideca-5(13),6,8-trien-7-yl)-2-thienyl]benzofuran-6-yl]-2-cyano-prop-2-enoic acid

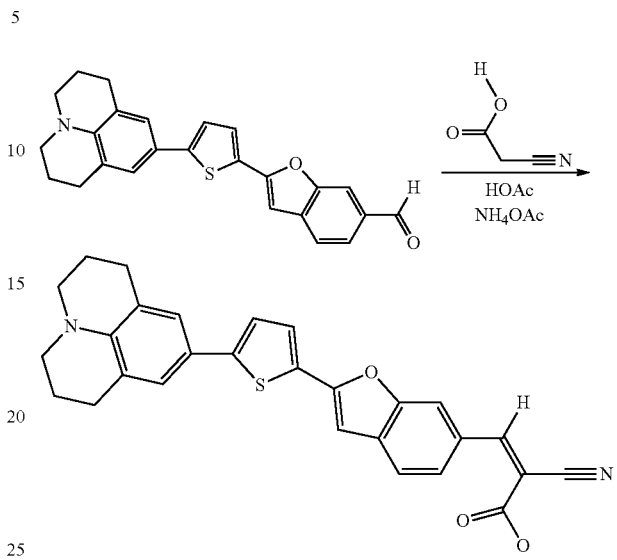

In a round bottom flask, 50 mg (0.12 mmoles) 2-[5-(1-azatricyclo[7.3.1.05,13]trideca-5,7,9(13)-trien-7-yl)-2-thienyl]benzofuran-6-carbaldehyde, 53 mg (0.63 mmol) cyanoacetic acid and 96 mg (1.2 mmol) ammonium acetate was combined in 6 mL HOAc at 90° C. for 6 h. Reaction was stopped at 90% completion. Batch was cooled and product filtered off, washed with water and dried, yielding 50 mg (0.11 mmol, 85% yield). UV/Vis max 475 nm, LCMS m/z=467.2.

Example 10. Synthesis of (Z)-2-cyano-3-[2-[7,7-dibutyl-10-[4-[4-(4-hexoxyphenyl)-N-[4-(4-hexoxyphenyl)phenyl]anilino]phenyl]-3,11-dithiatricyclo[6.3.0.02,6]undeca-1(8),2(6),4,9-tetraen-4-yl]benzofuran-6-yl]prop-2-enoic acid (D14)

A. 7,7-dibutyl-3,11-dithiatricyclo[6.3.0.02,6]undeca-1(8),2(6),4,9-tetraene

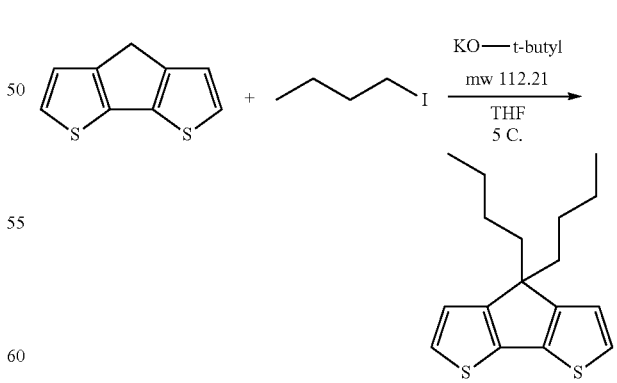

In a round bottom flask, 2.3 g (12.9 mmol) 4H-Cyclopenta[1,2-b:5,4-b']dithiophene in 25 mL THF at 5° C. was treated with 4.15 g (37 mmol) potassium t-butoxide followed by the addition of 4.76 g (25.9 mmol) 1-iodobutane. Batch was poured into water and extracted into methylene chloride.

The organic layer was concentrated and passed thru a silica gel column (80 g), eluted with hexane and concentrated, yielding 3.1 g light yellow solid (oily crystals). 97A % by HPLC (85% yield). UV/Vis max 315 nm, LCMS m/z=291.1.

B. 4-bromo-7,7-dibutyl-3,11-dithiatricyclo[6.3.0.02,6]undeca-1(8),2(6),4,9-tetraene

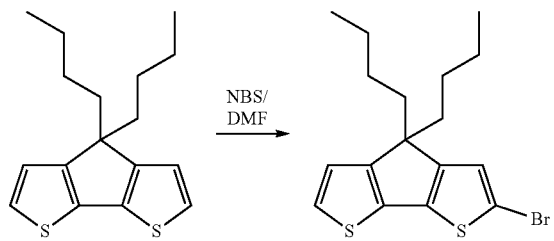 [SMILES: CCCCC1(CCCC)c2ccsc2-c2sccc21 ; CCCCC1(CCCC)c2ccsc2-c2sc(Br)cc21]

In a round bottom flask, 1.6 g (5.5 mmol) 7,7-dibutyl-3,11-dithiatricyclo[6.3.0.02,6]undeca-1(8),2(6),4,9-tetraene was dissolved in 15 mL DMF was cooled to 5° C. A solution 0.95 g (5.3 mmol) N-bromosuccinamide in 5 mL DMF was added dropwise over 30 min. The mixture was poured into 100 mL water and extracted with methylene chloride. The organic layer was separated, concentrated and passed through a silica gel column (hexane) yielding 0.91 g (2.46 mmol, 45% yield) yellow oil. UV/Vis max 325 nm, LCMS m/z=368.9, 370.9.

C. 2-(7,7-dibutyl-3,11-dithiatricyclo[6.3.0.02,6]undeca-1(8),2(6),4,9-tetraen-4-yl)ethynyl-trimethyl-silane

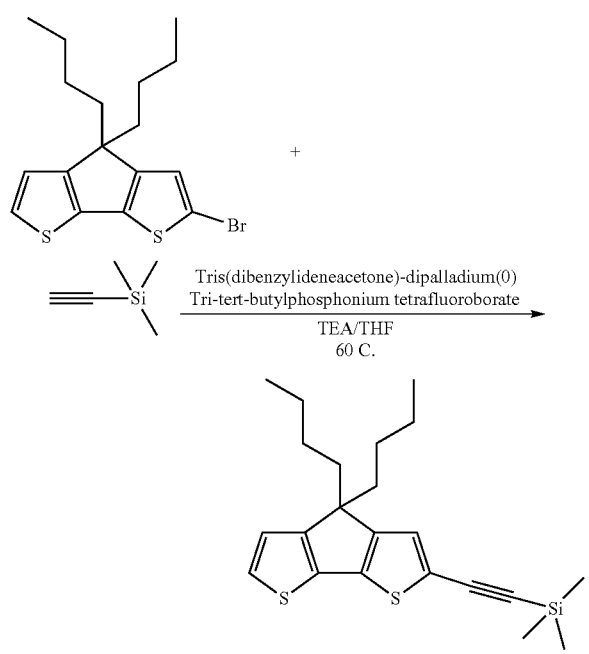

In a round bottom flask, 0.91 g (2.46 mmol) 4-bromo-7,7-dibutyl-3,11-dithiatricyclo[6.3.0.02,6]undeca-1(8),2(6),4,9-tetraene, 100 mg tri-tert-butylphosphonium tetrafluoroborate, 110 mg tris(dibenzylideneacetone) dipalladium(0) and 0.725 g (7.4 mmol) TMS-acetylene was combined in 6 mL TEA in a sealed pressure tube. Mixture was held at 60° C. for 18 h then poured into 25 mL water containing 5 mL of acetic acid (pH 6-7). The product was extracted into methylene chloride, concentrated and purified on silica gel (hexane) yielding 640 mg dark oil, (67% yield). UV/Vis max 360 nm, LCMS m/z=387.2.

D. 2-(7,7-dibutyl-10-iodo-3,11-dithiatricyclo[6.3.0.02,6]undeca-1(8),2(6),4,9-tetraen-4-yl)ethynyl-trimethyl-silane

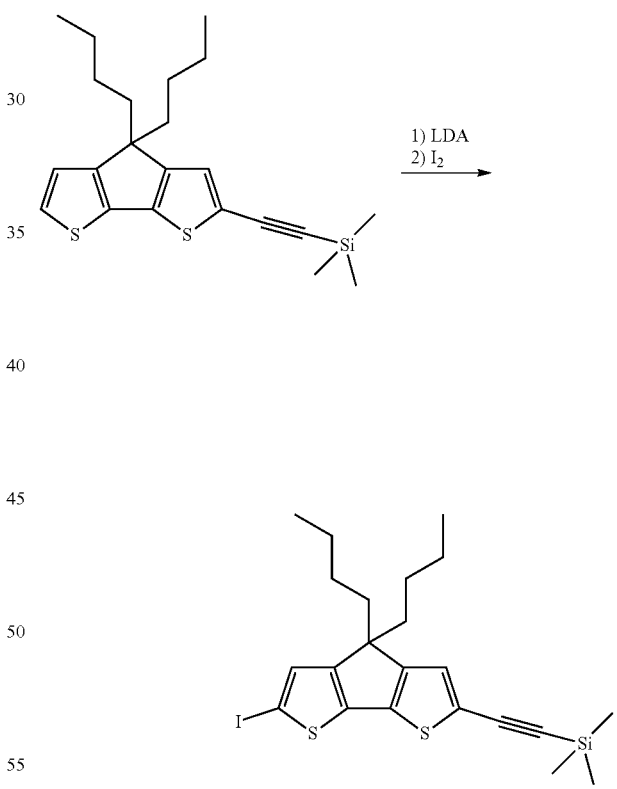

In a round bottom flask, 300 mg (0.775 mmol) 4,4-dibutyl-2-TMS-acetylene-cyclopentadithiophene was added to 4 mL diethyl ether at −78° C. 1.5 mL LDA (1M solution, 1.5 mmol) was added, then batch was warmed to 0° C. for 15 min. Batch was cooled back to −78° C. and 381 mg (1.5 mmol) iodine in 4 mL ether added. Batch was warmed to rt. HPLC showed complete reaction. Purification on silica gel (hexane) yielded 300 mg yellow oil (75% yield). UV/Vis max 370 nm, LCMS m/z=512.9.

E. N-[4-[7,7-dibutyl-10-(2-trimethylsilylethynyl)-3,11-dithiatricyclo[6.3.0.02,6]undeca-1(8),2(6),4,9-tetraen-4-yl]phenyl]-4-(4-hexoxyphenyl)-N-[4-(4-hexoxyphenyl)phenyl]aniline
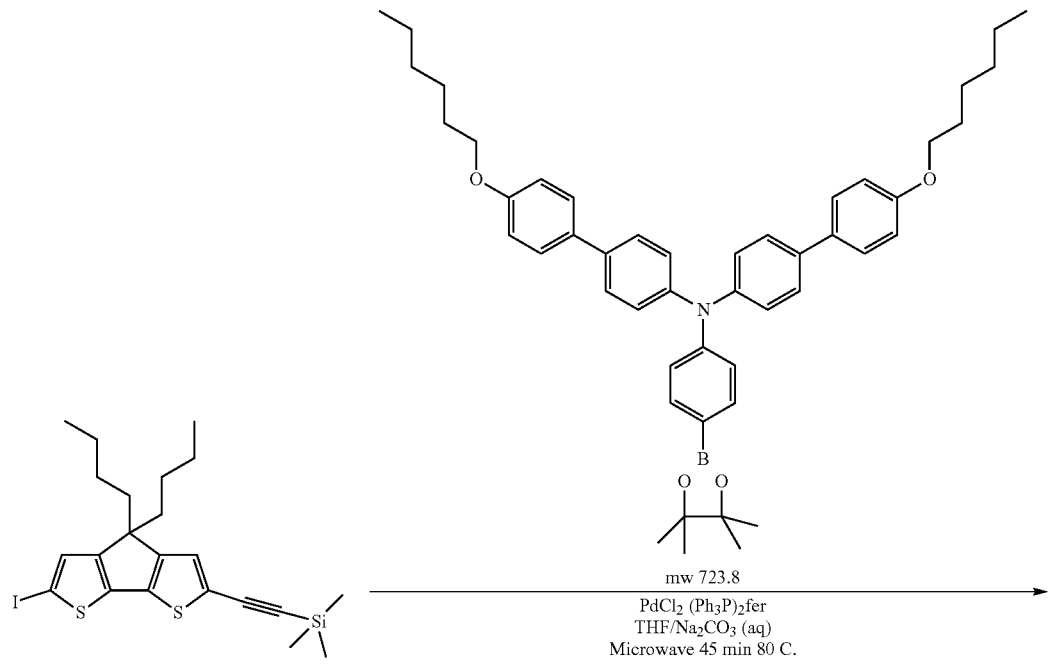
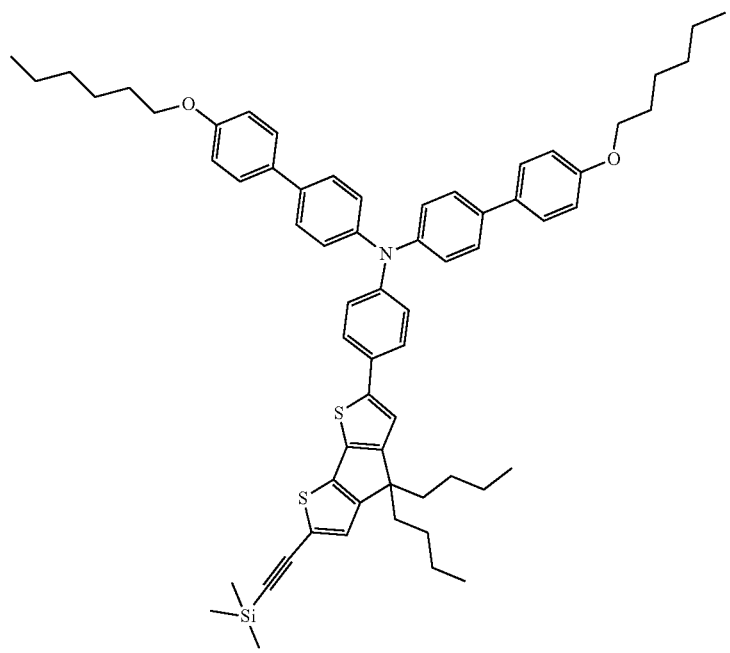

In a round bottom flask, 100 mg (0.195 mmol) 2-(7,7-dibutyl-10-iodo-3,11-dithiatricyclo[6.3.0.02,6]undeca-1(8),2(6),4,9-tetraen-4-yl)ethynyl-trimethyl-silane, 141 mg (0.195 mmol) N,N-bis[4-(4-hexoxyphenyl)phenyl]-4-(4,4,5,5-tetramethyl-1,3,2-dioxaborolan-2-yl)aniline and 30 mg (0.04 mmol) dichloro 1,1'-bis(diphenylphosphino)ferrocene palladium(II) was combined in 3 mL THF and 2 mL 10% $Na_2CO_3$. Mixture was microwaved at 80° C. for 45 min then poured into 20 mL water. The product was extracted into methylene chloride and purified on silica gel (hexane/methylene chloride) yielding 86 mg (0.087 mmol, 44.6% yield). UV/Vis max 420 nm, LCMS m/z=982.4.

F. N-[4-(7,7-dibutyl-10-ethynyl-3,11-dithiatricyclo[6.3.0.02,6]undeca-1(8),2(6),4,9-tetraen-4-yl)phenyl]-4-(4-hexoxyphenyl)-N-[4-(4-hexoxyphenyl)phenyl]aniline

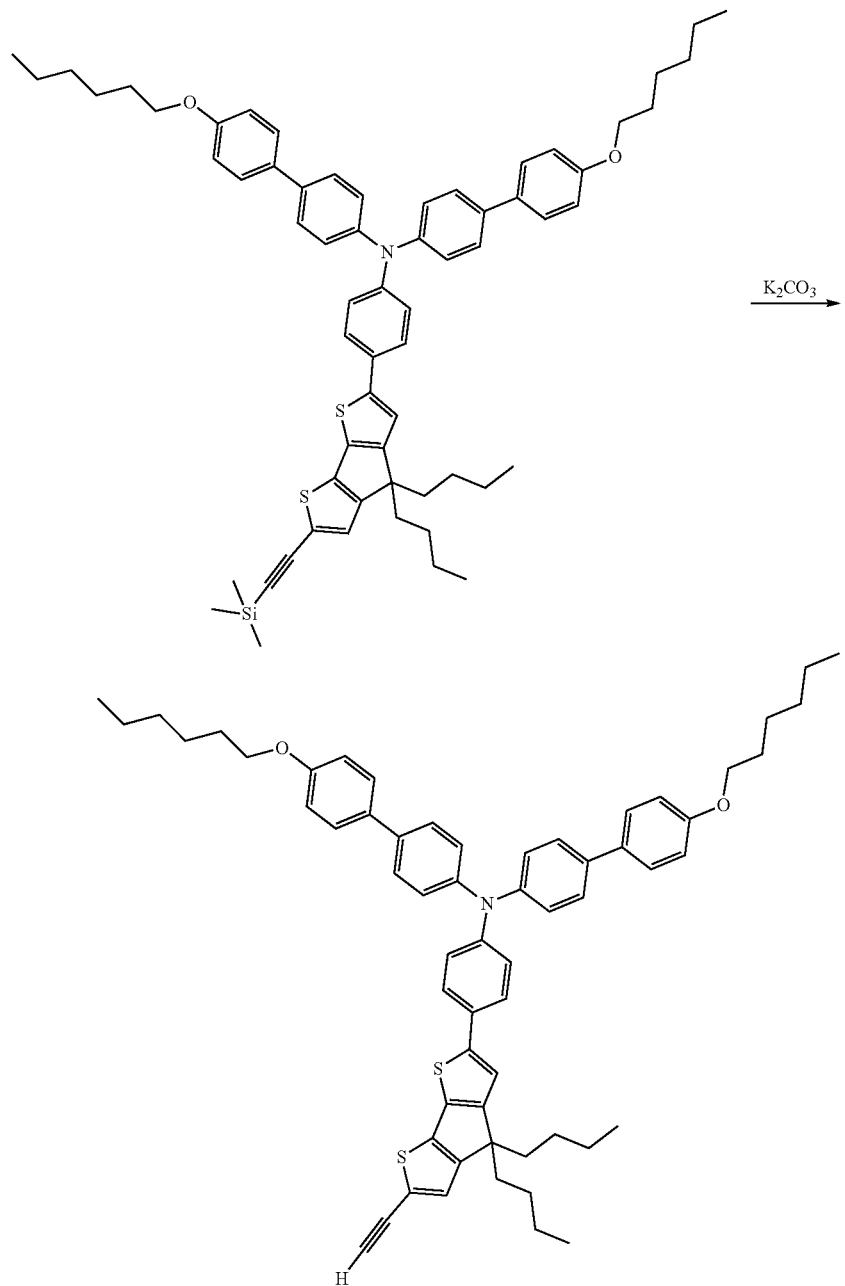

In a round bottom flask, 86 mg (0.087 mmol) N-[4-[7,7-dibutyl-10-(2-trimethylsilylethynyl)-3,11-dithiatricyclo[6.3.0.02,6]undeca-1(8),2(6),4,9-tetraen-4-yl]phenyl]-4-(4-hexoxyphenyl)-N-[4-(4-hexoxyphenyl)phenyl]aniline and 200 mg $K_2CO_3$ was combined in 3 mL $CH_2Cl_2$ and 3 mL methanol stirred at rt for 1 h. 10 mL water was added, organic layer separated, dried and concentrated, yielding 69 mg (87% yield). UV/Vis max 420 nm, LCMS m/z=910.6. 1H NMR (400 MHz, $CDCl_3$): 7.44-7.51 (m, 10H; CHarom), 7.09-7.18 (m, 8H; CHarom), 6.93-6.96 (m, 4H; CHarom), 3.98 (t, 4H; —OCH2-), 3.45 (s, 1H; acetylene-H), 1.75-1.84 (m, 8H; —CH2-arom, —CH2-), 1.43-1.48 (m, 4H; —CH2-), 1.33-1.36 (m, 8H; —CH2-), 1.13-1.18 (m, 4H; —CH2-), 0.88-0.92 (m, 10H; —CH2-, —CH3), 0.76 (t, 6H; —CH3).

G. 2-[7,7-dibutyl-10-[4-[4-(4-hexoxyphenyl)-N-[4-(4-hexoxyphenyl)-phenyl]anilino]phenyl]-3,11-dithiatricyclo[6.3.0.02,6]undeca-1(8),2(6),4,9-tetraen-4-yl]benzofuran-6-carbaldehyde

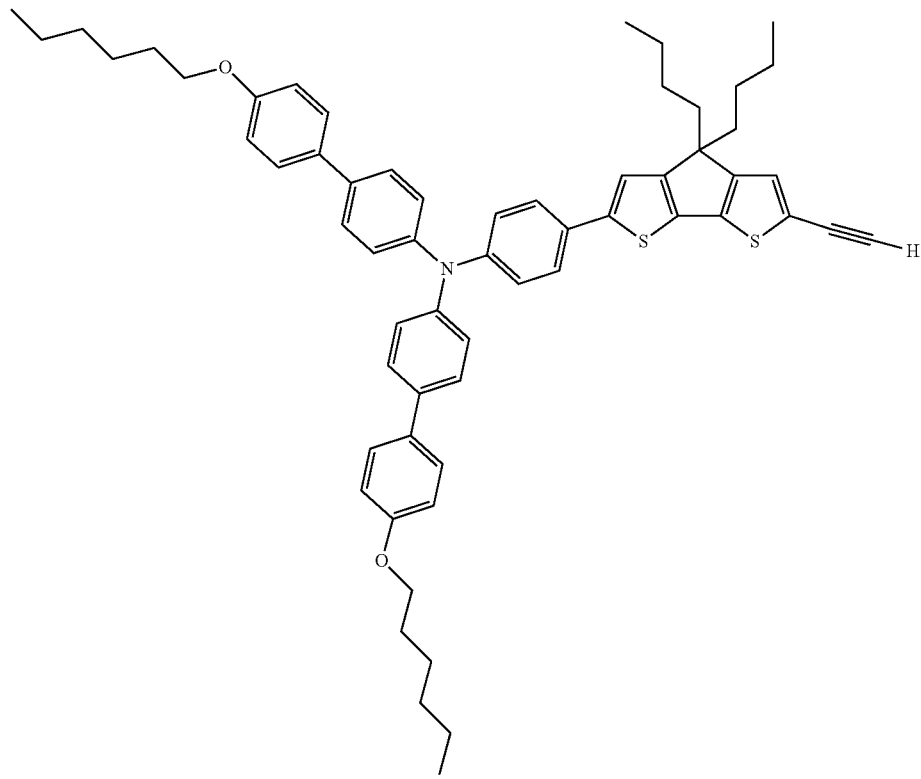

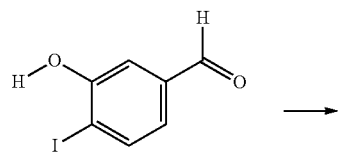

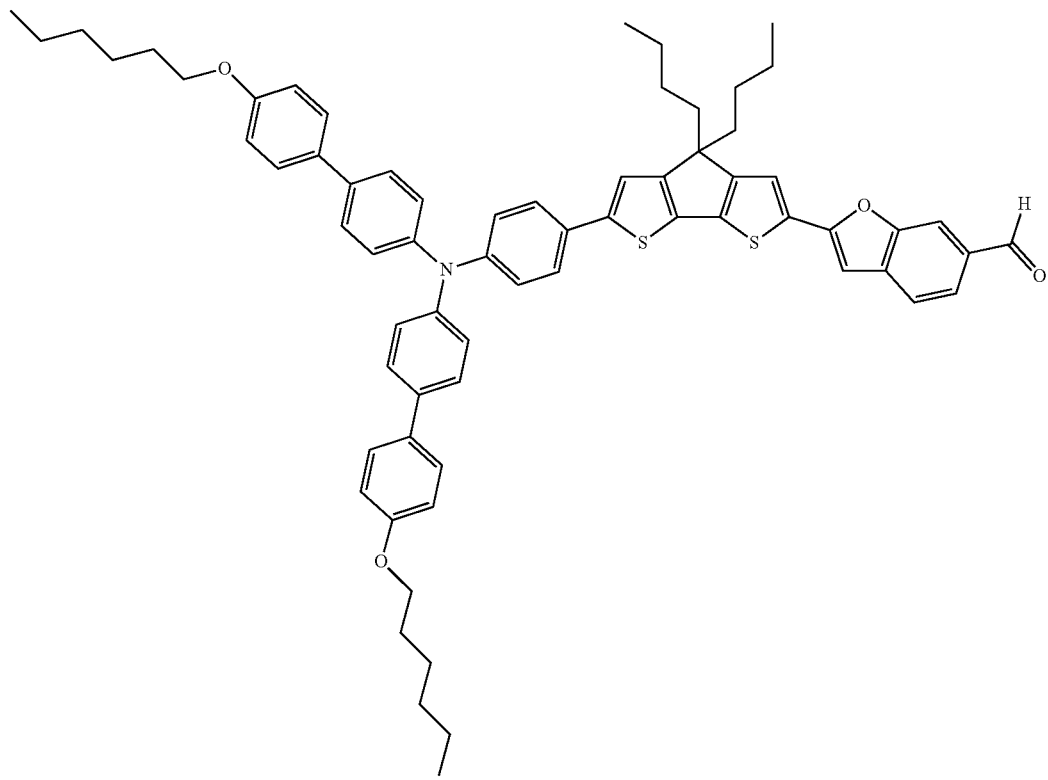

In a round bottom flask, 69 mg (0.0757 mmol) N-[4-(7,7-dibutyl-10-ethynyl-3,11-dithiatricyclo[6.3.0.0²,⁶]undeca-1(8),2(6),4,9-tetraen-4-yl)phenyl]-4-(4-hexoxyphenyl)-N-[4-(4-hexoxyphenyl)phenyl]aniline, 18 mg (0.072 mmol) 3-hydroxy-4-iodobenzaldhyde, 10 mg bis(triphenylphosphine)palladium dichloride and 10 mg CuI was combined in 4 mL triethylamine. Batch was held at 40° C. for 3 h. Reaction mixture was poured into 20 mL water and the mixture was adjusted to pH 6-7 using acetic acid. Product was extracted into methylene chloride. Organic layer was concentrated and product was purified on silica gel (hex/CH$_2$Cl$_2$), yielding 9 mg (0.0087 mmol, 12% yield) orange solid. UV/Vis max 470 nm, LCMS m/z=1031.6. 1H NMR (400 MHz, CDCl$_3$): 9.97 (s, 1H; —CHO), 7.89 (s, 1H; CHarom), 7.68-7.70 (m, 1H; CHarom), 7.53, 7.55 (d, 1H; CHarom), 7.36-7.47 (m, 10H; CHarom), 7.07-7.14 (m, 8H; CHarom), 6.88-6.91 (m, 4H; CHarom), 6.795, 6.798 (d, 1H; CHarom), 3.92 (t, 4H; —OCH2-), 1.83-1.87 (m, 4H; —CH2-), 1.70-1.78 (m, 4H; —CH2-arom), 1.37-1.45 (m, 4H; —CH2-), 1.26-1.31 (m, 8H; —CH2-), 1.10-1.18 (m, 8H; —CH2-), 0.88-0.94 (m, 4H; —CH2-), 0.82-0.86 (m, 6H; —CH3), 0.72 (t, 6H; —CH3).

H. (Z)-2-cyano-3-[2-[7,7-dibutyl-10-[4-[4-(4-hexoxyphenyl)-N-[4-(4-hexoxyphenyl)phenyl]anilino]phenyl]-3,11-dithiatricyclo[6.3.0.02,6]undeca-1(8),2(6),4,9-tetraen-4-yl]benzofuran-6-yl]prop-2-enoic acid
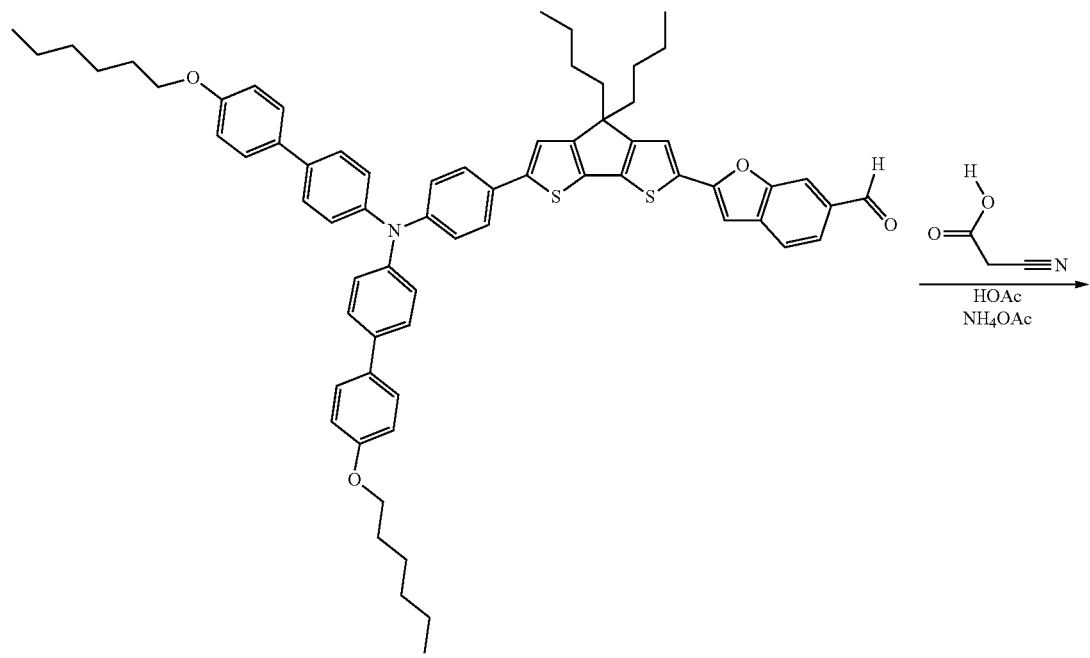
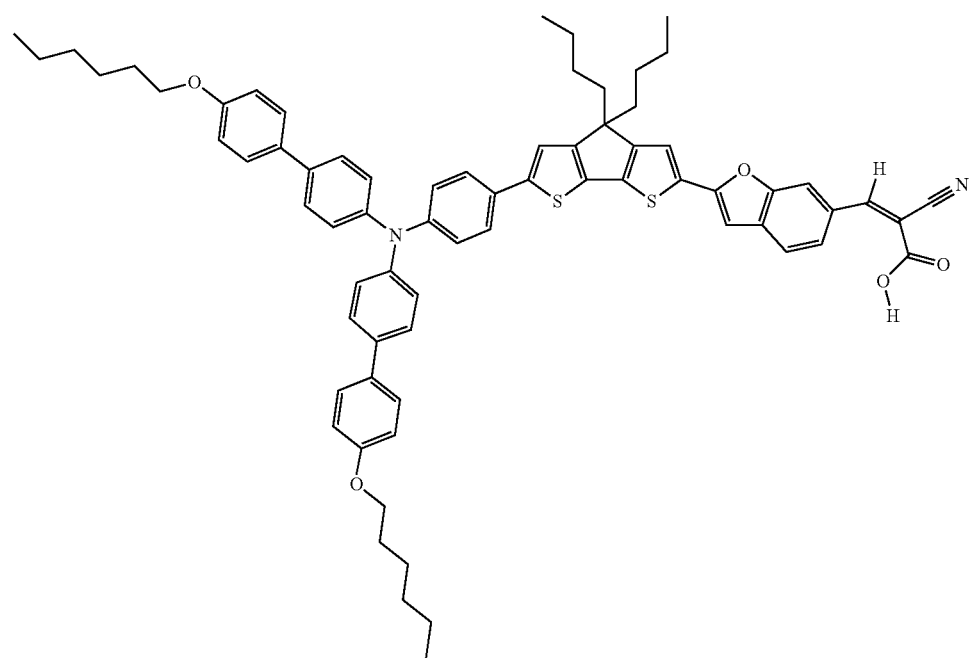

In a round bottom flask, 9 mg (0.0087 mmol) 2-[7,7-dibutyl-10-[4-[4-(4-hexoxyphenyl)-N-[4-(4-hexoxyphenyl)phenyl]anilino]phenyl]-3,11-dithiatricyclo[6.3.0.02,6]undeca-1(8),2(6),4,9-tetraen-4-yl]benzofuran-6-carbaldehyde, 5 mg (0.06 mmol) cyanoacetic acid and 15 mg (0.19 mmol) ammonium acetate was combined in 5 mL acetic acid. Batch was held at reflux for 8 h. 20 mL of water was added and product was extracted into methylene chloride, yielding 10.3 mg red solid. UV/Vis max 500 nm, LCMS m/z=1098.4.

Example 11. Synthesis of (Z)-2-cyano-3-[2-[9,9-dibutyl-7-[4-(N-phenylanilino)phenyl]fluoren-2-yl]benzofuran-6-yl]prop-2-enoic acid (D15)

A. 2,7-dibromo-9,9-dibutyl-fluorene

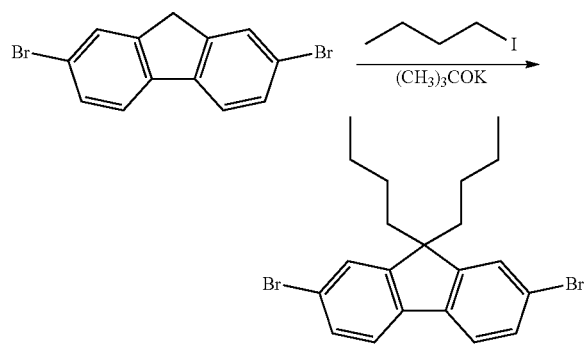

To a 50 mL flask, 2,7-dibromofluorene (2.50 g, 7.76 mmol) and anhydrous tetrahydrofuran (30 mL) were added and cooled to 0° C. To this reaction mixture sodium tert-butoxide (1.86 g, 19.41 mmol) was added and stirred for 30 min at 0° C., then n-iodobutane (3.21 g, 17.47 mmol) was added slowly to it. The reaction temperature was brought to room temperature and mixture was stirred overnight. To terminate the reaction, cold water (20 mL) was added and then extracted with ethylacetate. Organic layer was dried over anhydrous sodium sulfate and concentrated. The residue was purified by chromatography on silica gel (hexane is the elutant) to afford 2,7-dibromo-9,9-dibutyl-fluorene (2.5 g). UV/Vis max 280 nm.

B. 4-(7-bromo-9,9-dibutyl-fluoren-2-yl)-N,N-diphenyl-aniline

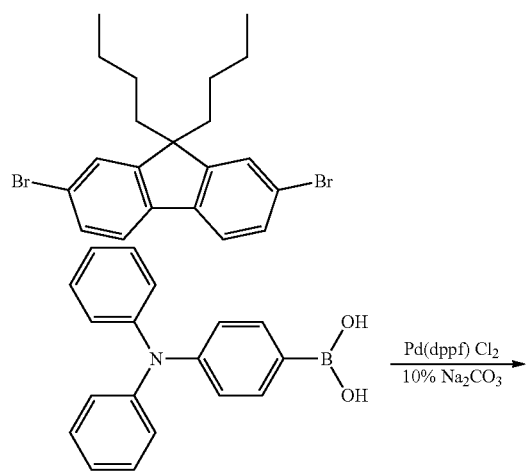

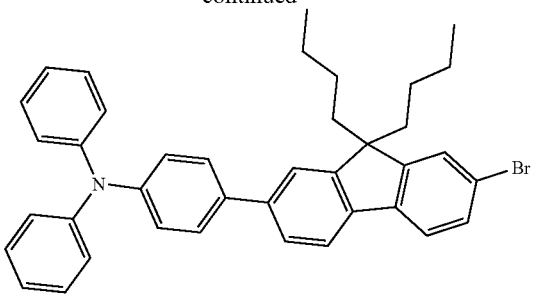

2,7-dibromo-9,9-dibutyl-fluorene (0.36 g, 0.83 mmol), [4-(N-phenylanilino)phenyl]boronic acid (0.08 g, 0.27 mmol), [1,1'-Bis(diphenylphosphino)ferrocene]dichloropalladium(II) (0.04 g, 0.05 mmol), 10% aqueous sodium carbonate solution (6 mL), and tetrahydrofuran (15 mL) were added into a 20 mL microwave vial and reacted for 15 min at 100° C. by microwave. The reaction mixture was extracted with ethylacetate (15 mL) and organic layer was washed with water (10 mL) and brine solution (10 mL), respectively. Organic layer was dried over anhydrous sodium sulfate and concentrated. This crude was purified using column chromatography on silica gel (0 to 10% ethyl acetate in hexanes) to obtain 4-(7-bromo-9,9-dibutyl-fluoren-2-yl)-N,N-diphenyl-aniline (0.08 g). UV/Vis max 350 nm, LCMS m/z=600.

C. 4-[9,9-dibutyl-7-(2-trimethylsilylethynyl)fluoren-2-yl]-N,N-diphenyl-aniline

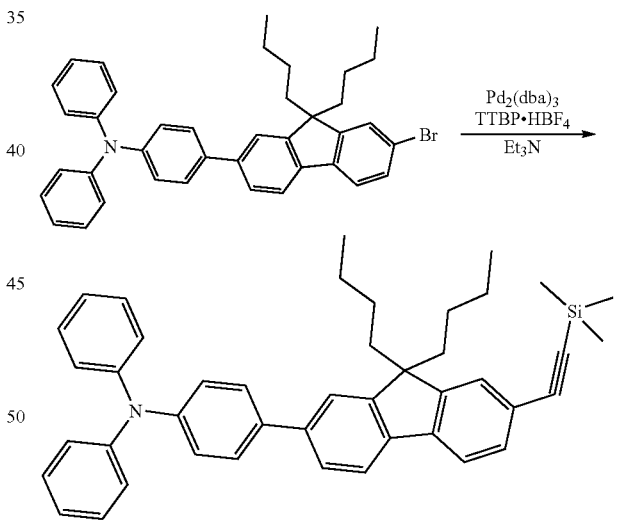

To a 50 mL flask Tris(dibenzylideneacetone)dipalladium (0) (0.28 g, 0.30 mmol), Tri-tert-butylphosphonium tetrafluoroborate (0.087 g, 0.30 mmol), 4-(7-bromo-9,9-dibutyl-fluoren-2-yl)-N,N-diphenyl-aniline (0.9 g, 1.50 mmol), trimethylsislyacetylene (0.44 g, 4.50 mmol) and triethylamine (0. G, mmol) were added under nitrogen. The reaction mixture was stirred for 20 h at 45° C. The reaction mixture was extracted with ethylacetate (30 mL) and washed with water (10 mL) and brine solution (10 mL). Organic layer was dried over anhydrous sodium sulfate and concentrated. The crude product was purified using column chromatography on silica gel (0 to 10% ethylacetate in hexanes)

to obtain 4-[9,9-dibutyl-7-(2-trimethylsilylethynyl)fluoren-2-yl]-N,N-diphenyl-aniline (0.72 g). UV/Vis max 350 nm, LCMS m/z=618.

D. 4-(9,9-dibutyl-7-ethynyl-fluoren-2-yl)-N,N-diphenyl-aniline

E. 2-[9,9-dibutyl-7-[4-(N-phenylanilino)phenyl]fluoren-2-yl]benzofuran-6-carbaldehyde

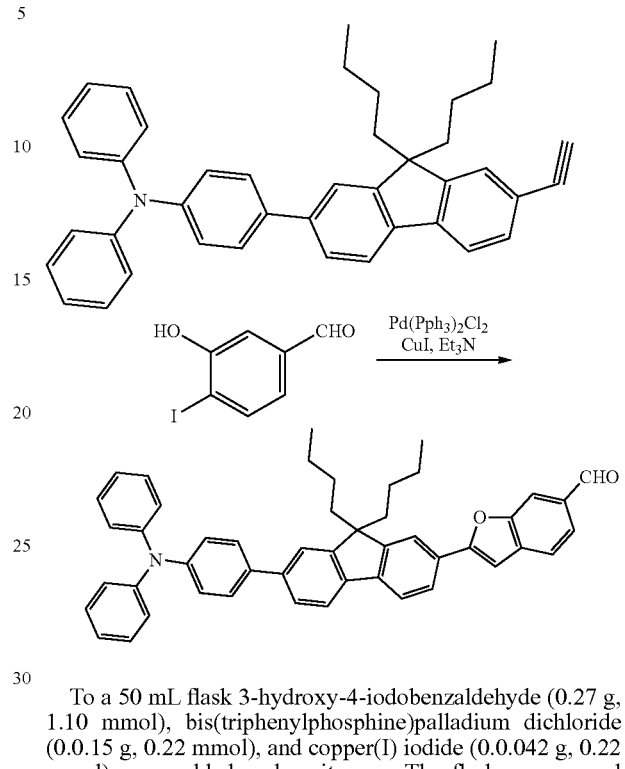

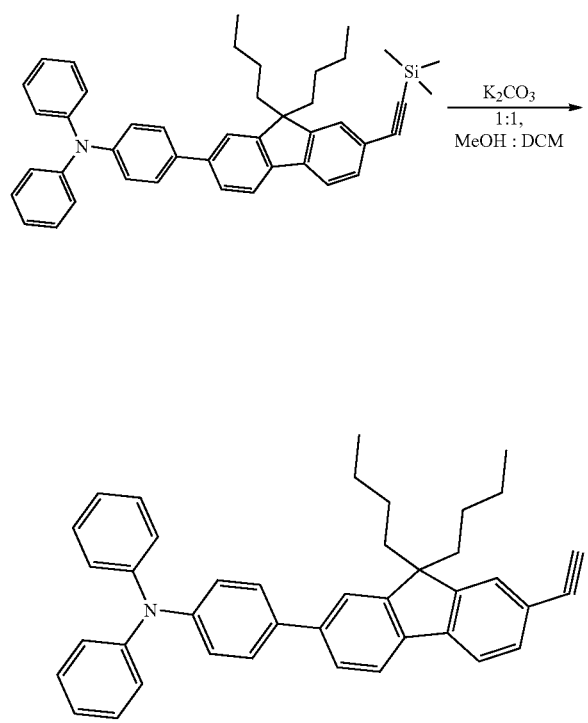

4-[9,9-dibutyl-7-(2-trimethylsilylethynyl)fluoren-2-yl]-N,N-diphenyl-aniline (0.72 g, 1.17 mmol) was added to a 50 mL flask, then dichloromethane (10 mL) and methanol (10 mL) were added under nitrogen. To this reaction mixture, anhydrous K₂CO₃ (0.64 g, 4.66 mmol) was added and stirred for 3 h. The reaction mixture evaporated and the resulting crude product was dissolved in dichloromethane (30 mL) and filtered through the filtering funnel and mother liquor concentrated to obtain 4-(9,9-dibutyl-7-ethynyl-fluoren-2-yl)-N,N-diphenyl-aniline (0.62 g). UV/Vis max 350 nm, LCMS m/z=546.

To a 50 mL flask 3-hydroxy-4-iodobenzaldehyde (0.27 g, 1.10 mmol), bis(triphenylphosphine)palladium dichloride (0.0.15 g, 0.22 mmol), and copper(I) iodide (0.0.042 g, 0.22 mmol) were added under nitrogen. The flask was purged with nitrogen for 20 min, then a solution of 4-(9,9-dibutyl-7-ethynyl-fluoren-2-yl)-N,N-diphenyl-aniline (0.60 g, 1.10 mmol) in triethylamine (15 mL) degassed with nitrogen was added. The reaction was heated at 50° C. for 3 h, then cooled down to room temperature and quenched with water (25 mL). The reaction mixture was extracted with ethyl acetate (30 mL) and the organic layer washed with brine solution and dried over sodium sulfate. The organic layer was filtered and concentrated. Crude product was purified using chromatography on silica gel (0 to 13% ethyl acetate in hexanes) to afford 2-[9,9-dibutyl-7-[4-(N-phenylanilino)phenyl]fluoren-2-yl]benzofuran-6-carbaldehyde (0.2 g). UV/Vis max 395 nm, LCMS m/z=666.

F. (Z)-2-cyano-3-[2-[9,9-dibutyl-7-[4-(N-phenylanilino)phenyl]fluoren-2-yl]benzofuran-6-yl]prop-2-enoic acid

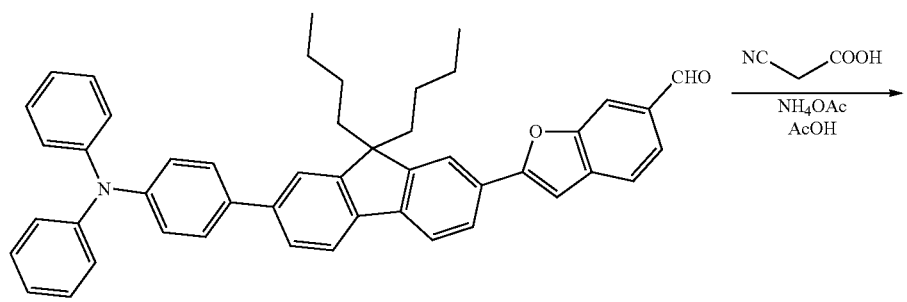

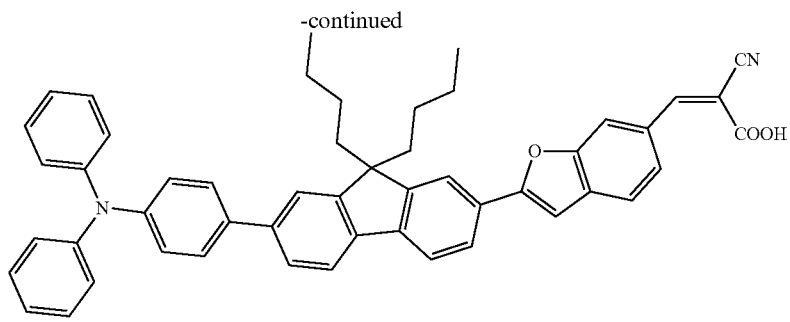

Acetic acid (5.0 mL) was added to 2-[9,9-dibutyl-7-[4-(N-phenylanilino)phenyl]fluoren-2-yl]benzofuran-6-carbaldehyde (0.2 g, 0.30 mmol), cyanoacetic acid (0.127 g, 1.50 mmol), and ammonium acetate (0.23 g, 3.0 mmol) and the reaction was heated to reflux for 1.5 h. The reaction was cooled to room temperature and diluted with dichloromethane (35 mL). The dichloromethane (35 mL) was washed with water (2×10 mL) and brine solution (10 mL). The organic layer dried over anhydrous sodium sulfate and concentrated to afford (Z)-2-cyano-3-[2-[9,9-dibutyl-7-[4-(N-phenylanilino)-phenyl]fluoren-2-yl]benzofuran-6-yl] prop-2-enoic acid (0.17 g), unidentified olefin isomer. UV/Vis max 425 nm, LCMS m/z=733.

Example 12. Synthesis of (E)-2-cyano-3-[2-[7-[4-[4-(4-hexoxyphenyl)-N-[4-(4-hexoxyphenyl)phenyl] anilino]phenyl]-9,9-dioctyl-fluoren-2-yl]benzofuran-6-yl]prop-2-enoic acid (D13)

A. 2,7-dibromo-9,9-dioctyl-fluorene

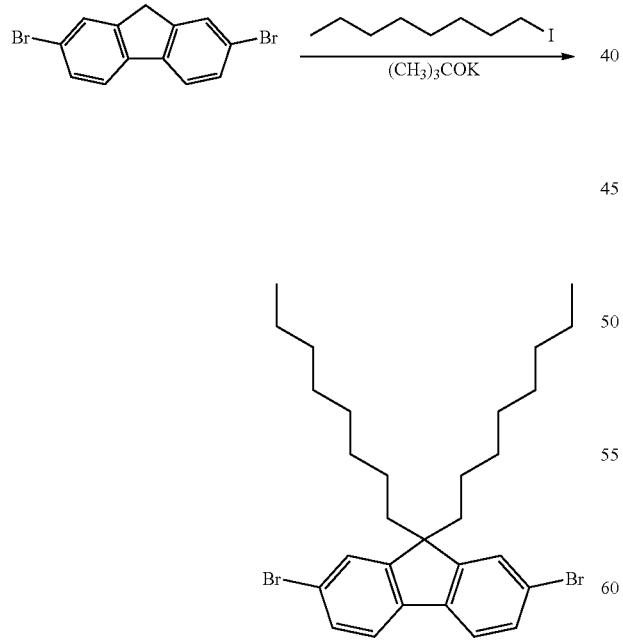

To a 50 mL flask, 2,7-dibromofluorene (4.0 g, 12.4 mmol) and anhydrous tetrahydrofuran (60 mL) were added and cooled to 0° C. To this reaction mixture, potassium tert-butoxide (3.48 g, 31.06 mmol) was added and stirred for 30 min at 0° C. and then n-iodooctane (6.56 g, 27.34 mmol) was added slowly. The reaction temperature was brought to room temperature stirred overnight. To terminate the reaction, cold water (20 mL) was added and then extracted with ethylacetate. Organic layer was dried over anhydrous sodium sulfate and concentrated. The residue was purified by chromatography on silica gel (hexane is the elutant) to afford 2,7-dibromo-9,9-dioctyl-fluorene (6.0 g). UV/Vis max 280 nm.

B. N-[4-(7-bromo-9,9-dioctyl-fluoren-2-yl)phenyl]-4-(4-hexoxyphenyl)-N-[4-(4-hexoxyphenyl)phenyl] aniline

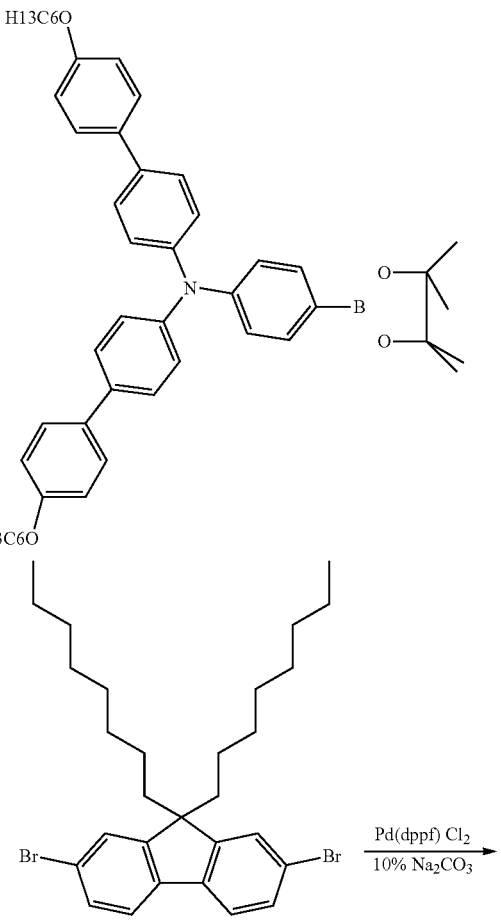

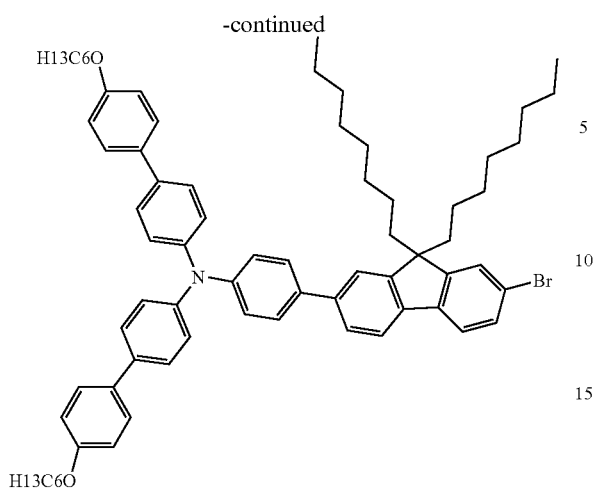

2,7-dibromo-9,9-dioctyl-fluorene (0.34 g, 0.62 mmol), N,N-bis[4-(4-hexoxyphenyl)phenyl]-4-(4,4,5,5-tetramethyl-1,3,2-dioxaborolan-2-yl)aniline (0.15 g, 0.20 mmol), [1,1'-Bis(diphenylphosphino)ferrocene]dichloropalladium (II) (0.03 g, 0.04 mmol), 10% aqueous sodium carbonate solution (6 mL), and tetrahydrofuran (15 mL) were added to a 20 mL microwave vial and reacted for 15 min at 100° C. by microwave. The reaction mixture was extracted with ethylacetate (15 mL) and organic layer washed with water (10 mL) and brine solution (10 mL), respectively. Organic layer was dried over anhydrous sodium sulfate and concentrated. The crude product was purified using column chromatography on silica gel (0 to 10% ethyl acetate in hexanes) to obtain N-[4-(7-bromo-9,9-dioctyl-fluoren-2-yl)phenyl]-4-(4-hexoxyphenyl)-N-[4-(4-hexoxyphenyl)phenyl]aniline (0.07 g). UV/Vis max 350 nm, LCMS m/z=1064.

C. N-[4-[9,9-dioctyl-7-(2-trimethylsilylethynyl)fluoren-2-yl]phenyl]-4-(4-hexoxyphenyl)-N-[4-(4-hexoxyphenyl)phenyl]aniline

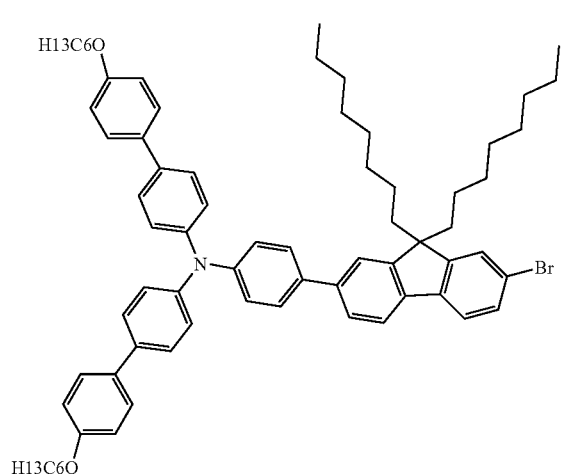

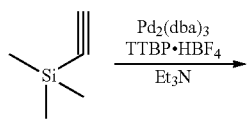

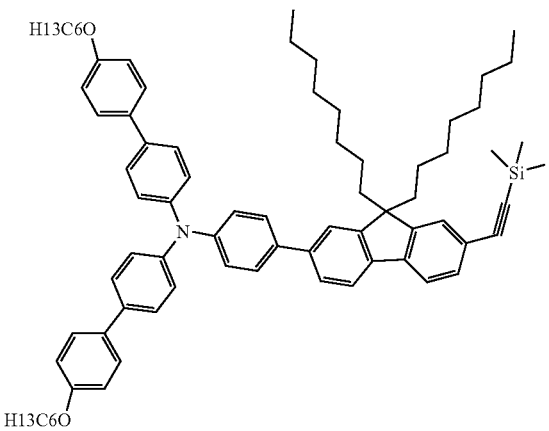

To a 50 mL flask Tris(dibenzylideneacetone)dipalladium (0) (0.09 g, 0.10 mmol), Tri-tert-butylphosphonium tetrafluoroborate ((0.03 g, 0.10 mmol), N-[4-(7-bromo-9,9-dioctyl-fluoren-2-yl)phenyl]-4-(4-hexoxyphenyl)-N-[4-(4-hexoxyphenyl)phenyl]aniline (0.55 g, mmol), trimethylsilylacetylene (0.15 g, 1.55 mmol) and triethylamine (15 mL) were added under nitrogen. The reaction mixture was stirred for 20 h at 45° C. The reaction mixture was extracted with ethylacetate (30 mL) and washed with water (10 mL) and brine solution (10 mL). Organic layer was dried over anhydrous sodium sulfate and concentrated. The crude product was purified using column chromatography on silica gel (0 to 10% ethylacetate in hexanes) to obtain N-[4-[9,9-dioctyl-7-(2-trimethylsilylethynyl)fluoren-2-yl]phenyl]-4-(4-hexoxyphenyl)-N-[4-(4-hexoxyphenyl)phenyl]aniline (0.37 g). UV/Vis max 350 nm, LCMS m/z=1082.

D. N-[4-(7-ethynyl-9,9-dioctyl-fluoren-2-yl)phenyl]-4-(4-hexoxyphenyl)-N-[4-(4-hexoxyphenyl)phenyl] aniline
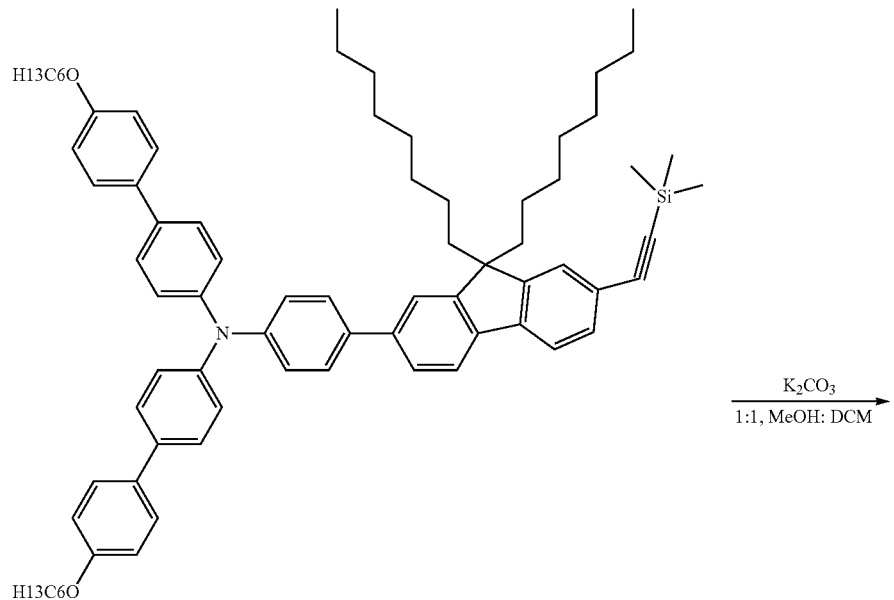
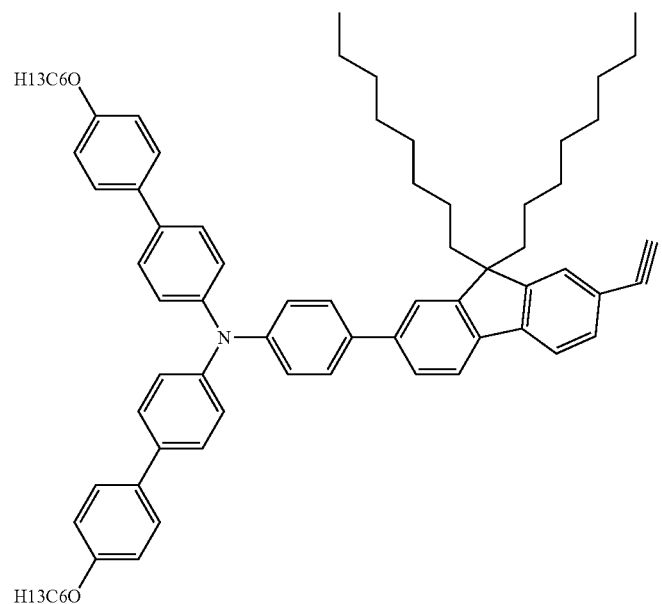

N-[4-[9,9-dioctyl-7-(2-trimethylsilylethynyl)fluoren-2-yl]phenyl]-4-(4-hexoxyphenyl)-N-[4-(4-hexoxyphenyl)phenyl]aniline (0.37 g, 0.34 mmol) was added to a 50 mL flask and then dichloromethane (10 mL) and methanol (10 mL) were added under nitrogen. To this reaction mixture, anhydrous $K_2CO_3$ (0.19 g, 1.30 mmol) was added and stirred for 3 h. The reaction mixture evaporated and the resulting crude product was dissolved in dichloromethane (30 mL) and filtered through filtering funnel and mother liquor concentrated to obtain N-[4-(7-ethynyl-9,9-dioctyl-fluoren-2-yl)phenyl]-4-(4-hexoxyphenyl)-N-[4-(4-hexoxyphenyl)phenyl]aniline (0.32 g). UV/Vis max 350 nm, LCMS m/z=1010.

E. 2-[7-[4-[4-(4-hexoxyphenyl)-N-[4-(4-hexoxyphenyl)phenyl]anilino]phenyl]-9,9-dioctyl-fluoren-2-yl]benzofuran-6-carbaldehyde

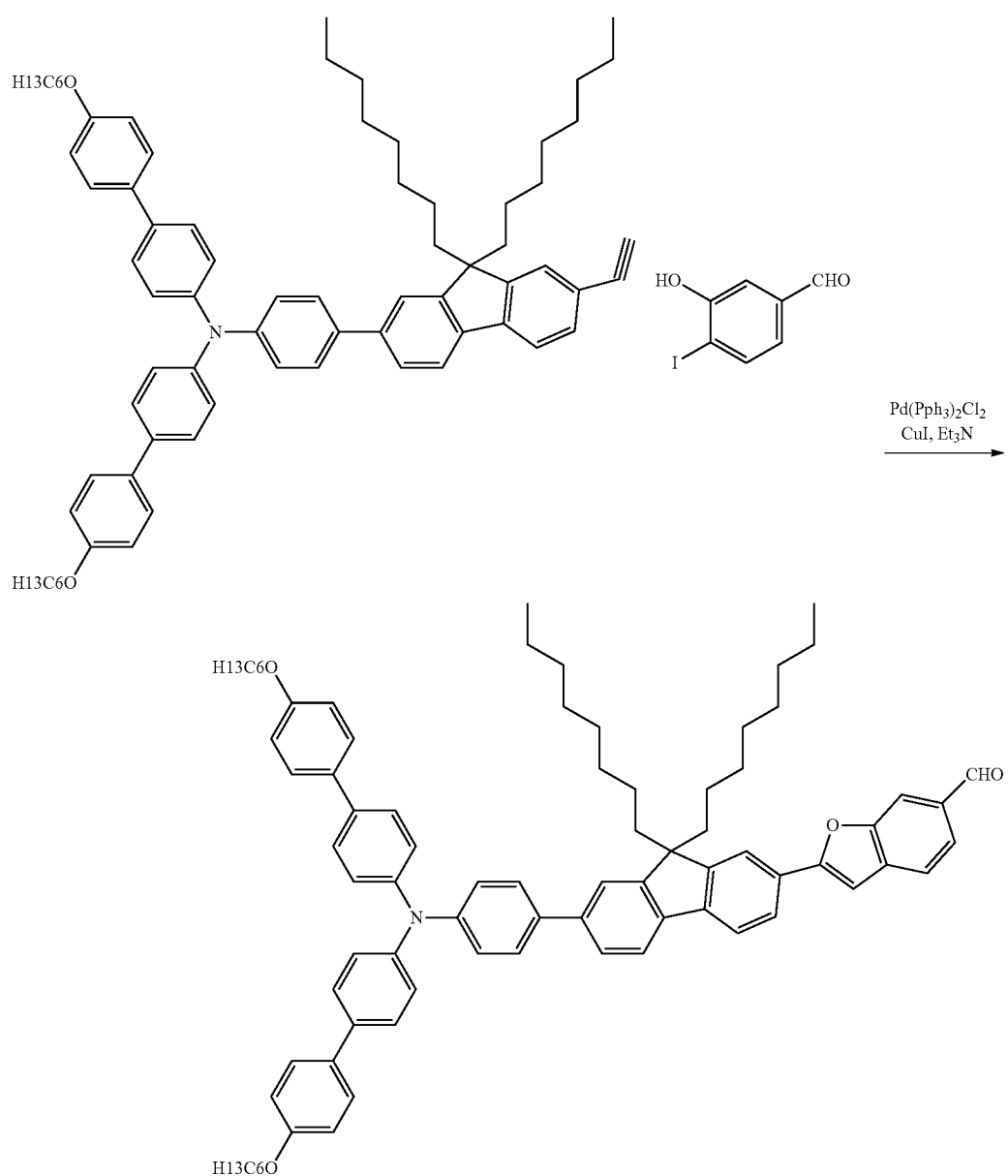

To a 50 mL flask 3-hydroxy-4-iodobenzaldehyde (0.073 g, 0.30 mmol), bis(triphenylphosphine)palladium dichloride (0.043 g, 0.06 mmol), and copper(I) iodide (0.02 g, 0.06 mmol) were added under nitrogen. The flask was purged with nitrogen for 20 min, then a solution of N-[4-(7-ethynyl-9,9-dioctyl-fluoren-2-yl)phenyl]-4-(4-hexoxyphenyl)-N-[4-(4-hexoxyphenyl)phenyl]aniline (0.6 g) in triethylamine (2.18 mL) degassed with nitrogen was added. The reaction was heated at 50° C. for 3 h, cooled down to room temperature, then quenched with water (25 mL). The reaction mixture was extracted with ethyl acetate (30 mL) and organic layer washed with brine solution and dried over sodium sulfate. The organic was filtered and concentrated. Crude product was purified using chromatography on silica gel (0 to 13% ethyl acetate in hexanes) to afford 2-[7-[4-[4-(4-hexoxyphenyl)-N-[4-(4-hexoxyphenyl)phenyl]anilino]phenyl]-9,9-dioctyl-fluoren-2-yl]benzofuran-6-carbaldehyde (0.09 g). UV/Vis max 395 nm, LCMS m/z=1130.

F. (E)-2-cyano-3-[2-[7-[4-[4-(4-hexoxyphenyl)-N-[4-(4-hexoxyphenyl)phenyl]anilino]phenyl]-9,9-dioctyl-fluoren-2-yl]benzofuran-6-yl]prop-2-enoic acid

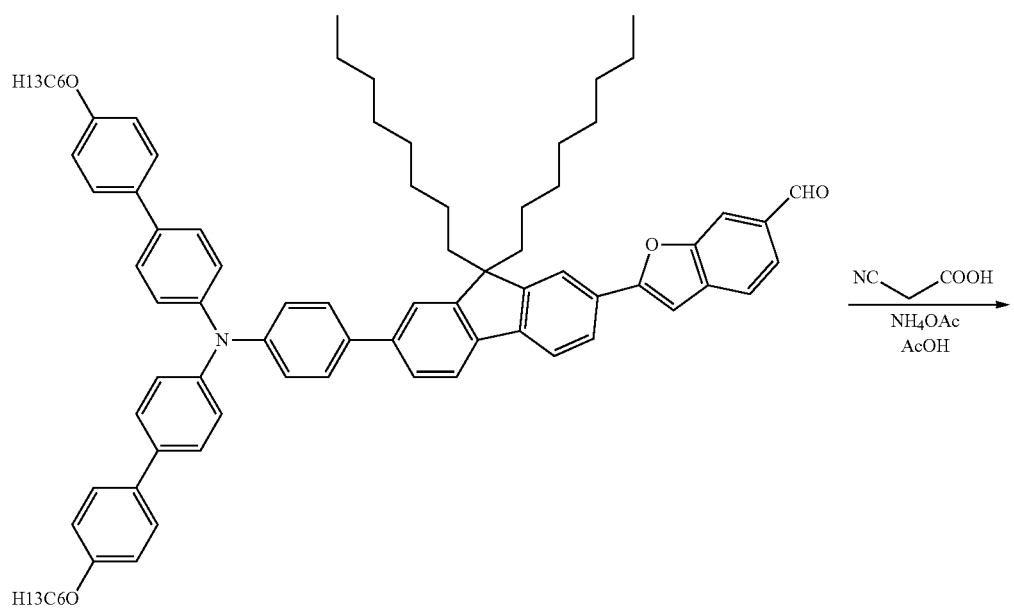

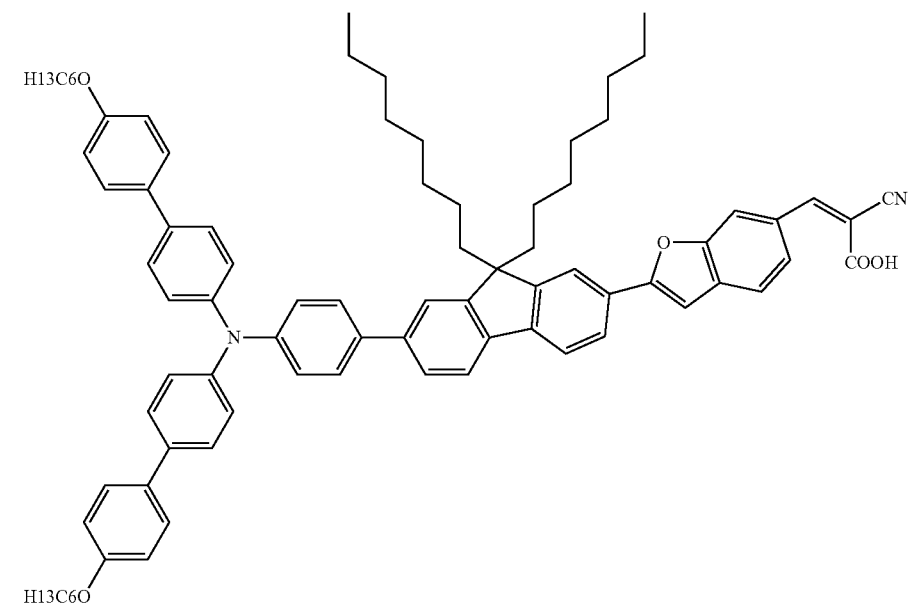

Acetic acid (1.70 mL) was added to 2-[7-[4-[4-(4-hexoxyphenyl)-N-[4-(4-hexoxyphenyl)phenyl]anilino]phenyl]-9,9-dioctyl-fluoren-2-yl]benzofuran-6-carbaldehyde (0.2 g), cyanoacetic acid (0.07 g, 0.9 mmol), and ammonium acetate (0.14 g, 1.80 mmol) in a round bottom flask, and the reaction was heated to reflux for 1.5 h. The reaction was cooled to room temperature and diluted with dichloromethane (35 mL). The dichloromethane (35 mL) was washed with water (2×10 mL) and brine solution (10 mL). The organic layer was dried over anhydrous sodium sulfate and concentrated to afford (E)-2-cyano-3-[2-[7-[4-[4-(4-hexoxyphenyl)-N-[4-(4-hexoxyphenyl)-phenyl]anilino]phenyl]-9,9-dioctyl-fluoren-2-yl]benzofuran-6-yl]prop-2-enoic acid, unidentified olefin isomer. UV/Vis max 425 nm, LCMS m/z=1197.

Example 13. Synthesis of D16

A. N-[4-(7-bromo-9,9-dioctyl-fluoren-2-yl)phenyl]-4-(4-tert-butylphenyl)-N-[4-(4-tert-butylphenyl)phenyl]aniline

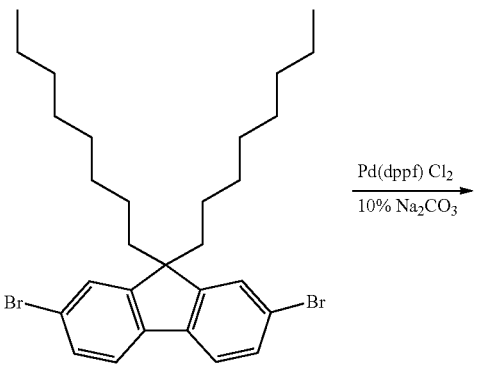

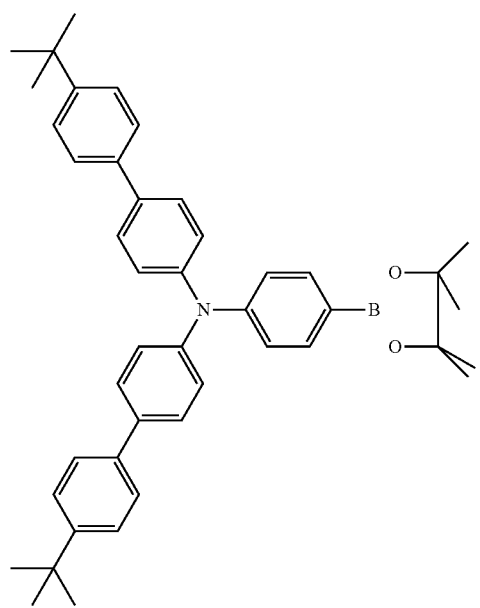

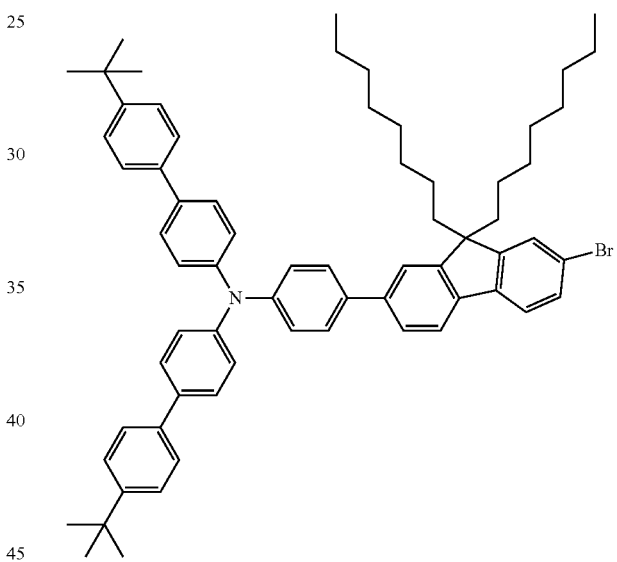

2,7-dibromo-9,9-dioctyl-fluorene (0.75 g, 1.34 mmol) (see Example 12.A), N,N-bis[4-(4-tert-butylphenyl)phenyl]-4-(4,4,5,5-tetramethyl-1,3,2-dioxaborolan-2-yl)aniline (0.25 g, 0.40 mmol) (see Example 2.C), [1,1'-bis(diphenylphosphino)ferrocene]dichloro-palladium(II) (0.08 g, 0.57 mmol), 10% aqueous sodium carbonate solution (5 mL), and tetrahydrofuran (15 mL) were added in a 20 mL microwave vial and reacted for 15 min at 100° C. by microwave. The reaction mixture was extracted with ethylacetate (15 mL) and organic layer washed with water (10 mL) and brine solution (10 mL), respectively. Organic layer was dried over anhydrous sodium sulfate and concentrated. The crude product was purified using column chromatography on silica gel (0 to 10% ethyl acetate in hexanes) to obtain N-[4-(7-bromo-9,9-dioctyl-fluoren-2-yl)phenyl]-4-(4-tert-butylphenyl)-N-[4-(4-tert-butylphenyl)phenyl]aniline (0.2 g). UV/Vis max 350 nm, LCMS m/z=976.

B. 4-(4-tert-butylphenyl)-N-[4-(4-tert-butylphenyl)phenyl]-N-[4-[9,9-dioctyl-7-(2-trimethylsilylethynyl)fluoren-2-yl]phenyl]aniline

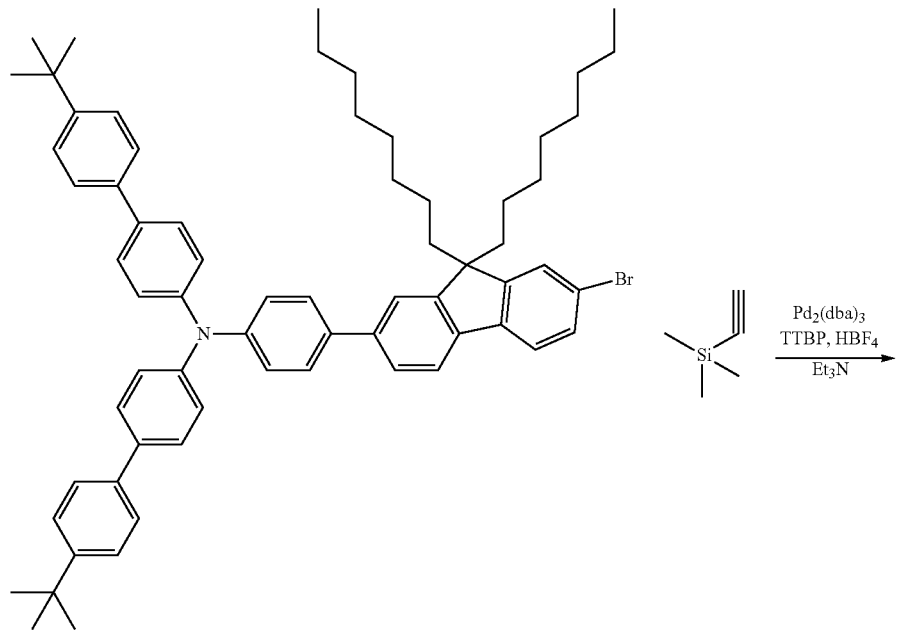

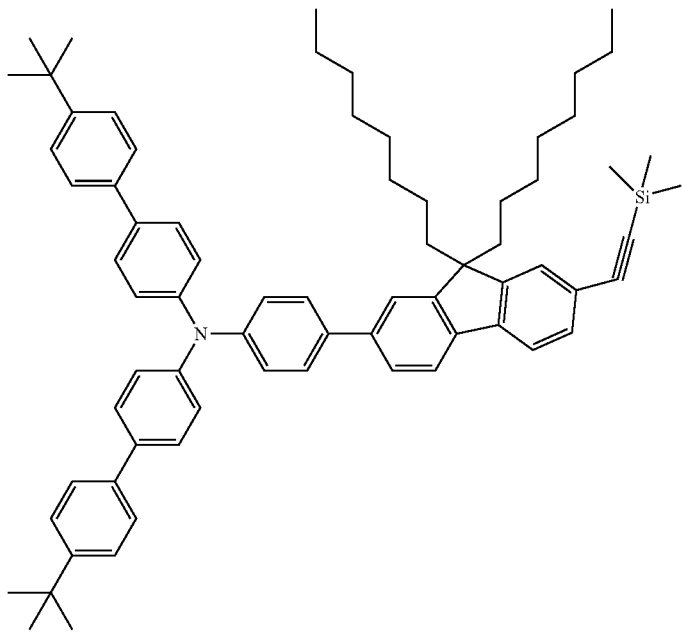

To a 50 mL flask Tris(dibenzylideneacetone)dipalladium (0) (0.09 g, 0.10 mmol), Tri-tert-butylphosphonium tetrafluoroborate (0.03 g, 0.10 mmol), N-[4-(7-bromo-9,9-dioctyl-fluoren-2-yl)phenyl]-4-(4-tert-butylphenyl)-N-[4-(4-tert-butylphenyl)phenyl]aniline (0.50 g, 0.51 mmol), trimethylsilylacetylene (0.15 g, 1.50 mmol) and triethylamine (15 mL) were added under nitrogen. The reaction mixture was stirred for 20 h at 45° C. The reaction mixture extracted with ethylacetate (30 mL) and washed with water (10 mL) and brine solution (10 mL). Organic layer was dried over anhydrous sodium sulfate and concentrated. The crude product was purified using column chromatography on silica gel (0 to 10% ethylacetate in hexanes) to obtain 4-(4-tert-butylphenyl)-N-[4-(4-tert-butylphenyl)phenyl]-N-[4-[9,9-dioctyl-7-(2-trimethylsilylethynyl)fluoren-2-yl]phenyl]aniline (0.34 g). UV/Vis max 350 nm, LCMS m/z=994.

C. 4-(4-tert-butylphenyl)-N-[4-(4-tert-butylphenyl)phenyl]-N-[4-(7-ethynyl-9,9-dioctyl-fluoren-2-yl)phenyl]aniline

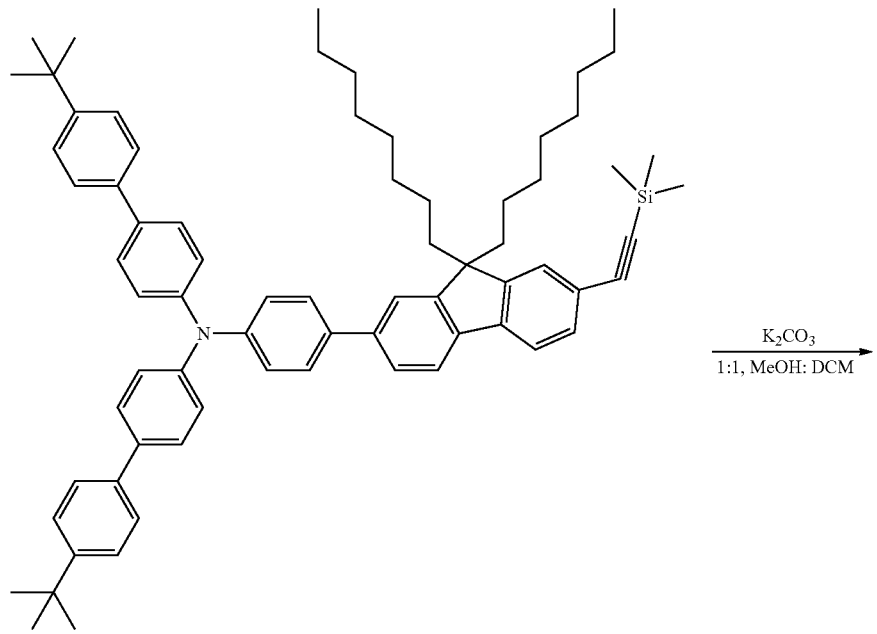

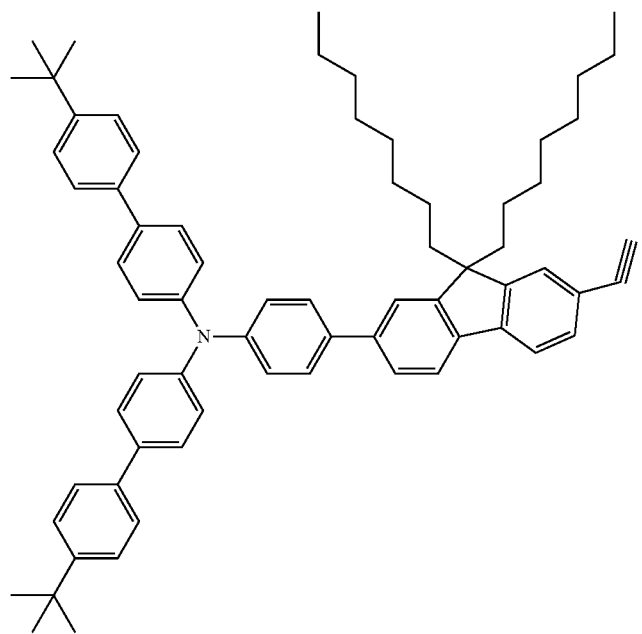

4-(4-tert-butylphenyl)-N-[4-(4-tert-butylphenyl)phenyl]-N-[4-[9,9-dioctyl-7-(2-trimethylsilylethynyl)fluoren-2-yl]phenyl]aniline (0.30 g, 0.32 mmol) was added to a 50 mL flask and then dichloromethane (10 mL) and methanol (10 mL) were added under nitrogen. To this reaction mixture anhydrous $K_2CO_3$ (0.17 g, 1.20 mmol) was added and stirred for 3 h. The reaction mixture evaporated and the resulting crude product was dissolved in dichloromethane (30 mL) and filtered through filtering funnel and mother liquor concentrated to obtain 4-(4-tert-butylphenyl)-N-[4-(4-tert-butylphenyl)phenyl]-N-[4-(7-ethynyl-9,9-dioctyl-fluoren-2-yl)phenyl]aniline (0.27 g). UV/Vis max 350 nm, LCMS m/z=922.

D. 2-[7-[4-[N-[4-(4-tert-butylphenyl)phenyl]-4-[(1E,3E)-5,5-dimethylhexa-1,3-dienyl]anilino]phenyl]-9,9-dioctyl-fluoren-2-yl]benzofuran-6-carbaldehyde

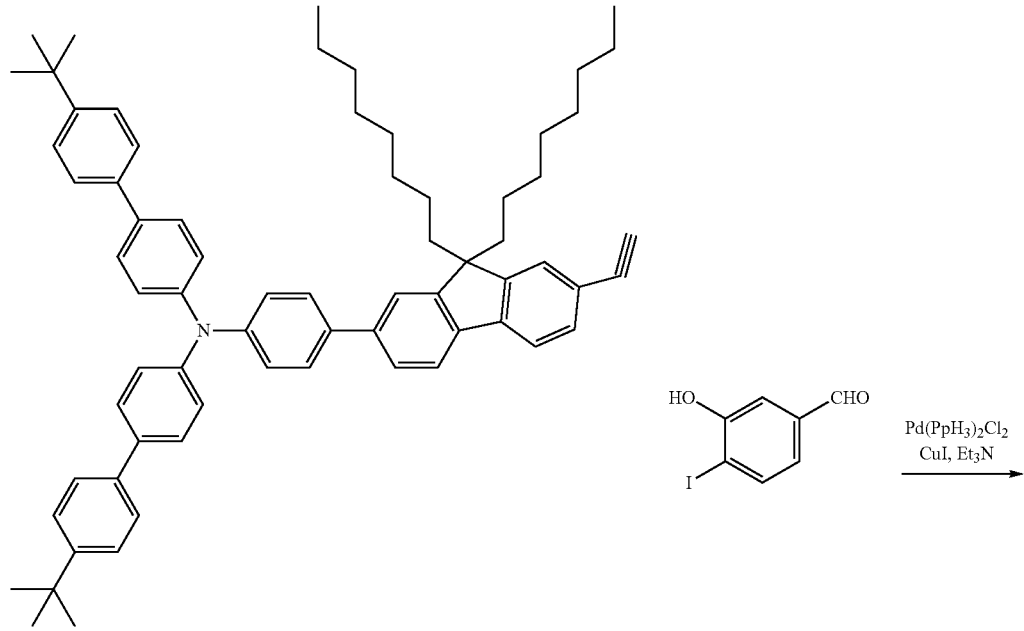

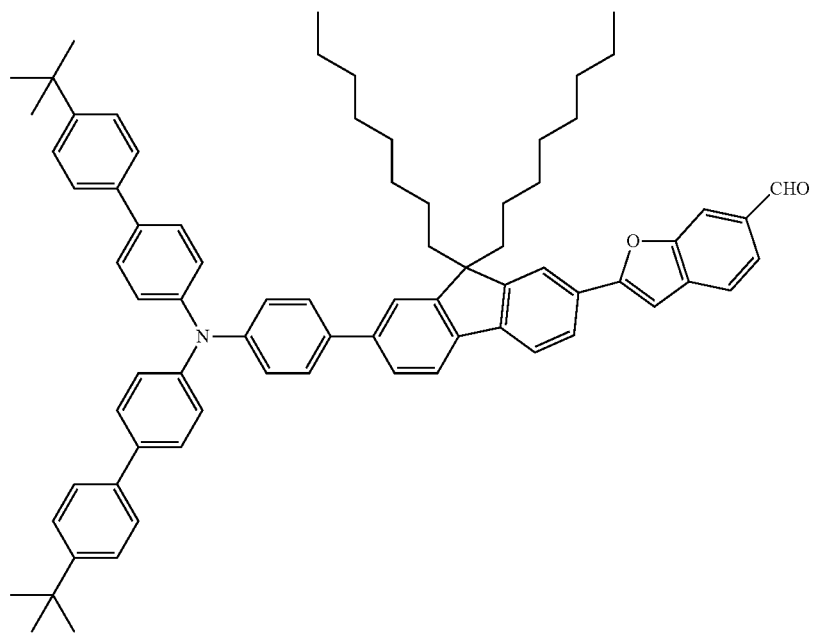

To a 50 mL flask, 3-hydroxy-4-iodobenzaldehyde (0.07 g, 0.08 mmol), bis(triphenylphosphine)palladium dichloride (0.04 g, 0.06 mmol), and copper(I) iodide (0.01 g, 0.06 mmol) were added under nitrogen. The flask was purged with nitrogen for 20 min and then added a solution of 4-(4-tert-butylphenyl)-N-[4-(4-tert-butylphenyl)phenyl]-N-[4-(7-ethynyl-9,9-dioctyl-fluoren-2-yl)phenyl]aniline (0.27 g, 0.30 mmol) in triethylamine (10 mL) which was degassed by bubbling nitrogen through for 20 min. The reaction was heated at 50° C. for 3 h. The reaction was cooled down to room temperature and then reaction quenched with water (25 mL). The reaction mixture extracted with ethyl acetate (30 mL) and organic layer washed with brine solution and dried over sodium sulfate. The organic was filtered and concentrated. Crude product was purified using chromatography on silica gel (0 to 13% ethyl acetate in hexanes) to afford 2-[7-[4-[N-[4-(4-tert-butylphenyl)phenyl]-4-[(1E,3E)-5,5-dimethylhexa-1,3-dienyl]anilino]phenyl]-9,9-dioctyl-fluoren-2-yl]benzofuran-6-carbaldehyde (0.045 g). UV/Vis max 395 nm, LCMS m/z=1042.

(Z)-3-[2-[7-[4-[4-(4-tert-butylphenyl)-N-[4-(4-tert butylphenyl)phenyl]anilino]phenyl]-9,9-dioctyl-fluoren-2-yl]benzofuran-6-yl]-2-cyano-prop-2-enoic acid
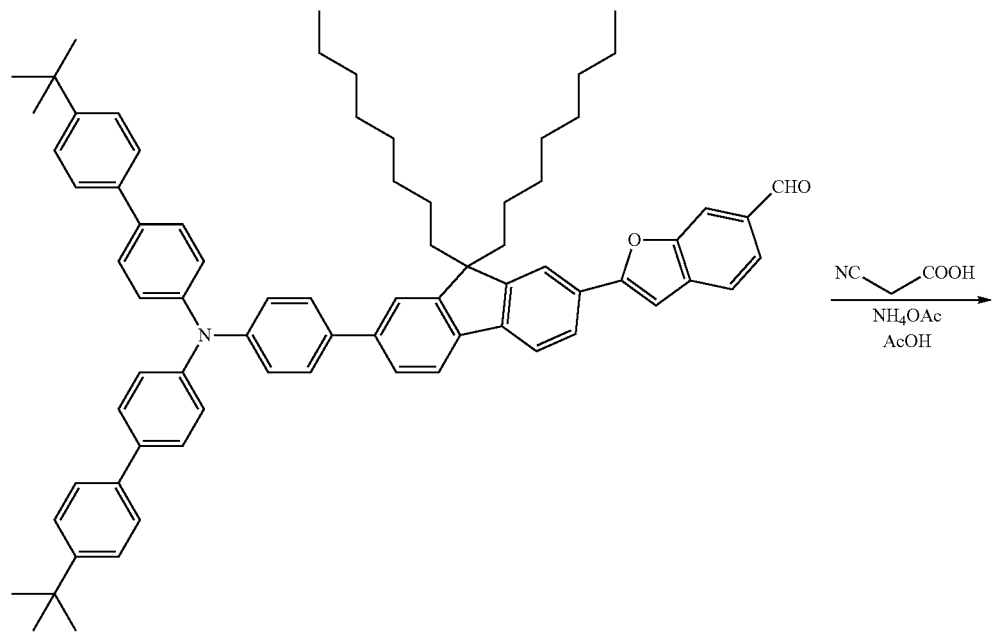
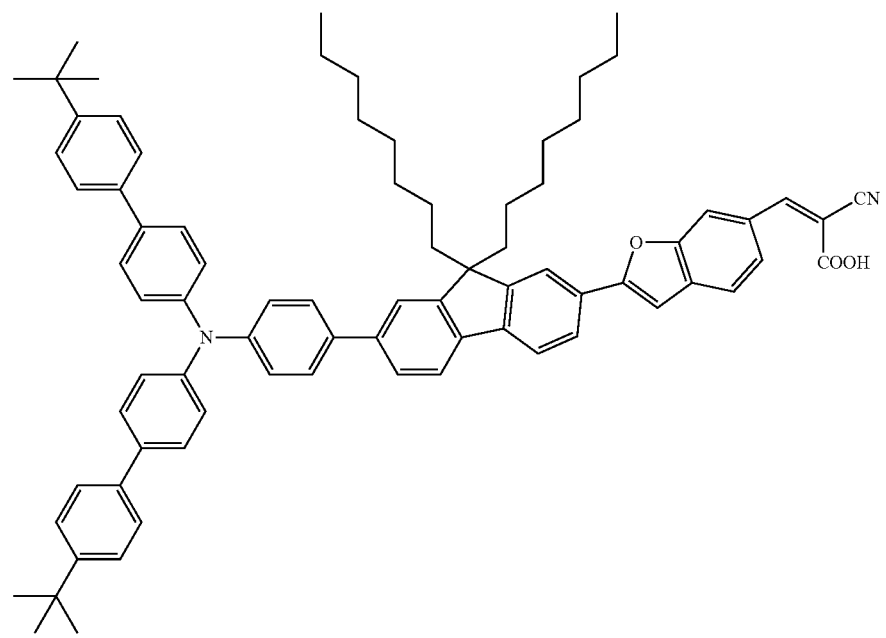

Acetic acid (4 mL) was added to 2-[7-[4-[N-[4-(4-tert-butylphenyl)phenyl]-4-[(1E,3E)-5,5-dimethylhexa-1,3-dienyl]anilino]phenyl]-9,9-dioctyl-fluoren-2-yl]benzofuran-6-carbaldehyde (0.045 g, 0.043 mmol), cyanoacetic acid (0.02 g, 0.2 mmol), and ammonium acetate (0.03 g, 0.43 mmol) and the reaction was heated to reflux for 1.5 h. The reaction was cooled to room temperature and diluted with dichloromethane (25 mL). The dichloromethane layer was washed with water (2×10 mL) and brine solution (10 mL). The organic layer was dried over anhydrous sodium sulfate and concentrated to afford 4-(4-tert-butylphenyl)-N-[4-(4-tert-butylphenyl)phenyl]-N-[4-[9,9-dioctyl-7-(6-vinylbenzofuran-2-yl)fluoren-2-yl]phenyl]aniline (0.03 g), unidentified olefin isomer. UV/Vis max 425 nm, LCMS m/z=1109.

Example 14. Synthesis of (Z)-2-cyano-3-[2-[2-[4-(N-phenylanilino)phenyl]-ethynyl]benzofuran-6-yl]prop-2-enoic acid (D7)

A. 2-bromoethynyl(trimethyl)silane

n-BuLi was added dropwise to a stirred solution of ethynyl(trimethyl)silane (2.0 g, 20.40 mmol) in THF (25 mL) at −78° C., then stirred further for 30 min at −78° C. To this reaction mixture, bromine (3.26 g, 20.40 mmol) was added dropwise at −78° C. and stirring was continued 30 more min. Reaction was quenched with aqueous $NaS_2O_3$ (5 mL) and then warmed to room temperature. Reaction mixture was extracted with diethyl ether (30 mL), then the organic layers were combined and concentrated to obtain 2-bromoethynyl(trimethyl)silane (3.5 g). LCMS m/z=175.

B. N,N-diphenyl-4-(4-trimethylsilylbuta-1,3-diynyl)aniline

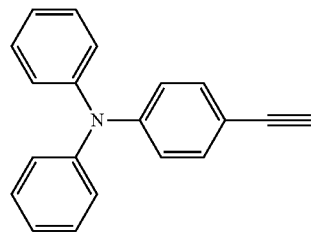

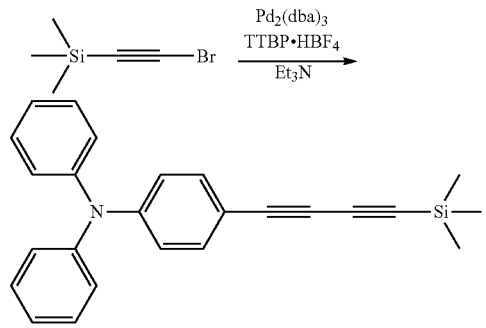

To a 50 mL flask Tris(dibenzylideneacetone)dipalladium (0) (1.02 g, 1.11 mmol), Tri-tert-butylphosphonium tetrafluoroborate (0.32 g, 1.11 mmol) 4-ethynyl-N,N-diphenylaniline (1.50 g, 5.57 mmol), 2-bromoethynyl(trimethyl)silane (0.98 g, 5.57 mmol), triethylamine (15 mL), and anhydrous tetrahydrofuran (15 mL) were added under nitrogen. The reaction mixture was stirred for 20 h at room temperature. The reaction mixture extracted with ethylacetate (30 mL) and washed with water (10 mL) and brine solution (10 mL). Organic layer was dried over anhydrous sodium sulfate and concentrated. The crude product was purified using column chromatography on silica gel (0 to 5% ethylacetate in hexanes) to obtain N,N-diphenyl-4-(4-trimethylsilylbuta-1,3-diynyl)aniline (1.60 g). LCMS m/z=366.

C. 4-buta-1,3-diynyl-N,N-diphenyl-aniline

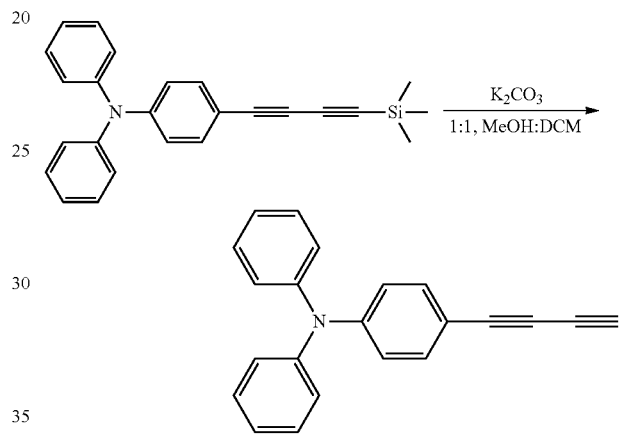

N,N-diphenyl-4-(4-trimethylsilylbuta-1,3-diynyl)aniline (0.8 g, 2.20 mmol) was added to a 50 mL flask and then DCM (10 mL) and methanol (10 mL) were added under nitrogen. To this reaction mixture anhydrous $K_2CO_3$ (1.21 g, 8.76 mmol) was added and stirred for 3 h. The reaction mixture evaporated and then resulted crude product was dissolved in dichloromethane (30 mL) and filtered through filtering funnel and mother liquor concentrated to obtain 4-buta-1,3-diynyl-N,N-diphenyl-aniline (0.6 g). LCMS m/z=294.

D. 2-[2-[4-(N-phenylanilino)phenyl]ethynyl]benzofuran-6-carbaldehyde

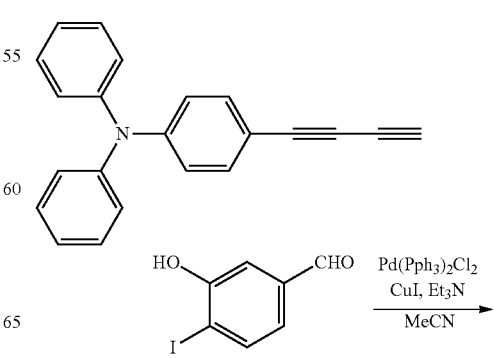

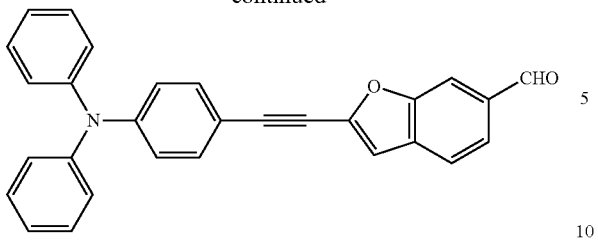

To a 50 mL flask, 3-hydroxy-4-iodobenzaldehyde (0.25 g, 1.02 mmol), 4-buta-1,3-diynyl-N,N-diphenyl-aniline (0.30 g, 1.02 mmol), bis(triphenylphosphine)palladium dichloride (0.15 g, 0.20 mmol), and copper(I) iodide (0.04 g, 0.20 mmol) were added under nitrogen. The flask was purged with nitrogen for 20 min, then degassed triethylamine (2 mL) and acetonitrile (20 mL) were added. The reaction was heated at 50° C. for 3 h. The reaction was cooled down to room temperature, then quenched with water (20 mL). The reaction mixture was extracted with ethyl acetate (25 mL) and the organic layer was washed with brine solution and dried over sodium sulfate. The organic was filtered and concentrated. Crude product was purified using chromatography on silica gel (0 to 10% ethyl acetate in hexanes) to afford 2-[2-[4-(N-phenylanilino)phenyl]ethynyl]benzofuran-6-carbaldehyde (0.15 g). UV/Vis max 390 nm, LCMS m/z=414.

E. (Z)-2-cyano-3-[2-[2-[4-(N-phenylanilino)phenyl]ethynyl]benzofuran-6-yl]prop-2-enoic acid

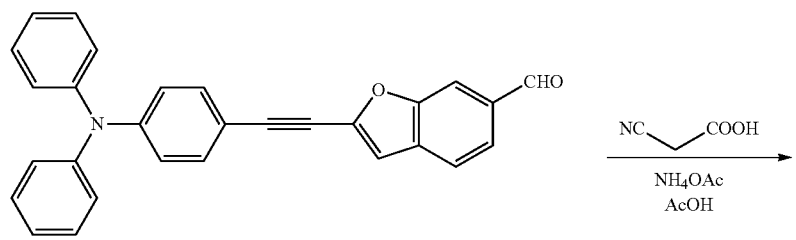

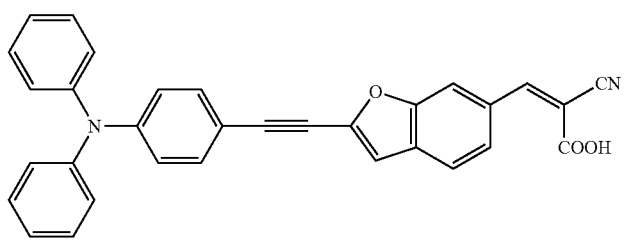

Acetic acid (8 mL) was added to 2-[2-[4-(N-phenylanilino)phenyl]ethynyl]benzofuran-6-carbaldehyde (0.075 g, 0.02 mmol), cyanoacetic acid (0.05 g, 0.05 mmol), and ammonium acetate (0.04 g, 0.05 mmol) in a round bottom flask, and the reaction was heated to reflux overnight. The reaction was cooled down to room temperature, water (10 mL) was added, then stirred for 1 h. Resulting precipitate was filtered, washed with water (2×20 mL), and dried using vacuum oven at 50° C. for 6 h to afford (Z)-2-cyano-3-[2-[2-[4-(N-phenylanilino)phenyl]ethynyl]benzofuran-6-yl]prop-2-enoic acid (0.07 g), unidentified olefin isomer. UV/Vis max 365 nm.

Example 15. Synthesis of (Z)-2-cyano-3-[2-[4-[2-[4-(N-phenylanilino)-phenyl]ethynyl]phenyl]benzofuran-6-yl]prop-2-enoic acid

A. 2-[4-[2-[4-(N-phenylanilino)phenyl]ethynyl]phenyl]benzofuran-6-carbaldehyde

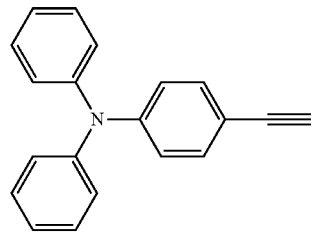

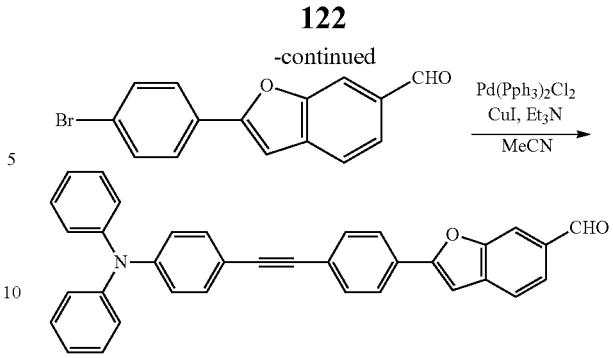

To a 50 mL flask, 2-(4-bromophenyl)benzofuran-6-carbaldehyde (0.28 g, 0.94 mmol), 4-ethynyl-N,N-diphenylaniline (0.25 g, 0.93 mmol), bis(triphenylphosphine)palladium dichloride (0.13 g, 0.20 mmol), and copper(I) iodide (0.04 g, 0.20 mmol) were added under nitrogen. The flask was purged with nitrogen for 20 min, then degassed triethylamine (3 mL) and acetonitrile (20 mL) were added. The reaction was heated at 50° C. for 3 h, then cooled down to room temperature and quenched with water (20 mL). The reaction mixture was extracted with ethyl acetate (25 mL). The organic layer was washed with brine solution, dried over sodium sulfate, then filtered and concentrated. Crude product was purified using chromatography on silica gel (0 to 10% ethyl acetate in hexanes) to afford 2-[4-[2-[4-(N-phenylanilino)phenyl]ethynyl]phenyl]benzofuran-6-carbaldehyde (0.05 g). UV/Vis max 350 nm, LCMS m/z 490.

B. (Z)-2-cyano-3-[2-[4-[2-[4-(N-phenylanilino)-phenyl]ethynyl]phenyl]benzofuran-6-yl]prop-2-enoic acid

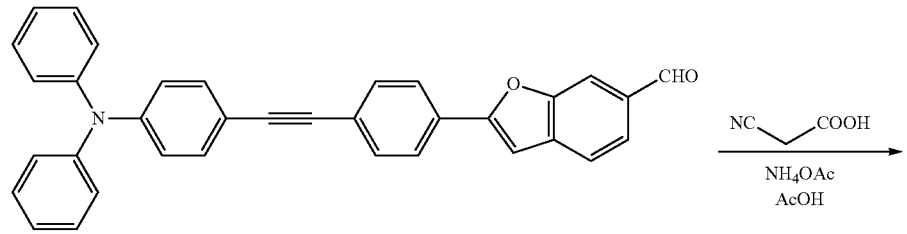

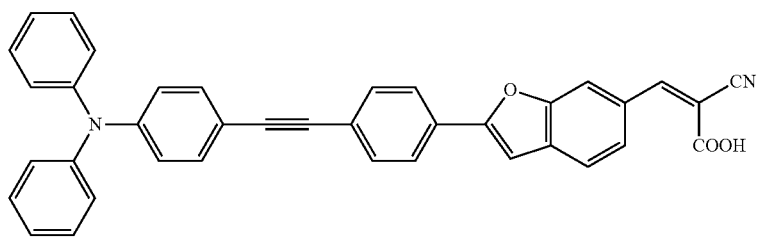

2-[4-[2-[4-(N-phenylanilino)phenyl]ethynyl]phenyl]benzofuran-6-carbaldehyde (0.05 g, 0.1 mmol), cyanoacetic acid (0.03 g, 0.3 mmol), and ammonium acetate (0.02 g, 0.42 mmol) were added to 4 mL acetic acid and the reaction was heated to reflux overnight. The reaction was cooled down to room temperature. Water (10 mL) was added, then stirred for 1 h. Resulted precipitate was filtered, washed with water (2×20 mL), and dried using vacuum oven at 50° C. for 6 h to afford (Z)-2-cyano-3-[2-[4-[2-[4-(N phenylanilino) phenyl]ethynyl]phenyl]benzofuran-6-yl]prop-2-enoic acid (0.04 g), unidentified olefin isomer. UV/Vis max 370 nm.

Example 16

Solar Cell Fabrication and Photovoltaic Characterization

FTO (fluorine-doped tin oxide)-coated glass slides were cut into 2 cm×2 cm squares and washed successively with 1% aqueous Triton X-100 solution, DI-water, and isopropanol. After drying at room temperature, the cleaned slides were treated with corona discharge (~13000V) for approximately 20 s on the conductive side. A 20% aqueous P25 dispersion was blade coated (8 microns thick) on the FTO side. The coated area was trimmed to 1.0 cm². The $TiO_2$ coated anode was sintered at 450° C. for 30 min, cooled to about 80° C. and dropped into a solution containing 0.3 mM dye and 0.3 mM chenodeoxycholic acid in 1:1 acetonitrile/t-butanol. The anodes were kept in dye solution overnight, rinsed with acetonitrile and air dried in the dark. The dye sensitized anode was sandwiched with electrochemically deposited catalyst (PEDOT or platinum) on an FTO-coated glass slide using Surlyn (Meltonix 1170-60PF from Solaronix, Switzerland) window by hot pressing at 125° C. for 45 s. A copper redox electrolyte solution (A or B as defined below) was injected between anode and cathode using a pinhole on the cathode. The pinhole was sealed using a surlyn/glass cover by a heat sealing process. A conductive silver paint was applied on the contact areas of the anode and cathode and dried to form an electrical contact. The photovoltaic performance of the fabricated cell was measured under AM 1.5 conditions (1.5 atm) at a light intensity of 97 mW/cm². The results of this experiment using various dyes, electrolytes and catalysts are shown in Table 2 below.

Electrolyte Solution A: 200 mM bis(6,6'-dimethyl-2,2'-bipyridine) copper (I) bis(trifluorosulfon)imide, 50 mM bis (6,6'-dimethyl-2,2'-bipyridine) copper (II) bis(trifluorosulfon)imide, 100 mM of Lithium bis(trifluorosulfon)imide and 0.5 M 4-(tertiarybutyl)pyridine in acetonitrile Electrolyte Solution B: 200 mM bis(2,9-dimethyl-1,10-phenanthroline) copper (I) bis(trifluorosulfon)imide, 50 mM bis(2,9-dimethyl-1,10-phenanthroline) copper (II) bis(trifluorosulfon)imide, 100 mM of Lithium bis(trifluorosulfon)imide and 0.5 M 4-(tertiarybutyl)pyridine in acetonitrile

TABLE 2

Experimental conditions and measurements.

| Dye | Catalyst | Electrolyte Solution | Open Circuit Voltage (mV) | Short Circuit Current Density (mA/cm²) | Fill Factor | Solar Conversion Efficiency (%) |
| --- | --- | --- | --- | --- | --- | --- |
| D1 | PEDOT | A | 982 | 6.53 | 0.507 | 3.27 |
| D2 | PEDOT | A | 778 | 1.25 | 0.643 | 0.63 |
| D3 | PEDOT | A | 1123 | 8.21 | 0.493 | 4.64 |
| D3 | PEDOT | B | 1198 | 6.75 | 0.519 | 4.14 |
| D5 | PEDOT | A | 1129 | 6.99 | 0.510 | 4.11 |
| D6 | PEDOT | A | 789 | 1.97 | 0.672 | 1.06 |
| D7 | PEDOT | A | 854 | 2.87 | 0.636 | 1.60 |
| D9 | PEDOT | A | 1130 | 6.7 | 0.454 | 3.59 |
| D9 | PEDOT | B | 1160 | 5.06 | 0.545 | 3.24 |
| D10 | PEDOT | A | 1110 | 7.06 | 0.462 | 3.67 |
| D10 | PEDOT | B | 1129 | 7.41 | 0.516 | 4.37 |
| D11 | PEDOT | A | 688 | 0.927 | 0.48 | 0.31 |
| D12 | PEDOT | A | 987 | 6.09 | 0.528 | 3.21 |
| D13 | Pt | A | 1100 | 5.5 | 0.528 | 3.26 |
| D15 | Pt | A | 978 | 4.85 | 0.6 | 2.90 |
| D16 | Pt | A | 1181 | 5.27 | 0.492 | 3.16 |
| D16 | PEDOT | A | 1197 | 6.12 | 0.551 | 4.16 |
| D35 (Dyenamo, Sweden) | PEDOT | B | 1116 | 8.2 | 0.472 | 4.37 |

TABLE 2-continued

Experimental conditions and measurements.

| Dye | Catalyst | Electrolyte Solution | Open Circuit Voltage (mV) | Short Circuit Current Density (mA/cm$^2$) | Fill Factor | Solar Conversion Efficiency (%) |
|---|---|---|---|---|---|---|

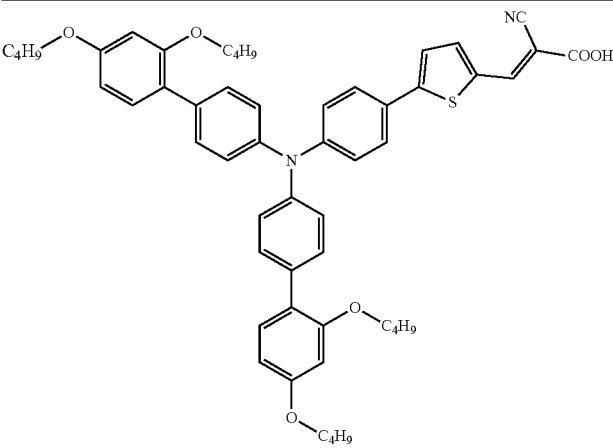

Dyenamo Orange D35

Solar Cell Dye Combinations

Example 17

Fluorine-doped tin oxide (FTO) coated glasses were cut into 2 cm×2 cm size and cleaned by washing with successive 1% aqueous Triton X-100 solution, deionized (DI) water, and isopropanol. After drying at room temperature, the cleaned FTO glasses were treated with Corona discharge (~13000V) for approximately 20 seconds on the conducting side. An aqueous dispersion containing 20% by weight of TiO$_2$ (Degussa P25 with a particle size of 21+5 nm) and 5% by weight of poly(4-vinyl pyridine) was prepared and blade coated (6-8 microns thick) on the FTO coated side of the glass. The coating area was trimmed to 1.0 cm$^2$. The TiO$_2$ coated anode was sintered at 450° C. for 30 minutes, cooled to about 80° C. and dropped into a dye solution containing 0.3 mM overall concentration of mix dye with various dye molar ratios (shown in Table 3) and 0.3 mM chenodeoxycholic acid in 1:1 acetonitrile/t-butanol. The anodes were kept in dye solution for overnight, rinsed with acetonitrile and air dried in the dark. The dye sensitized anode was sandwiched with either electrochemically deposited PEDOT catalyst or pyrolytic platinum catalyst on a FTO coated glass slide using surlyn (Meltonix 1170-60PF from Solaronix, Switzerland) window by hot pressing at 125° C. for 45 seconds. A copper redox electrolyte solution consisting of 200 mM bis(6,6'-dimethyl-2,2'-bipyridine) copper (I) bis(trifluorosulfon)imide, 50 mM bis(6,6'-dimethyl-2,2'-bipyridine) copper (II) bis(trifluorosulfon)imide, 100 mM of Lithium bis(trifluorosulfon)imide and 0.5 M 4-(t-butyl)pyridine in a select solvent was injected between anode and cathode using pinhole on the cathode. The pinhole was sealed using surlyn/glass cover using heat sealing process. A conductive silver paint was applied on the contact areas of anode and cathode and dried to form electrical contact. The photovoltaic performance of the fabricated cells was measured under indoor light exposure conditions at 740 lux and is shown in Table 3.

TABLE 3

Photovoltaic characteristics of solar cells made with various co-sensitizer combinations at 740 lux indoor light exposure with volatile and stable electrolytes

| Dye composition in the sensitizer solution | Catalyst on the cathode | Electrolyte Solvent | Voc (mV) | Jsc (mA/cm2) | ff | Power density (uW/cm$^2$) |
|---|---|---|---|---|---|---|
| WD3 | PEDOT | Acetonitrile | 791.02 | 0.024 | 0.75 | 14.18 |
| WD10 | PEDOT | Acetonitrile | 822.76 | 0.045 | 0.67 | 24.92 |
| WD14 | PEDOT | Acetonitrile | 699.23 | 0.043 | 0.62 | 18.58 |
| WE11 | PEDOT | Acetonitrile | 630.67 | 0.019 | 0.45 | 5.44 |
| 80/20 WD3/WD14 | PEDOT | Acetonitrile | 712.40 | 0.028 | 0.70 | 13.86 |
| 80/20 WD3/WE11 | PEDOT | Acetonitrile | 878.77 | 0.067 | 0.71 | 41.86 |
| 80/20 WD10/WD14 | PEDOT | Acetonitrile | 762.28 | 0.047 | 0.61 | 21.96 |
| 80/20 WD10/WE11 | PEDOT | Acetonitrile | 772.79 | 0.062 | 0.63 | 30.09 |
| WD3 | PEDOT | sulfolane | 944.86 | 0.022 | 0.72 | 15.01 |
| WD10 | PEDOT | sulfolane | 957.11 | 0.05 | 0.66 | 34.11 |
| WD14 | PEDOT | sulfolane | 700.39 | 0.04 | 0.70 | 18.63 |
| WE11 | PEDOT | sulfolane | 666.21 | 0.02 | 0.68 | 9.89 |

TABLE 3-continued

Photovoltaic characteristics of solar cells made with various co-sensitizer combinations at 740 lux indoor light exposure with volatile and stable electrolytes

| Dye composition in the sensitizer solution | Catalyst on the cathode | Electrolyte Solvent | Voc (mV) | Jsc (mA/cm2) | ff | Power density (uW/cm$^2$) |
|---|---|---|---|---|---|---|
| 80/20 WD3/WD14 | PEDOT | sulfolane | 885.38 | 0.06 | 0.66 | 33.69 |
| 80/20 WD3/WE11 | PEDOT | sulfolane | 947.80 | 0.07 | 0.66 | 45.11 |
| 80/20 WD10/WD14 | PEDOT | sulfolane | 856.48 | 0.06 | 0.68 | 33.63 |
| 80/20 WD10/WE11 | PEDOT | sulfolane | 921.00 | 0.07 | 0.64 | 40.14 |
| WD3 | Pt | sulfolane | 926.88 | 0.03 | 0.69 | 16.08 |
| WD10 | Pt | sulfolane | 936.50 | 0.05 | 0.63 | 28.18 |
| WD14 | Pt | sulfolane | 698.18 | 0.04 | 0.67 | 16.35 |
| WE11 | Pt | sulfolane | 668.97 | 0.03 | 0.64 | 11.60 |
| 80/20 WD3/WD14 | Pt | sulfolane | 844.56 | 0.05 | 0.64 | 25.25 |
| 80/20 WD3/WE11 | Pt | sulfolane | 937.78 | 0.07 | 0.62 | 41.35 |
| 80/20 WD10/WD14 | Pt | sulfolane | 880.45 | 0.06 | 0.61 | 32.82 |
| 80/20 WD10/WE11 | Pt | sulfolane | 902.22 | 0.07 | 0.61 | 37.12 |

Example 18

Fluorine-doped tin oxide (FTO) coated glasses were cut into 2 cm×2 cm size and cleaned by washing with successive 1% aqueous Triton X-100 solution, deionized (DI) water, and isopropanol. After drying at room temperature, the cleaned FTO glasses were treated with Corona discharge (~13000V) for approximately 20 seconds on the conducting side. An aqueous dispersion containing 20% by weight of TiO$_2$ (Degussa P25 with a particle size of 21+5 nm) and 5% by weight of poly(4-vinyl pyridine) was prepared and blade coated (6-8 microns thick) on the FTO coated side of the glass. The coating area was trimmed to 1.0 cm$^2$. The TiO$_2$ coated anode was sintered at 450° C. for 30 minutes, cooled to about 80° C. and dropped into a dye solution containing 0.3 mM overall concentration of mix dye with various dye molar ratios (shown in Tables 4-6) and 0.3 mM chenodeoxycholic acid in 1:1 acetonitrile/t-butanol. The anodes were kept in dye solution for overnight, rinsed with acetonitrile and air dried in the dark. The dye sensitized anode was sandwiched pyrolytic platinum catalyst on a FTO coated glass slide using surlyn (Meltonix 1170-60PF from Solaronix, Switzerland) window by hot pressing at 125° C. for 45 seconds. A copper redox electrolyte solution consisting of 250 mM bis(6,6'-dimethyl-2,2'-bipyridine) copper (I) bis(trifluorosulfon)imide, 50 mM bis(6,6'-dimethyl-2,2'-bipyridine) copper (II) bis(trifluorosulfon)imide, 100 mM of Lithium bis(trifluorosulfon)-imide and 0.5 M 4-(t-butyl) pyridine in sulfolane was injected between anode and cathode using pinhole on the cathode. The pinhole was sealed using surlyn/glass cover using heat sealing process. A conductive silver paint was applied on the contact areas of anode and cathode and dried to form electrical contact. The photovoltaic performance of the fabricated cells was measured under indoor light exposure conditions and are shown in Tables 4-6.

TABLE 4

Photovoltaic characteristics of solar cells made with various co-sensitizer combinations at 360 lux indoor light exposure

| Dye combination | Dye 1 | Dye 2 | Voc (mV) | Jsc (mA/cm$^2$) | fill factor | Power density (uW/cm$^2$) |
|---|---|---|---|---|---|---|
| WD3 cosensitized with XY1b dye | 100% WD3 | — | 931.15 | 0.012 | 0.78 | 8.73 |
|  | 90% WD3 | 10% XY1b | 940.64 | 0.043 | 0.60 | 24.15 |
|  | 85% WD3 | 15% XY1b | 942.41 | 0.047 | 0.62 | 27.46 |
|  | 85% WD3 | 100% XY1b | 874.82 | 0.038 | 0.54 | 17.98 |
| WD3 cosensitized with WD14 dye | 100% WD3 | — | 931.15 | 0.012 | 0.78 | 8.73 |
|  | 90% WD3 | 10% WD14 | 895.03 | 0.026 | 0.59 | 13.75 |
|  | 80% WD3 | 20% WD14 | 879.61 | 0.032 | 0.56 | 15.79 |
|  | 70% WD3 | 30% WD14 | 867.11 | 0.036 | 0.50 | 15.55 |
|  | 50% WD3 | 50% WD14 | 807.31 | 0.033 | 0.53 | 14.04 |
|  | — | 100% WD14 | 697.94 | 0.024 | 0.65 | 10.95 |
| WD3 cosensitized with WE11 dye | 100% WD3 | — | 931.15 | 0.012 | 0.78 | 8.73 |
|  | 90% WD3 | 10% WE11 | 937.44 | 0.029 | 0.61 | 16.53 |
|  | 80% WD3 | 20% WE11 | 944.03 | 0.036 | 0.58 | 19.58 |
|  | 70% WD3 | 30% WE11 | 901.71 | 0.037 | 0.60 | 20.02 |
|  | 50% WD3 | 50% WE11 | 907.38 | 0.04 | 0.55 | 20.00 |
|  | — | 100% WE11 | 795.75 | 0.035 | 0.54 | 15.10 |
| WD3 cosensitized with WE10 dye | 100% WD3 | — | 931.15 | 0.012 | 0.78 | 8.73 |
|  | 90% WD3 | 10% WE10 | 944.07 | 0.031 | 0.65 | 18.99 |
|  | 80% WD3 | 20% WE10 | 948.54 | 0.037 | 0.58 | 20.50 |

TABLE 4-continued

Photovoltaic characteristics of solar cells made with various co-sensitizer combinations at 360 lux indoor light exposure

| Dye combination | Dye 1 | Dye 2 | Voc (mV) | Jsc (mA/cm$^2$) | fill factor | Power density (uW/cm$^2$) |
|---|---|---|---|---|---|---|
| | 70% WD3 | 30% WE10 | 950.37 | 0.038 | 0.59 | 21.16 |
| | 50% WD3 | 50% WE10 | 917.23 | 0.043 | 0.56 | 22.21 |
| | — | 100% WE10 | 840.97 | 0.04 | 0.61 | 20.35 |

TABLE 5

Photovoltaic characteristics of solar cells made with various co-sensitizer combinations at 740 lux indoor light exposure

| Dye combination | Dye 1 | Dye 2 | Voc (mV) | Jsc (mA/cm$^2$) | fill factor | Power density (uW/cm$^2$) |
|---|---|---|---|---|---|---|
| WD3 cosensitized with XY1b dye | 100% WD3 | — | 952.78 | 0.022 | 0.68 | 14.34 |
| | 90% WD3 | 10% XY1b | 966.94 | 0.084 | 0.51 | 41.75 |
| | 85% WD3 | 15% XY1b | 962.39 | 0.090 | 0.51 | 44.09 |
| | 85% WD3 | 100% XY1b | 903.53 | 0.071 | 0.47 | 30.02 |
| WD3 cosensitized with WD14 dye | 100% WD3 | — | 952.78 | 0.022 | 0.68 | 14.34 |
| | 90% WD3 | 10% WD14 | 922.74 | 0.050 | 0.50 | 23.25 |
| | 80% WD3 | 20% WD14 | 908.49 | 0.061 | 0.48 | 26.38 |
| | 70% WD3 | 30% WD14 | 894.52 | 0.064 | 0.40 | 23.07 |
| | 50% WD3 | 50% WD14 | 851.37 | 0.058 | 0.40 | 19.85 |
| | — | 100% WD14 | 725.40 | 0.046 | 0.58 | 19.29 |
| WD3 cosensitized with WE11 dye | 100% WD3 | — | 952.78 | 0.022 | 0.68 | 14.34 |
| | 90% WD3 | 10% WE11 | 959.96 | 0.056 | 0.55 | 29.62 |
| | 80% WD3 | 20% WE11 | 961.54 | 0.067 | 0.51 | 32.92 |
| | 70% WD3 | 30% WE11 | 934.88 | 0.071 | 0.53 | 34.98 |
| | 50% WD3 | 50% WE11 | 947.10 | 0.076 | 0.48 | 34.77 |
| | — | 100% WE11 | 865.69 | 0.070 | 0.44 | 26.91 |
| WD3 cosensitized with WE10 dye | 100% WD3 | — | 952.78 | 0.022 | 0.68 | 14.34 |
| | 90% WD3 | 10% WE10 | 957.94 | 0.060 | 0.57 | 32.93 |
| | 80% WD3 | 20% WE10 | 964.11 | 0.075 | 0.46 | 33.48 |
| | 70% WD3 | 30% WE10 | 964.86 | 0.075 | 0.51 | 36.62 |
| | 50% WD3 | 50% WE10 | 943.71 | 0.088 | 0.49 | 41.02 |
| | — | 100% WE10 | 876.21 | 0.081 | 0.52 | 36.62 |

TABLE 6

Photovoltaic characteristics of solar cells made with various co-sensitizer combinations at 1100 lux indoor light exposure

| Dye combination | Dye 1 | Dye 2 | Voc (mV) | Jsc (mA/cm$^2$) | fill factor | Power density (uW/cm$^2$) |
|---|---|---|---|---|---|---|
| WD3 cosensitized with XY1b dye | 100% WD3 | — | 968.70 | 0.035 | 0.66 | 22.41 |
| | 90% WD3 | 10% XY1b | 979.55 | 0.123 | 0.48 | 57.23 |
| | 85% WD3 | 15% XY1b | 970.71 | 0.131 | 0.48 | 60.53 |
| | — | 100% XY1b | 920.96 | 0.108 | 0.43 | 42.47 |
| WD3 cosensitized with WD14 dye | 100% WD3 | — | 968.70 | 0.035 | 0.66 | 22.41 |
| | 90% WD3 | 10% WD14 | 945.32 | 0.078 | 0.47 | 34.88 |
| | 80% WD3 | 20% WD14 | 930.14 | 0.092 | 0.44 | 37.99 |
| | 70% WD3 | 30% WD14 | 917.26 | 0.098 | 0.39 | 34.88 |
| | 50% WD3 | 50% WD14 | 874.46 | 0.089 | 0.39 | 30.04 |
| | — | 100% WD14 | 757.38 | 0.070 | 0.52 | 27.41 |
| WD3 cosensitized with WE11 dye | 100% WD3 | — | 968.70 | 0.035 | 0.66 | 22.41 |

TABLE 6-continued

Photovoltaic characteristics of solar cells made with various co-sensitizer combinations at 1100 lux indoor light exposure

| Dye combination | Dye 1 | Dye 2 | Voc (mV) | Jsc (mA/cm$^2$) | fill factor | Power density (uW/cm$^2$) |
|---|---|---|---|---|---|---|
| | 90% WD3 | 10% WE11 | 983.97 | 0.083 | 0.51 | 41.57 |
| | 80% WD3 | 20% WE11 | 975.89 | 0.097 | 0.46 | 43.64 |
| | 70% WD3 | 30% WE11 | 951.06 | 0.106 | 0.49 | 49.30 |
| | 50% WD3 | 50% WE11 | 964.80 | 0.112 | 0.43 | 46.79 |
| | — | 100% WE11 | 890.68 | 0.102 | 0.42 | 38.43 |
| WD3 cosensitized with WE10 dye | 100% WD3 | — | 968.70 | 0.035 | 0.66 | 22.41 |
| | 90% WD3 | 10% WE10 | 983.61 | 0.092 | 0.54 | 48.96 |
| | 80% WD3 | 20% WE10 | 983.98 | 0.111 | 0.44 | 47.62 |
| | 70% WD3 | 30% WE10 | 982.44 | 0.111 | 0.44 | 48.42 |
| | 50% WD3 | 50% WE10 | 963.36 | 0.129 | 0.44 | 54.80 |
| | — | 100% WE10 | 905.80 | 0.117 | 0.46 | 49.07 |

Example 19

Fluorine-doped tin oxide (FTO) coated glasses were cut into 2 cm×2 cm size and cleaned by washing with successive 1% aqueous Triton X-100 solution, deionized (DI) water, and isopropanol. After drying at room temperature, the cleaned FTO glasses were treated with Corona discharge (~13000V) for approximately 20 seconds on the conducting side. An aqueous dispersion containing 20% by weight of TiO$_2$ (Degussa P25 with a particle size of 21±5 nm) and 5% by weight of poly(4-vinyl pyridine) was prepared and blade coated (6-8 microns thick) on the FTO coated side of the glass. The coating area was trimmed to 1.0 cm$^2$. The TiO$_2$ coated anode was sintered at 450° C. for 30 minutes, cooled to about 80° C. and dropped into a dye solution containing 0.3 mM overall concentration of mix dye with various dye molar ratios (shown in Table 7) and 0.3 mM chenodeoxycholic acid in 1:1 acetonitrile/t-butanol. The anodes were kept in dye solution for overnight, rinsed with acetonitrile and air dried in the dark. The dye sensitized anode was sandwiched pyrolytic platinum catalyst on a FTO coated glass slide using surlyn (Meltonix 1170-60PF from Solaronix, Switzerland) window by hot pressing at 125° C. for 45 seconds. A copper redox electrolyte solution consisting of 250 mM bis(6,6'-dimethyl-2,2'-bipyridine) copper (1)bis(trifluorosulfon)imide, 50 mM bis(6,6'-dimethyl-2,2'-bipyridine) copper (II) bis(trifluorosulfon)imide, 100 mM of Lithium bis(trifluorosulfon)imide and 0.5 M 4-(t-butyl)pyridine in sulfolane was injected between anode and cathode using pinhole on the cathode. The pinhole was sealed using surlyn/glass cover using heat sealing process. A conductive silver paint was applied on the contact areas of anode and cathode and dried to form electrical contact. The photovoltaic performance of the fabricated cells was measured under indoor light exposure conditions and is shown in Table 7.

TABLE 7

Photovoltaic characteristics of solar cells made with various co-sensitizer combinations at 740 lux indoor light exposure

| Dye 1 | Dye 2 | Voc (mV) | Jsc (mA/cm$^2$) | Fill factor | Power density (uW/cm$^2$) | Synergism |
|---|---|---|---|---|---|---|
| 100% WD3 | — | 931.15 | 0.012 | 0.78 | 8.73 | N/A |
| 100% MK2 | — | 686.35 | 0.029 | 0.676 | 13.46 | N/A |
| 100% XY1b | — | 861.47 | 0.06 | 0.584 | 30.19 | N/A |
| 100% WE11 | — | 851.71 | 0.067 | 0.605 | 34.52 | N/A |
| 100% D35 | — | 919.85 | 0.057 | 0.69 | 36.18 | N/A |
| 100% WD13 | — | 878.54 | 0.016 | 0.717 | 10.08 | N/A |
| 90% WD3 | 10% MK2 | 967.33 | 0.042 | 0.735 | 29.86 | Yes |
| 90% WD3 | 10% WD14 | 923.66 | 0.049 | 0.646 | 29.24 | No |
| 90% WD3 | 10% WE11 | 974.22 | 0.054 | 0.694 | 36.51 | Yes |
| 80% WD3 | 20% WE11 | 978.23 | 0.064 | 0.635 | 39.76 | Yes |
| 90% WD3 | 10% WE11 | 979.94 | 0.054 | 0.66 | 34.93 | Yes |
| 80% WD3 | 20% WE11 | 975.99 | 0.07 | 0.674 | 46.05 | Yes |
| 50% WD3 | 50% WD9 | 957.48 | 0.038 | 0.69 | 25.11 | No |
| 80% WD3 | 20% BOD4 | 958.47 | 0.039 | 0.71 | 26.54 | Yes |
| 90% D35 | 10% WD14 | 882.30 | 0.056 | 0.659 | 32.56 | No |
| 80% D35 | 20% WD14 | 823.37 | 0.039 | 0.657 | 21.10 | No |
| 50% D35 | 50% WD14 | 753.87 | 0.037 | 0.657 | 18.33 | No |
| 90% D35 | 10% WE11 | 918.34 | 0.065 | 0.64 | 38.20 | No |
| 90% WD13 | 10% WE11 | 964.95 | 0.061 | 0.664 | 39.08 | Yes |
| 90% WD13 | 10% MK2 | 933.35 | 0.041 | 0.693 | 26.52 | Yes |
| 90% WD13 | 10% XY1b | 980.91 | 0.083 | 0.661 | 53.82 | Yes |

What is claimed is:

1. A compound of formula I:

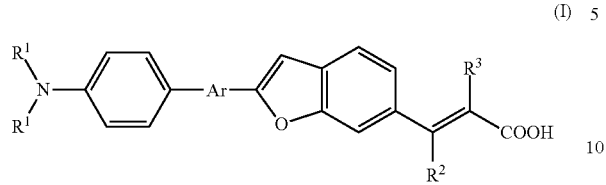

wherein
each R¹ is

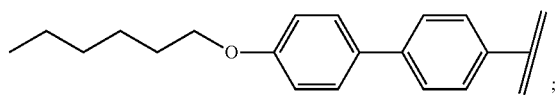

—Ar— is

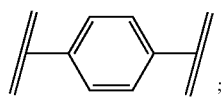

$R^2$ is H, and
$R^3$ is —CN.

2. A dye sensitized solar cell comprising a solar cell dye, wherein the solar cell dye is the compound of claim 1.

3. A method of making a Dye-Sensitized Solar Cell ("DSSC") comprising the step of incorporating a solar cell dye into the DSSC, wherein the solar cell dye is the compound of claim 1.

* * * * *